US012735697B2

(12) United States Patent
Yang et al.

(10) Patent No.: US 12,735,697 B2
(45) Date of Patent: Sep. 15, 2026

(54) METHOD FOR SELECTING ANTIBODY FRAGMENTS, RECOMBINANT ANTIBODIES PRODUCED THEREFROM, AND USES THEREOF

(71) Applicant: Academia Sinica, Taipei City (TW)

(72) Inventors: An-Suei Yang, Seattle, WA (US); Chung-Ming Yu, New Taipei City (TW); Ing-Chien Chen, Taipei City (TW); Chao-Ping Tung, Taipei City (TW); Hung-Pin Peng, Taipei City (TW)

(73) Assignee: Academia Sinica, Taipei City (TW)

( * ) Notice: Subject to any disclaimer, the term of this patent is extended or adjusted under 35 U.S.C. 154(b) by 919 days.

(21) Appl. No.: 18/008,753

(22) PCT Filed: Jun. 7, 2021

(86) PCT No.: PCT/US2021/036274

§ 371 (c)(1),
(2) Date: Dec. 7, 2022

(87) PCT Pub. No.: WO2021/252406

PCT Pub. Date: Dec. 16, 2021

(65) Prior Publication Data

US 2023/0212554 A1 Jul. 6, 2023

Related U.S. Application Data

(60) Provisional application No. 63/036,143, filed on Jun. 8, 2020.

(51) Int. Cl.
*G01N 33/569* (2006.01)
*C07K 16/10* (2026.01)
*C07K 16/108* (2026.01)
*C12N 15/10* (2006.01)

(52) U.S. Cl.
CPC ........ *C12N 15/1037* (2013.01); *C07K 16/108* (2026.01); *G01N 33/56983* (2013.01); *C07K 2317/622* (2013.01); *C07K 2317/92* (2013.01); *G01N 2333/11* (2013.01); *G01N 2470/04* (2021.08)

(58) Field of Classification Search
None
See application file for complete search history.

(56) References Cited

U.S. PATENT DOCUMENTS 9,714,435 B2 * 7/2017 Dicks ..................... A61K 48/00
10,336,815 B2 * 7/2019 Yang .................. C07K 16/1018
10,415,033 B2 * 9/2019 Yang .................. C07K 16/2827
11,434,277 B2 * 9/2022 Yang .................. C12N 15/1037

* cited by examiner

*Primary Examiner* — Agnieszka Boesen
(74) *Attorney, Agent, or Firm* — NZ Carr Law Office

(57) ABSTRACT

Disclosed herein are methods for selecting an antibody fragment specific to an influenza virus. According to certain embodiments of the present disclosure, the influenza virus may be influenza virus type A (IAV) or influenza virus type B (IBV). Also disclosed herein are the selected antibodies, recombinant antibody produced from the selected antibodies, and the uses thereof in the diagnosis of influenza virus infection.

10 Claims, 3 Drawing Sheets

Specification includes a Sequence Listing.

SEQUENCE LISTING

```
<160> NUMBER OF SEQ ID NOS: 206

<210> SEQ ID NO 1
<211> LENGTH: 489
```

```
<212> TYPE: PRT
<213> ORGANISM: Artificial Sequence
<220> FEATURE:
<223> OTHER INFORMATION: synthesized_NPA1

<400> SEQUENCE: 1

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Asp Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Lys Met Val Leu Ser Ala Phe Asp Glu Arg Arg Asn Arg Tyr Leu Glu
65                  70                  75                  80

Glu His Pro Ser Thr Gly Lys Asp Pro Lys Lys Thr Gly Gly Pro Ile
                85                  90                  95

Tyr Lys Arg Val Asp Gly Arg Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Val Lys Arg Gly Ile Asn Asp Arg Asn Phe Trp Arg
        195                 200                 205

Gly Glu Asn Gly Arg Lys Thr Arg Ser Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ser Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Leu Leu Ser Phe Ile Arg Gly Thr Lys Val
            340                 345                 350

Ser Pro Arg Gly Lys Leu Ser Thr Arg Gly Ile Gln Ile Ala Ser Asn
        355                 360                 365

Glu Asn Met Asp Asn Met Gly Ser Ser Thr Leu Glu Leu Arg Ser Gly
    370                 375                 380
```

```
Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Ala Phe Ser Val Gln Arg
                405                 410                 415

Asn Leu Pro Phe Glu Lys Ser Thr Val Met Ala Ala Phe Thr Gly Asn
            420                 425                 430

Thr Glu Gly Arg Thr Ser Asp Met Arg Ala Glu Ile Ile Arg Met Met
        435                 440                 445

Glu Gly Ala Lys Pro Glu Glu Val Ser Phe Arg Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe
                485


<210> SEQ ID NO 2
<211> LENGTH: 489
<212> TYPE: PRT
<213> ORGANISM: Artificial Sequence
<220> FEATURE:
<223> OTHER INFORMATION: synthesized_NPA2

<400> SEQUENCE: 2

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Ile Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Phe Glu Asp Leu
                245                 250                 255
```

```
Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Lys Val
            340                 345                 350

Ile Pro Arg Gly Lys Leu Ser Thr Arg Gly Val Gln Ile Ala Ser Asn
        355                 360                 365

Glu Asn Met Glu Thr Met Gly Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe
                485


<210> SEQ ID NO 3
<211> LENGTH: 489
<212> TYPE: PRT
<213> ORGANISM: Artificial Sequence
<220> FEATURE:
<223> OTHER INFORMATION: synthesized_NPA3

<400> SEQUENCE: 3

Met Ala Ser Gln Gly Thr Lys Arg Ser Tyr Glu Gln Met Glu Thr Gly
1               5                   10                  15

Gly Glu Arg Gln Asp Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Ile Asp Gly Lys Trp Met Arg Glu Leu Ile Leu Tyr Asp
            100                 105                 110

Lys Glu Glu Ile Arg Arg Val Trp Arg Gln Ala Asn Asn Gly Glu Asp
        115                 120                 125
```

-continued

```
Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Val Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
    290                 295                 300

Lys Leu Leu Gln Asn Ser Gln Val Val Ser Leu Met Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Lys Lys Val
            340                 345                 350

Ile Pro Arg Gly Lys Leu Ser Thr Arg Gly Val Gln Ile Ala Ser Asn
        355                 360                 365

Glu Asn Val Glu Thr Met Asp Ser Asn Thr Leu Glu Leu Arg Ser Arg
    370                 375                 380

Tyr Trp Ala Ile Arg Thr Arg Ser Gly Gly Asn Thr Asn Gln Gln Lys
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Val Met Ala Ala Phe Ser Gly Asn
            420                 425                 430

Asn Glu Gly Arg Thr Ser Asp Met Arg Thr Glu Val Ile Arg Met Met
        435                 440                 445

Glu Ser Ala Lys Pro Glu Asp Leu Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe
                485
```

<210> SEQ ID NO 4
<211> LENGTH: 489
<212> TYPE: PRT
<213> ORGANISM: Artificial Sequence
<220> FEATURE:
<223> OTHER INFORMATION: synthesized_NPA4

<400> SEQUENCE: 4

-continued

```
Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Asn Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Val Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Ile Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Leu Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Ile Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Val Asp Pro Phe
    290                 295                 300

Lys Leu Leu Gln Thr Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Arg Val
            340                 345                 350

Leu Pro Arg Gly Lys Leu Ser Thr Arg Gly Val Gln Ile Ala Ser Asn
        355                 360                 365

Glu Asn Met Asp Ala Ile Val Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Thr Gln Pro Thr Phe Ser Val Gln Arg
                405                 410                 415

Asn Leu Pro Phe Asp Lys Ala Thr Ile Met Ala Ala Phe Thr Gly Asn
```

```
            420                 425                 430

Thr Glu Gly Arg Thr Ser Asp Met Arg Ala Glu Ile Ile Lys Met Met
        435                 440                 445

Glu Ser Ala Arg Pro Glu Glu Val Ser Phe Gln Gly Arg Gly Val Phe
    450                 455                 460

Glu Leu Ser Asp Glu Arg Ala Thr Asn Pro Ile Val Pro Ser Phe Asp
465                 470                 475                 480

Met Ser Asn Glu Gly Ser Tyr Phe Phe
                485


<210> SEQ ID NO 5
<211> LENGTH: 489
<212> TYPE: PRT
<213> ORGANISM: Artificial Sequence
<220> FEATURE:
<223> OTHER INFORMATION: synthesized_NPA5

<400> SEQUENCE: 5

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

His Asp Phe Glu Arg Glu Gly Tyr Ser Leu Val Gly Ile Asp Pro Phe
```

```
    290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Thr Met Asp Ser Asn Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Lys Met Met
        435                 440                 445

Glu Ser Ala Arg Pro Glu Asp Leu Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe
                485


<210> SEQ ID NO 6
<211> LENGTH: 548
<212> TYPE: PRT
<213> ORGANISM: Artificial Sequence
<220> FEATURE:
<223> OTHER INFORMATION: synthesized_NPB1

<400> SEQUENCE: 6

Met Ser Asn Met Asp Ile Asp Gly Ile Asn Thr Gly Thr Ile Asp Lys
1               5                   10                  15

Thr Pro Glu Glu Ile Thr Ser Gly Thr Ser Gly Thr Thr Arg Pro Ile
            20                  25                  30

Ile Arg Pro Ala Thr Leu Ala Pro Pro Ser Asn Lys Arg Thr Arg Asn
        35                  40                  45

Pro Ser Pro Glu Arg Ala Thr Thr Ser Ser Glu Asp Asp Val Gly Arg
    50                  55                  60

Lys Thr Gln Lys Lys Gln Thr Pro Thr Glu Ile Lys Lys Ser Val Tyr
65                  70                  75                  80

Asn Met Val Val Lys Leu Gly Glu Phe Tyr Asn Gln Met Met Val Lys
                85                  90                  95

Ala Gly Leu Asn Asp Asp Met Glu Arg Asn Leu Ile Gln Asn Ala His
            100                 105                 110

Ala Val Glu Arg Ile Leu Leu Ala Ala Thr Asp Asp Lys Lys Thr Glu
        115                 120                 125

Phe Gln Lys Lys Lys Asn Ala Arg Asp Val Lys Glu Gly Lys Glu Glu
    130                 135                 140

Ile Asp His Asn Lys Thr Gly Gly Thr Phe Tyr Lys Met Val Arg Asp
145                 150                 155                 160

Asp Lys Thr Ile Tyr Phe Ser Pro Ile Arg Ile Thr Phe Leu Lys Glu
```

-continued

```
                165                 170                 175

Glu Val Lys Thr Met Tyr Lys Thr Thr Met Gly Ser Asp Gly Phe Ser
            180                 185                 190

Gly Leu Asn His Ile Met Ile Gly His Ser Gln Met Asn Asp Val Cys
        195                 200                 205

Phe Gln Arg Ser Lys Ala Leu Lys Arg Val Gly Leu Asp Pro Ser Leu
    210                 215                 220

Ile Ser Thr Phe Ala Gly Ser Thr Ile Pro Arg Arg Ser Gly Ala Thr
225                 230                 235                 240

Gly Val Ala Ile Lys Gly Gly Gly Thr Leu Val Ala Glu Ala Ile Arg
                245                 250                 255

Phe Ile Gly Arg Ala Met Ala Asp Arg Gly Leu Leu Arg Asp Ile Lys
            260                 265                 270

Ala Lys Thr Ala Tyr Glu Lys Ile Leu Leu Asn Leu Lys Asn Lys Cys
        275                 280                 285

Ser Ala Pro Gln Gln Lys Ala Leu Val Asp Gln Val Ile Gly Ser Arg
    290                 295                 300

Asn Pro Gly Ile Ala Asp Ile Glu Asp Leu Thr Leu Leu Ala Arg Ser
305                 310                 315                 320

Met Val Val Val Arg Pro Ser Val Ala Ser Lys Val Val Leu Pro Ile
                325                 330                 335

Ser Ile Tyr Ala Lys Ile Pro Gln Leu Gly Phe Asn Val Glu Glu Tyr
            340                 345                 350

Ser Met Val Gly Tyr Glu Ala Met Ala Leu Tyr Asn Met Ala Thr Pro
        355                 360                 365

Val Ser Ile Leu Arg Met Gly Asp Asp Ala Lys Asp Lys Ser Gln Leu
    370                 375                 380

Phe Phe Met Ser Cys Phe Gly Ala Ala Tyr Glu Asp Leu Arg Val Leu
385                 390                 395                 400

Ser Ala Leu Thr Gly Thr Glu Phe Lys Pro Arg Ser Ala Leu Lys Cys
                405                 410                 415

Lys Gly Phe His Val Pro Ala Lys Glu Gln Val Glu Gly Met Gly Ala
            420                 425                 430

Ala Leu Met Ser Ile Lys Leu Gln Phe Trp Ala Pro Met Thr Arg Ser
        435                 440                 445

Gly Gly Asn Glu Val Gly Gly Asp Gly Gly Ser Gly Gln Ile Ser Cys
    450                 455                 460

Ser Pro Val Phe Ala Val Glu Arg Pro Ile Ala Leu Ser Lys Gln Ala
465                 470                 475                 480

Val Arg Arg Met Leu Ser Met Asn Ile Glu Gly Arg Asp Ala Asp Val
                485                 490                 495

Lys Gly Asn Leu Leu Lys Met Met Asn Asp Ser Met Ala Lys Lys Thr
            500                 505                 510

Ser Gly Asn Ala Phe Ile Gly Lys Lys Met Phe Gln Ile Ser Asp Lys
        515                 520                 525

Asn Lys Thr Asn Pro Val Glu Ile Pro Ile Lys Gln Thr Ile Pro Asn
    530                 535                 540

Phe Phe Phe Gly
545

<210> SEQ ID NO 7
<211> LENGTH: 11
<212> TYPE: PRT
<213> ORGANISM: Artificial Sequence
```

```
<220> FEATURE:
<223> OTHER INFORMATION: synthesized_NP1-CDR-L1

<400> SEQUENCE: 7

Arg Ala Ser Gln Asp Val Asp Asp Asp Val Ala
1               5                   10


<210> SEQ ID NO 8
<211> LENGTH: 8
<212> TYPE: PRT
<213> ORGANISM: Artificial Sequence
<220> FEATURE:
<223> OTHER INFORMATION: synthesized_NP1-CDR-L2

<400> SEQUENCE: 8

Ser Gly Ala Thr Trp Leu Tyr Ser
1               5


<210> SEQ ID NO 9
<211> LENGTH: 9
<212> TYPE: PRT
<213> ORGANISM: Artificial Sequence
<220> FEATURE:
<223> OTHER INFORMATION: synthesized_NP1-CDR-L3

<400> SEQUENCE: 9

Gln Gln Tyr Phe Ser Trp Pro Ile Thr
1               5


<210> SEQ ID NO 10
<211> LENGTH: 13
<212> TYPE: PRT
<213> ORGANISM: Artificial Sequence
<220> FEATURE:
<223> OTHER INFORMATION: synthesized_NP1-CDR-H1

<400> SEQUENCE: 10

Ala Ala Ser Gly Phe Thr Ile Asn Gly Gly Trp Ile His
1               5                   10


<210> SEQ ID NO 11
<211> LENGTH: 11
<212> TYPE: PRT
<213> ORGANISM: Artificial Sequence
<220> FEATURE:
<223> OTHER INFORMATION: synthesized_NP1-CDR-H2

<400> SEQUENCE: 11

Ser Ile Trp Pro Ser Gly Gly Ser Thr Tyr Tyr
1               5                   10


<210> SEQ ID NO 12
<211> LENGTH: 7
<212> TYPE: PRT
<213> ORGANISM: Artificial Sequence
<220> FEATURE:
<223> OTHER INFORMATION: synthesized_NP1-CDR-H3

<400> SEQUENCE: 12

Ala Arg Trp Ser Ser Asp Tyr
1               5


<210> SEQ ID NO 13
<211> LENGTH: 11
<212> TYPE: PRT
<213> ORGANISM: Artificial Sequence
<220> FEATURE:
```

<223> OTHER INFORMATION: synthesized_NP2-CDR-L1

<400> SEQUENCE: 13

Arg Ala Ser Gln Asp Val Tyr Gly Tyr Val Ala
1 5 10

<210> SEQ ID NO 14
<211> LENGTH: 8
<212> TYPE: PRT
<213> ORGANISM: Artificial Sequence
<220> FEATURE:
<223> OTHER INFORMATION: synthesized_NP2-CDR-L2

<400> SEQUENCE: 14

Tyr Gly Ala Ala Gly Leu Tyr Ser
1 5

<210> SEQ ID NO 15
<211> LENGTH: 9
<212> TYPE: PRT
<213> ORGANISM: Artificial Sequence
<220> FEATURE:
<223> OTHER INFORMATION: synthesized_NP2-CDR-L3

<400> SEQUENCE: 15

Gln Gln Tyr Ser Asn Phe Pro Leu Thr
1 5

<210> SEQ ID NO 16
<211> LENGTH: 13
<212> TYPE: PRT
<213> ORGANISM: Artificial Sequence
<220> FEATURE:
<223> OTHER INFORMATION: synthesized_NP2-CDR-H1

<400> SEQUENCE: 16

Ala Ala Ser Gly Phe Thr Ile Gly Gly Gly Gly Ile His
1 5 10

<210> SEQ ID NO 17
<211> LENGTH: 11
<212> TYPE: PRT
<213> ORGANISM: Artificial Sequence
<220> FEATURE:
<223> OTHER INFORMATION: synthesized_NP2-CDR-H2

<400> SEQUENCE: 17

Gly Ile Trp Pro Tyr Trp Gly Tyr Thr Phe Tyr
1 5 10

<210> SEQ ID NO 18
<211> LENGTH: 13
<212> TYPE: PRT
<213> ORGANISM: Artificial Sequence
<220> FEATURE:
<223> OTHER INFORMATION: synthesized_NP2-CDR-H3

<400> SEQUENCE: 18

Ala Arg Phe Trp His Gly Asn Leu Asp Val Met Asp Tyr
1 5 10

<210> SEQ ID NO 19
<211> LENGTH: 11
<212> TYPE: PRT
<213> ORGANISM: Artificial Sequence
<220> FEATURE:
<223> OTHER INFORMATION: synthesized_NP3-CDR-L1

```
<400> SEQUENCE: 19

Arg Ala Ser Gln Asp Val Gly Trp Tyr Val Ala
1               5                   10


<210> SEQ ID NO 20
<211> LENGTH: 7
<212> TYPE: PRT
<213> ORGANISM: Artificial Sequence
<220> FEATURE:
<223> OTHER INFORMATION: synthesized_NP3-CDR-L2

<400> SEQUENCE: 20

Ser Thr Thr Gly Leu Tyr Ser
1               5


<210> SEQ ID NO 21
<211> LENGTH: 9
<212> TYPE: PRT
<213> ORGANISM: Artificial Sequence
<220> FEATURE:
<223> OTHER INFORMATION: synthesized_NP3-CDR-L3

<400> SEQUENCE: 21

Gln Gln Tyr Tyr Asn Tyr Pro Ile Thr
1               5


<210> SEQ ID NO 22
<211> LENGTH: 13
<212> TYPE: PRT
<213> ORGANISM: Artificial Sequence
<220> FEATURE:
<223> OTHER INFORMATION: synthesized_NP3-CDR-H1

<400> SEQUENCE: 22

Ala Ala Ser Gly Phe Thr Ile Ser Asn Tyr Gly Ile His
1               5                   10


<210> SEQ ID NO 23
<211> LENGTH: 11
<212> TYPE: PRT
<213> ORGANISM: Artificial Sequence
<220> FEATURE:
<223> OTHER INFORMATION: synthesized_NP3-CDR-H2

<400> SEQUENCE: 23

Gly Ile Trp Pro Phe Gly Gly Phe Thr Ser Tyr
1               5                   10


<210> SEQ ID NO 24
<211> LENGTH: 13
<212> TYPE: PRT
<213> ORGANISM: Artificial Sequence
<220> FEATURE:
<223> OTHER INFORMATION: synthesized_NP3-CDR-H3

<400> SEQUENCE: 24

Ala Arg Phe His Trp Asn Asp His Gly Tyr Met Asp Tyr
1               5                   10


<210> SEQ ID NO 25
<211> LENGTH: 11
<212> TYPE: PRT
<213> ORGANISM: Artificial Sequence
<220> FEATURE:
<223> OTHER INFORMATION: synthesized_NP4-CDR-L1
```

<400> SEQUENCE: 25

Arg Ala Ser Gln Asp Val Gly Trp Gly Val Ala
1               5                   10

<210> SEQ ID NO 26
<211> LENGTH: 8
<212> TYPE: PRT
<213> ORGANISM: Artificial Sequence
<220> FEATURE:
<223> OTHER INFORMATION: synthesized_NP4-CDR-L2

<400> SEQUENCE: 26

Ser Gly Pro Ser Ser Leu Tyr Ser
1               5

<210> SEQ ID NO 27
<211> LENGTH: 9
<212> TYPE: PRT
<213> ORGANISM: Artificial Sequence
<220> FEATURE:
<223> OTHER INFORMATION: synthesized_NP4-CDR-L3

<400> SEQUENCE: 27

Gln Gln Tyr Phe Asn Tyr Pro Ile Thr
1               5

<210> SEQ ID NO 28
<211> LENGTH: 13
<212> TYPE: PRT
<213> ORGANISM: Artificial Sequence
<220> FEATURE:
<223> OTHER INFORMATION: synthesized_NP4-CDR-H1

<400> SEQUENCE: 28

Ala Ala Ser Gly Phe Thr Ile Ser Asn Ser Ser Ile His
1               5                   10

<210> SEQ ID NO 29
<211> LENGTH: 11
<212> TYPE: PRT
<213> ORGANISM: Artificial Sequence
<220> FEATURE:
<223> OTHER INFORMATION: synthesized_NP4-CDR-H2

<400> SEQUENCE: 29

Gly Ile Gly Pro Ser Gly Gly Tyr Thr Phe Tyr
1               5                   10

<210> SEQ ID NO 30
<211> LENGTH: 20
<212> TYPE: PRT
<213> ORGANISM: Artificial Sequence
<220> FEATURE:
<223> OTHER INFORMATION: synthesized_NP4-CDR-H3

<400> SEQUENCE: 30

Ala Arg Phe His Ser His Asn Ser Tyr Tyr Ser Tyr Ser His Tyr Gly
1               5                   10                  15

Tyr Met Asp Tyr
            20

<210> SEQ ID NO 31
<211> LENGTH: 11
<212> TYPE: PRT
<213> ORGANISM: Artificial Sequence
<220> FEATURE:

<223> OTHER INFORMATION: synthesized_NP5-CDR-L1

<400> SEQUENCE: 31

Arg Ala Ser Gln Asp Val Gly Trp Ser Val Ala
1               5                   10

<210> SEQ ID NO 32
<211> LENGTH: 8
<212> TYPE: PRT
<213> ORGANISM: Artificial Sequence
<220> FEATURE:
<223> OTHER INFORMATION: synthesized_NP5-CDR-L2

<400> SEQUENCE: 32

Tyr Gly Ser Arg Trp Leu Tyr Ser
1               5

<210> SEQ ID NO 33
<211> LENGTH: 9
<212> TYPE: PRT
<213> ORGANISM: Artificial Sequence
<220> FEATURE:
<223> OTHER INFORMATION: synthesized_NP5-CDR-L3

<400> SEQUENCE: 33

Gln Gln Gly Tyr Asn Gly Pro Leu Thr
1               5

<210> SEQ ID NO 34
<211> LENGTH: 13
<212> TYPE: PRT
<213> ORGANISM: Artificial Sequence
<220> FEATURE:
<223> OTHER INFORMATION: synthesized_NP5-CDR-H1

<400> SEQUENCE: 34

Ala Ala Ser Gly Phe Thr Ile Ser Asn Gly Ser Ile His
1               5                   10

<210> SEQ ID NO 35
<211> LENGTH: 11
<212> TYPE: PRT
<213> ORGANISM: Artificial Sequence
<220> FEATURE:
<223> OTHER INFORMATION: synthesized_NP5-CDR-H2

<400> SEQUENCE: 35

Gly Ile Trp Pro Ser Gly Gly Ser Thr Ser Tyr
1               5                   10

<210> SEQ ID NO 36
<211> LENGTH: 5
<212> TYPE: PRT
<213> ORGANISM: Artificial Sequence
<220> FEATURE:
<223> OTHER INFORMATION: synthesized_NP5-CDR-H3

<400> SEQUENCE: 36

Ala Arg Trp Asn Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: synthesized_NP6-CDR-L1

<400> SEQUENCE: 37

Arg Ala Ser Gln Asp Val Tyr Phe Gly Val Ala
1 5 10

<210> SEQ ID NO 38
<211> LENGTH: 8
<212> TYPE: PRT
<213> ORGANISM: Artificial Sequence
<220> FEATURE:
<223> OTHER INFORMATION: synthesized_NP6-CDR-L2

<400> SEQUENCE: 38

Tyr Gly Thr Ser Tyr Leu Tyr Ser
1 5

<210> SEQ ID NO 39
<211> LENGTH: 9
<212> TYPE: PRT
<213> ORGANISM: Artificial Sequence
<220> FEATURE:
<223> OTHER INFORMATION: synthesized_NP6-CDR-L3

<400> SEQUENCE: 39

Gln Gln Phe Ser Asn Trp Pro Ile Thr
1 5

<210> SEQ ID NO 40
<211> LENGTH: 13
<212> TYPE: PRT
<213> ORGANISM: Artificial Sequence
<220> FEATURE:
<223> OTHER INFORMATION: synthesized_NP6-CDR-H1

<400> SEQUENCE: 40

Ala Ala Ser Gly Phe Thr Ile Asn Asp Gly Ser Ile His
1 5 10

<210> SEQ ID NO 41
<211> LENGTH: 11
<212> TYPE: PRT
<213> ORGANISM: Artificial Sequence
<220> FEATURE:
<223> OTHER INFORMATION: synthesized_NP6-CDR-H2

<400> SEQUENCE: 41

Gly Ile Gly Pro Phe Gly Gly Phe Thr Tyr Tyr
1 5 10

<210> SEQ ID NO 42
<211> LENGTH: 11
<212> TYPE: PRT
<213> ORGANISM: Artificial Sequence
<220> FEATURE:
<223> OTHER INFORMATION: synthesized_NP6-CDR-H3

<400> SEQUENCE: 42

Ala Arg Ser Gly Tyr Ser Gly Ser Phe Asp Tyr
1 5 10

<210> SEQ ID NO 43
<211> LENGTH: 11
<212> TYPE: PRT
<213> ORGANISM: Artificial Sequence
<220> FEATURE:
<223> OTHER INFORMATION: synthesized_NP7-CDR-L1

<400> SEQUENCE: 43

Arg Ala Ser Gln Asp Val Phe Gly Trp Val Ala
1 5 10

<210> SEQ ID NO 44
<211> LENGTH: 8
<212> TYPE: PRT
<213> ORGANISM: Artificial Sequence
<220> FEATURE:
<223> OTHER INFORMATION: synthesized_NP7-CDR-L2

<400> SEQUENCE: 44

Ser Tyr Ser Ala Ser Leu Tyr Ser
1 5

<210> SEQ ID NO 45
<211> LENGTH: 9
<212> TYPE: PRT
<213> ORGANISM: Artificial Sequence
<220> FEATURE:
<223> OTHER INFORMATION: synthesized_NP7-CDR-L3

<400> SEQUENCE: 45

Gln Gln Tyr Phe Asn Tyr Pro Leu Thr
1 5

<210> SEQ ID NO 46
<211> LENGTH: 13
<212> TYPE: PRT
<213> ORGANISM: Artificial Sequence
<220> FEATURE:
<223> OTHER INFORMATION: synthesized_NP7-CDR-H1

<400> SEQUENCE: 46

Ala Ala Ser Gly Phe Thr Ile Ser Asn Gly Gly Ile His
1 5 10

<210> SEQ ID NO 47
<211> LENGTH: 11
<212> TYPE: PRT
<213> ORGANISM: Artificial Sequence
<220> FEATURE:
<223> OTHER INFORMATION: synthesized_NP7-CDR-H2

<400> SEQUENCE: 47

Gly Ile Gly Pro Tyr Gly Gly Phe Thr Ser Tyr
1 5 10

<210> SEQ ID NO 48
<211> LENGTH: 16
<212> TYPE: PRT
<213> ORGANISM: Artificial Sequence
<220> FEATURE:
<223> OTHER INFORMATION: synthesized_NP7-CDR-H3

<400> SEQUENCE: 48

Ala Arg Phe Tyr Ser Asn Tyr Tyr Gly Tyr His Gly Val Met Asp Tyr
1 5 10 15

<210> SEQ ID NO 49
<211> LENGTH: 11
<212> TYPE: PRT
<213> ORGANISM: Artificial Sequence
<220> FEATURE:
<223> OTHER INFORMATION: synthesized_NP8-CDR-L1

<400> SEQUENCE: 49

Arg Ala Ser Gln Asp Val Asp Asp Ser Val Ala
1 5 10

<210> SEQ ID NO 50
<211> LENGTH: 8
<212> TYPE: PRT
<213> ORGANISM: Artificial Sequence
<220> FEATURE:
<223> OTHER INFORMATION: synthesized_NP8-CDR-L2

<400> SEQUENCE: 50

Tyr Trp Thr Arg Tyr Leu Tyr Ser
1 5

<210> SEQ ID NO 51
<211> LENGTH: 9
<212> TYPE: PRT
<213> ORGANISM: Artificial Sequence
<220> FEATURE:
<223> OTHER INFORMATION: synthesized_NP8-CDR-L3

<400> SEQUENCE: 51

Gln Gln Gly Tyr Asn Tyr Pro Leu Thr
1 5

<210> SEQ ID NO 52
<211> LENGTH: 13
<212> TYPE: PRT
<213> ORGANISM: Artificial Sequence
<220> FEATURE:
<223> OTHER INFORMATION: synthesized_NP8-CDR-H1

<400> SEQUENCE: 52

Ala Ala Ser Gly Phe Thr Ile Asn Ser Phe Gly Ile His
1 5 10

<210> SEQ ID NO 53
<211> LENGTH: 11
<212> TYPE: PRT
<213> ORGANISM: Artificial Sequence
<220> FEATURE:
<223> OTHER INFORMATION: synthesized_NP8-CDR-H2

<400> SEQUENCE: 53

Gly Ile Gly Pro Phe Gly Gly Ser Thr Phe Tyr
1 5 10

<210> SEQ ID NO 54
<211> LENGTH: 9
<212> TYPE: PRT
<213> ORGANISM: Artificial Sequence
<220> FEATURE:
<223> OTHER INFORMATION: synthesized_NP8-CDR-H3

<400> SEQUENCE: 54

Ala Arg Gly Phe Tyr Trp Phe Asp Tyr
1 5

<210> SEQ ID NO 55
<211> LENGTH: 11
<212> TYPE: PRT
<213> ORGANISM: Artificial Sequence
<220> FEATURE:
<223> OTHER INFORMATION: synthesized_NP9-CDR-L1

<400> SEQUENCE: 55

Arg Ala Ser Gln Asp Val Trp Phe Ser Val Ala
1 5 10

<210> SEQ ID NO 56
<211> LENGTH: 8
<212> TYPE: PRT
<213> ORGANISM: Artificial Sequence
<220> FEATURE:
<223> OTHER INFORMATION: synthesized_NP9-CDR-L2

<400> SEQUENCE: 56

Tyr Gly Thr Thr Ser Leu Tyr Ser
1 5

<210> SEQ ID NO 57
<211> LENGTH: 9
<212> TYPE: PRT
<213> ORGANISM: Artificial Sequence
<220> FEATURE:
<223> OTHER INFORMATION: synthesized_NP9-CDR-L3

<400> SEQUENCE: 57

Gln Gln Tyr Phe Asn Tyr Pro Leu Thr
1 5

<210> SEQ ID NO 58
<211> LENGTH: 13
<212> TYPE: PRT
<213> ORGANISM: Artificial Sequence
<220> FEATURE:
<223> OTHER INFORMATION: synthesized_NP9-CDR-H1

<400> SEQUENCE: 58

Ala Ala Ser Gly Phe Thr Ile Asn Asn Gly Trp Ile His
1 5 10

<210> SEQ ID NO 59
<211> LENGTH: 11
<212> TYPE: PRT
<213> ORGANISM: Artificial Sequence
<220> FEATURE:
<223> OTHER INFORMATION: synthesized_NP9-CDR-H2

<400> SEQUENCE: 59

Gly Ile Gly Pro Tyr Trp Gly Phe Thr Ser Tyr
1 5 10

<210> SEQ ID NO 60
<211> LENGTH: 24
<212> TYPE: PRT
<213> ORGANISM: Artificial Sequence
<220> FEATURE:
<223> OTHER INFORMATION: synthesized_NP9-CDR-H3

<400> SEQUENCE: 60

Ala Arg Phe Asp Ser Asp His Asp His His Tyr Ser Tyr Tyr Tyr Tyr
1 5 10 15

Tyr Asp Asn Gly Tyr Met Asp Tyr
20

<210> SEQ ID NO 61
<211> LENGTH: 11
<212> TYPE: PRT
<213> ORGANISM: Artificial Sequence
<220> FEATURE:
<223> OTHER INFORMATION: synthesized_NP10-CDR-L1

<400> SEQUENCE: 61

Arg Ala Ser Gln Asp Val Ser Trp Ser Val Ala
1 5 10

<210> SEQ ID NO 62
<211> LENGTH: 8
<212> TYPE: PRT
<213> ORGANISM: Artificial Sequence
<220> FEATURE:
<223> OTHER INFORMATION: synthesized_NP10-CDR-L2

<400> SEQUENCE: 62

Ser Gly Ser Thr Trp Leu Tyr Ser
1 5

<210> SEQ ID NO 63
<211> LENGTH: 9
<212> TYPE: PRT
<213> ORGANISM: Artificial Sequence
<220> FEATURE:
<223> OTHER INFORMATION: synthesized_NP10-CDR-L3

<400> SEQUENCE: 63

Gln Gln Tyr Ser Asn Ser Pro Ile Thr
1 5

<210> SEQ ID NO 64
<211> LENGTH: 13
<212> TYPE: PRT
<213> ORGANISM: Artificial Sequence
<220> FEATURE:
<223> OTHER INFORMATION: synthesized_NP10-CDR-H1

<400> SEQUENCE: 64

Ala Ala Ser Gly Phe Thr Ile Asp Asn Gly Ser Ile His
1 5 10

<210> SEQ ID NO 65
<211> LENGTH: 11
<212> TYPE: PRT
<213> ORGANISM: Artificial Sequence
<220> FEATURE:
<223> OTHER INFORMATION: synthesized_NP10-CDR-H2

<400> SEQUENCE: 65

Trp Ile Trp Pro Phe Gly Gly Ser Thr Ser Tyr
1 5 10

<210> SEQ ID NO 66
<211> LENGTH: 10
<212> TYPE: PRT
<213> ORGANISM: Artificial Sequence
<220> FEATURE:
<223> OTHER INFORMATION: synthesized_NP10-CDR-H3

<400> SEQUENCE: 66

Ala Arg Ser Trp Ser Ser Gly Tyr Asp Tyr
1 5 10

<210> SEQ ID NO 67
<211> LENGTH: 11
<212> TYPE: PRT
<213> ORGANISM: Artificial Sequence
<220> FEATURE:
<223> OTHER INFORMATION: synthesized_NP11-CDR-L1

<400> SEQUENCE: 67

```
Arg Ala Ser Gln Asp Val Ser Ser Trp Val Ala
1               5                   10


<210> SEQ ID NO 68
<211> LENGTH: 8
<212> TYPE: PRT
<213> ORGANISM: Artificial Sequence
<220> FEATURE:
<223> OTHER INFORMATION: synthesized_NP11-CDR-L2

<400> SEQUENCE: 68

Ser Trp Ser Gly Tyr Leu Tyr Ser
1               5


<210> SEQ ID NO 69
<211> LENGTH: 9
<212> TYPE: PRT
<213> ORGANISM: Artificial Sequence
<220> FEATURE:
<223> OTHER INFORMATION: synthesized_NP11-CDR-L3

<400> SEQUENCE: 69

Gln Gln Gly Phe Asn Tyr Pro Leu Thr
1               5


<210> SEQ ID NO 70
<211> LENGTH: 13
<212> TYPE: PRT
<213> ORGANISM: Artificial Sequence
<220> FEATURE:
<223> OTHER INFORMATION: synthesized_NP11-CDR-H1

<400> SEQUENCE: 70

Ala Ala Ser Gly Phe Thr Ile Asp Ser Tyr Gly Ile His
1               5                   10


<210> SEQ ID NO 71
<211> LENGTH: 11
<212> TYPE: PRT
<213> ORGANISM: Artificial Sequence
<220> FEATURE:
<223> OTHER INFORMATION: synthesized_NP11-CDR-H2

<400> SEQUENCE: 71

Trp Ile Gly Pro Ser Gly Gly Ser Thr Phe Tyr
1               5                   10


<210> SEQ ID NO 72
<211> LENGTH: 10
<212> TYPE: PRT
<213> ORGANISM: Artificial Sequence
<220> FEATURE:
<223> OTHER INFORMATION: synthesized_NP11-CDR-H3

<400> SEQUENCE: 72

Ala Arg Gly Tyr Phe Trp Phe Phe Asp Tyr
1               5                   10


<210> SEQ ID NO 73
<211> LENGTH: 11
<212> TYPE: PRT
<213> ORGANISM: Artificial Sequence
<220> FEATURE:
<223> OTHER INFORMATION: synthesized_NP12-CDR-L1

<400> SEQUENCE: 73
```

```
Arg Ala Ser Gln Asp Val Gly Gly Asn Val Ala
1               5                   10


<210> SEQ ID NO 74
<211> LENGTH: 8
<212> TYPE: PRT
<213> ORGANISM: Artificial Sequence
<220> FEATURE:
<223> OTHER INFORMATION: synthesized_NP12-CDR-L2

<400> SEQUENCE: 74

Ser Ser Thr Ala Gly Leu Tyr Ser
1               5


<210> SEQ ID NO 75
<211> LENGTH: 9
<212> TYPE: PRT
<213> ORGANISM: Artificial Sequence
<220> FEATURE:
<223> OTHER INFORMATION: synthesized_NP12-CDR-L3

<400> SEQUENCE: 75

Gln Gln Tyr Tyr Asp Phe Pro Leu Thr
1               5


<210> SEQ ID NO 76
<211> LENGTH: 13
<212> TYPE: PRT
<213> ORGANISM: Artificial Sequence
<220> FEATURE:
<223> OTHER INFORMATION: synthesized_NP12-CDR-H1

<400> SEQUENCE: 76

Ala Ala Ser Gly Phe Thr Ile Asp Asn Gly Tyr Ile His
1               5                   10


<210> SEQ ID NO 77
<211> LENGTH: 11
<212> TYPE: PRT
<213> ORGANISM: Artificial Sequence
<220> FEATURE:
<223> OTHER INFORMATION: synthesized_NP12-CDR-H2

<400> SEQUENCE: 77

Ser Ile Trp Pro Ser Trp Gly Ser Thr Tyr Tyr
1               5                   10


<210> SEQ ID NO 78
<211> LENGTH: 10
<212> TYPE: PRT
<213> ORGANISM: Artificial Sequence
<220> FEATURE:
<223> OTHER INFORMATION: synthesized_NP12-CDR-H3

<400> SEQUENCE: 78

Ala Arg Gly Phe Tyr Tyr Tyr Gly Asp Tyr
1               5                   10


<210> SEQ ID NO 79
<211> LENGTH: 11
<212> TYPE: PRT
<213> ORGANISM: Artificial Sequence
<220> FEATURE:
<223> OTHER INFORMATION: synthesized_NP13-CDR-L1

<400> SEQUENCE: 79

Arg Ala Ser Gln Asp Val Gly Tyr Trp Val Ala
```

1 5 10

<210> SEQ ID NO 80
<211> LENGTH: 8
<212> TYPE: PRT
<213> ORGANISM: Artificial Sequence
<220> FEATURE:
<223> OTHER INFORMATION: synthesized_NP13-CDR-L2

<400> SEQUENCE: 80

Ser Ser Ala Ser Gly Leu Tyr Ser
1 5

<210> SEQ ID NO 81
<211> LENGTH: 9
<212> TYPE: PRT
<213> ORGANISM: Artificial Sequence
<220> FEATURE:
<223> OTHER INFORMATION: synthesized_NP13-CDR-L3

<400> SEQUENCE: 81

Gln Gln Gly Trp Asp Trp Pro Ile Thr
1 5

<210> SEQ ID NO 82
<211> LENGTH: 13
<212> TYPE: PRT
<213> ORGANISM: Artificial Sequence
<220> FEATURE:
<223> OTHER INFORMATION: synthesized_NP13-CDR-H1

<400> SEQUENCE: 82

Ala Ala Ser Gly Phe Thr Ile Asn Asn Tyr Gly Ile His
1 5 10

<210> SEQ ID NO 83
<211> LENGTH: 11
<212> TYPE: PRT
<213> ORGANISM: Artificial Sequence
<220> FEATURE:
<223> OTHER INFORMATION: synthesized_NP13-CDR-H2

<400> SEQUENCE: 83

Ser Ile Gly Pro Tyr Gly Gly Ser Thr Tyr Tyr
1 5 10

<210> SEQ ID NO 84
<211> LENGTH: 13
<212> TYPE: PRT
<213> ORGANISM: Artificial Sequence
<220> FEATURE:
<223> OTHER INFORMATION: synthesized_NP13-CDR-H3

<400> SEQUENCE: 84

Ala Arg Phe Gly Tyr Phe Asn Trp Leu Asp Met Asp Tyr
1 5 10

<210> SEQ ID NO 85
<211> LENGTH: 11
<212> TYPE: PRT
<213> ORGANISM: Artificial Sequence
<220> FEATURE:
<223> OTHER INFORMATION: synthesized_NP14-CDR-L1

<400> SEQUENCE: 85

Arg Ala Ser Gln Asp Val Asp Asn Asp Val Ala
1 5 10

<210> SEQ ID NO 86
<211> LENGTH: 8
<212> TYPE: PRT
<213> ORGANISM: Artificial Sequence
<220> FEATURE:
<223> OTHER INFORMATION: synthesized_NP14-CDR-L2

<400> SEQUENCE: 86

Tyr Gly Pro Arg Gly Leu Tyr Ser
1 5

<210> SEQ ID NO 87
<211> LENGTH: 9
<212> TYPE: PRT
<213> ORGANISM: Artificial Sequence
<220> FEATURE:
<223> OTHER INFORMATION: synthesized_NP14-CDR-L3

<400> SEQUENCE: 87

Gln Gln Tyr Ser Ser Trp Pro Leu Thr
1 5

<210> SEQ ID NO 88
<211> LENGTH: 13
<212> TYPE: PRT
<213> ORGANISM: Artificial Sequence
<220> FEATURE:
<223> OTHER INFORMATION: synthesized_NP14-CDR-H1

<400> SEQUENCE: 88

Ala Ala Ser Gly Phe Thr Ile Asp Asn Gly Gly Ile His
1 5 10

<210> SEQ ID NO 89
<211> LENGTH: 11
<212> TYPE: PRT
<213> ORGANISM: Artificial Sequence
<220> FEATURE:
<223> OTHER INFORMATION: synthesized_NP14-CDR-H2

<400> SEQUENCE: 89

Ser Ile Trp Pro Ser Trp Gly Ser Thr Ser Tyr
1 5 10

<210> SEQ ID NO 90
<211> LENGTH: 13
<212> TYPE: PRT
<213> ORGANISM: Artificial Sequence
<220> FEATURE:
<223> OTHER INFORMATION: synthesized_NP14-CDR-H3

<400> SEQUENCE: 90

Ala Arg Phe Asn Phe Gly Val Phe Gly Val Met Asp Tyr
1 5 10

<210> SEQ ID NO 91
<211> LENGTH: 11
<212> TYPE: PRT
<213> ORGANISM: Artificial Sequence
<220> FEATURE:
<223> OTHER INFORMATION: synthesized_NP15-CDR-L1

<400> SEQUENCE: 91

Arg Ala Ser Gln Asp Val Asp Asn Asn Val Ala
1 5 10

<210> SEQ ID NO 92
<211> LENGTH: 8
<212> TYPE: PRT
<213> ORGANISM: Artificial Sequence
<220> FEATURE:
<223> OTHER INFORMATION: synthesized_NP15-CDR-L2

<400> SEQUENCE: 92

Ser Tyr Ser Thr Gly Leu Tyr Ser
1               5

<210> SEQ ID NO 93
<211> LENGTH: 9
<212> TYPE: PRT
<213> ORGANISM: Artificial Sequence
<220> FEATURE:
<223> OTHER INFORMATION: synthesized_NP15-CDR-L3

<400> SEQUENCE: 93

Gln Gln Tyr Trp Asn Tyr Pro Ile Thr
1               5

<210> SEQ ID NO 94
<211> LENGTH: 13
<212> TYPE: PRT
<213> ORGANISM: Artificial Sequence
<220> FEATURE:
<223> OTHER INFORMATION: synthesized_NP15-CDR-H1

<400> SEQUENCE: 94

Ala Ala Ser Gly Phe Thr Ile Ser Asn Trp Tyr Ile His
1               5                   10

<210> SEQ ID NO 95
<211> LENGTH: 11
<212> TYPE: PRT
<213> ORGANISM: Artificial Sequence
<220> FEATURE:
<223> OTHER INFORMATION: synthesized_NP15-CDR-H2

<400> SEQUENCE: 95

Gly Ile Gly Pro Tyr Gly Gly Ser Thr Tyr Tyr
1               5                   10

<210> SEQ ID NO 96
<211> LENGTH: 13
<212> TYPE: PRT
<213> ORGANISM: Artificial Sequence
<220> FEATURE:
<223> OTHER INFORMATION: synthesized_NP15-CDR-H3

<400> SEQUENCE: 96

Ala Arg Phe His Trp Asp His Leu His Gly Met Asp Tyr
1               5                   10

<210> SEQ ID NO 97
<211> LENGTH: 11
<212> TYPE: PRT
<213> ORGANISM: Artificial Sequence
<220> FEATURE:
<223> OTHER INFORMATION: synthesized_NP16-CDR-L1

<400> SEQUENCE: 97

Arg Ala Ser Gln Asp Val Gly Ser Tyr Val Ala
1               5                   10

<210> SEQ ID NO 98
<211> LENGTH: 8
<212> TYPE: PRT
<213> ORGANISM: Artificial Sequence
<220> FEATURE:
<223> OTHER INFORMATION: synthesized_NP16-CDR-L2

<400> SEQUENCE: 98

Ser Trp Thr Thr Gly Leu Tyr Ser
1               5

<210> SEQ ID NO 99
<211> LENGTH: 9
<212> TYPE: PRT
<213> ORGANISM: Artificial Sequence
<220> FEATURE:
<223> OTHER INFORMATION: synthesized_NP16-CDR-L3

<400> SEQUENCE: 99

Gln Gln Tyr Phe Ser Tyr Pro Val Thr
1               5

<210> SEQ ID NO 100
<211> LENGTH: 13
<212> TYPE: PRT
<213> ORGANISM: Artificial Sequence
<220> FEATURE:
<223> OTHER INFORMATION: synthesized_NP16-CDR-H1

<400> SEQUENCE: 100

Ala Ala Ser Gly Phe Thr Ile Gly Asn Ser Gly Ile His
1               5                   10

<210> SEQ ID NO 101
<211> LENGTH: 11
<212> TYPE: PRT
<213> ORGANISM: Artificial Sequence
<220> FEATURE:
<223> OTHER INFORMATION: synthesized_NP16-CDR-H2

<400> SEQUENCE: 101

Trp Ile Gly Pro Tyr Trp Gly Phe Thr Ser Tyr
1               5                   10

<210> SEQ ID NO 102
<211> LENGTH: 13
<212> TYPE: PRT
<213> ORGANISM: Artificial Sequence
<220> FEATURE:
<223> OTHER INFORMATION: synthesized_NP16-CDR-H3

<400> SEQUENCE: 102

Ala Arg Phe Gly Asn His Trp His Leu Phe Met Asp Tyr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: synthesized_NP17-CDR-L1

<400> SEQUENCE: 103

Arg Ala Ser Gln Asp Val Gly Tyr Ser Val Ala
1               5                   10

<210> SEQ ID NO 104

<211> LENGTH: 8
<212> TYPE: PRT
<213> ORGANISM: Artificial Sequence
<220> FEATURE:
<223> OTHER INFORMATION: synthesized_NP17-CDR-L2

<400> SEQUENCE: 104

Ser Ser Pro Gly Gly Leu Tyr Ser
1 5

<210> SEQ ID NO 105
<211> LENGTH: 9
<212> TYPE: PRT
<213> ORGANISM: Artificial Sequence
<220> FEATURE:
<223> OTHER INFORMATION: synthesized_NP17-CDR-L3

<400> SEQUENCE: 105

Gln Gln Tyr Tyr Asp Tyr Pro Val Thr
1 5

<210> SEQ ID NO 106
<211> LENGTH: 13
<212> TYPE: PRT
<213> ORGANISM: Artificial Sequence
<220> FEATURE:
<223> OTHER INFORMATION: synthesized_NP17-CDR-H1

<400> SEQUENCE: 106

Ala Ala Ser Gly Phe Thr Ile Ser Gly Gly Ser Ile His
1 5 10

<210> SEQ ID NO 107
<211> LENGTH: 11
<212> TYPE: PRT
<213> ORGANISM: Artificial Sequence
<220> FEATURE:
<223> OTHER INFORMATION: synthesized_NP17-CDR-H2

<400> SEQUENCE: 107

Ser Ile Trp Pro Phe Gly Gly Ser Thr Phe Tyr
1 5 10

<210> SEQ ID NO 108
<211> LENGTH: 13
<212> TYPE: PRT
<213> ORGANISM: Artificial Sequence
<220> FEATURE:
<223> OTHER INFORMATION: synthesized_NP17-CDR-H3

<400> SEQUENCE: 108

Ala Arg Phe Gly His Gly His Asn Val Ile Met Asp Tyr
1 5 10

<210> SEQ ID NO 109
<211> LENGTH: 11
<212> TYPE: PRT
<213> ORGANISM: Artificial Sequence
<220> FEATURE:
<223> OTHER INFORMATION: synthesized_NP18-CDR-L1

<400> SEQUENCE: 109

Arg Ala Ser Gln Asp Val Gly Tyr Tyr Val Ala
1 5 10

<210> SEQ ID NO 110
<211> LENGTH: 8

<212> TYPE: PRT
<213> ORGANISM: Artificial Sequence
<220> FEATURE:
<223> OTHER INFORMATION: synthesized_NP18-CDR-L2

<400> SEQUENCE: 110

Tyr Gly Pro Arg Phe Leu Tyr Ser
1               5

<210> SEQ ID NO 111
<211> LENGTH: 9
<212> TYPE: PRT
<213> ORGANISM: Artificial Sequence
<220> FEATURE:
<223> OTHER INFORMATION: synthesized_NP18-CDR-L3

<400> SEQUENCE: 111

Gln Gln Tyr Ser Asn Trp Pro Ile Thr
1               5

<210> SEQ ID NO 112
<211> LENGTH: 13
<212> TYPE: PRT
<213> ORGANISM: Artificial Sequence
<220> FEATURE:
<223> OTHER INFORMATION: synthesized_NP18-CDR-H1

<400> SEQUENCE: 112

Ala Ala Ser Gly Phe Thr Ile Ser Gly Gly Gly Ile His
1               5                   10

<210> SEQ ID NO 113
<211> LENGTH: 11
<212> TYPE: PRT
<213> ORGANISM: Artificial Sequence
<220> FEATURE:
<223> OTHER INFORMATION: synthesized_NP18-CDR-H2

<400> SEQUENCE: 113

Ser Ile Trp Pro Ser Trp Gly Ser Thr Ser Tyr
1               5                   10

<210> SEQ ID NO 114
<211> LENGTH: 13
<212> TYPE: PRT
<213> ORGANISM: Artificial Sequence
<220> FEATURE:
<223> OTHER INFORMATION: synthesized_NP18-CDR-H3

<400> SEQUENCE: 114

Ala Arg Phe His Asn Gly Gly Phe Leu Val Met Asp Tyr
1               5                   10

<210> SEQ ID NO 115
<211> LENGTH: 11
<212> TYPE: PRT
<213> ORGANISM: Artificial Sequence
<220> FEATURE:
<223> OTHER INFORMATION: synthesized_NP19-CDR-L1

<400> SEQUENCE: 115

Arg Ala Ser Gln Asp Val Ser Gly Trp Val Ala
1               5                   10

<210> SEQ ID NO 116
<211> LENGTH: 8
<212> TYPE: PRT

<213> ORGANISM: Artificial Sequence
<220> FEATURE:
<223> OTHER INFORMATION: synthesized_NP19-CDR-L2

<400> SEQUENCE: 116

Ser Trp Ser Thr Gly Leu Tyr Ser
1               5

<210> SEQ ID NO 117
<211> LENGTH: 9
<212> TYPE: PRT
<213> ORGANISM: Artificial Sequence
<220> FEATURE:
<223> OTHER INFORMATION: synthesized_NP19-CDR-L3

<400> SEQUENCE: 117

Gln Gln Tyr Phe Asn Phe Pro Val Thr
1               5

<210> SEQ ID NO 118
<211> LENGTH: 13
<212> TYPE: PRT
<213> ORGANISM: Artificial Sequence
<220> FEATURE:
<223> OTHER INFORMATION: synthesized_NP19-CDR-H1

<400> SEQUENCE: 118

Ala Ala Ser Gly Phe Thr Ile Ser Ser Trp Gly Ile His
1               5                   10

<210> SEQ ID NO 119
<211> LENGTH: 11
<212> TYPE: PRT
<213> ORGANISM: Artificial Sequence
<220> FEATURE:
<223> OTHER INFORMATION: synthesized_NP19-CDR-H2

<400> SEQUENCE: 119

Gly Ile Gly Pro Phe Trp Gly Tyr Thr Ser Tyr
1               5                   10

<210> SEQ ID NO 120
<211> LENGTH: 13
<212> TYPE: PRT
<213> ORGANISM: Artificial Sequence
<220> FEATURE:
<223> OTHER INFORMATION: synthesized_NP19-CDR-H3

<400> SEQUENCE: 120

Ala Arg Phe Gly Val Asp Asn Tyr Gly Tyr Met Asp Tyr
1               5                   10

<210> SEQ ID NO 121
<211> LENGTH: 11
<212> TYPE: PRT
<213> ORGANISM: Artificial Sequence
<220> FEATURE:
<223> OTHER INFORMATION: synthesized_NP20-CDR-L1

<400> SEQUENCE: 121

Arg Ala Ser Gln Asp Val Gly Tyr Gly Val Ala
1               5                   10

<210> SEQ ID NO 122
<211> LENGTH: 8
<212> TYPE: PRT
<213> ORGANISM: Artificial Sequence
<220> FEATURE:
<223> OTHER INFORMATION: synthesized_NP20-CDR-L2

<400> SEQUENCE: 122

Ser Gly Ala Ser Gly Leu Tyr Ser
1               5

<210> SEQ ID NO 123
<211> LENGTH: 9
<212> TYPE: PRT
<213> ORGANISM: Artificial Sequence
<220> FEATURE:
<223> OTHER INFORMATION: synthesized_NP20-CDR-L3

<400> SEQUENCE: 123

Gln Gln Tyr Ser Ser Phe Pro Leu Thr
1               5

<210> SEQ ID NO 124
<211> LENGTH: 13
<212> TYPE: PRT
<213> ORGANISM: Artificial Sequence
<220> FEATURE:
<223> OTHER INFORMATION: synthesized_NP20-CDR-H1

<400> SEQUENCE: 124

Ala Ala Ser Gly Phe Thr Ile Asn Gly Tyr Ser Ile His
1               5                   10

<210> SEQ ID NO 125
<211> LENGTH: 11
<212> TYPE: PRT
<213> ORGANISM: Artificial Sequence
<220> FEATURE:
<223> OTHER INFORMATION: synthesized_NP20-CDR-H2

<400> SEQUENCE: 125

Ser Ile Gly Pro Tyr Gly Gly Phe Thr Tyr Tyr
1               5                   10

<210> SEQ ID NO 126
<211> LENGTH: 7
<212> TYPE: PRT
<213> ORGANISM: Artificial Sequence
<220> FEATURE:
<223> OTHER INFORMATION: synthesized_NP20-CDR-H3

<400> SEQUENCE: 126

Ala Gly Phe Gly Phe Tyr Tyr
1               5

<210> SEQ ID NO 127
<211> LENGTH: 11
<212> TYPE: PRT
<213> ORGANISM: Artificial Sequence
<220> FEATURE:
<223> OTHER INFORMATION: synthesized_NP21-CDR-L1

<400> SEQUENCE: 127

Arg Ala Ser Gln Asp Val Tyr Phe Tyr Val Ala
1               5                   10

<210> SEQ ID NO 128
<211> LENGTH: 8
<212> TYPE: PRT
<213> ORGANISM: Artificial Sequence
<220> FEATURE:

<223> OTHER INFORMATION: synthesized_NP21-CDR-L2

<400> SEQUENCE: 128

Tyr Gly Ser Arg Trp Leu Tyr Ser
1               5

<210> SEQ ID NO 129
<211> LENGTH: 9
<212> TYPE: PRT
<213> ORGANISM: Artificial Sequence
<220> FEATURE:
<223> OTHER INFORMATION: synthesized_NP21-CDR-L3

<400> SEQUENCE: 129

Gln Gln Tyr Ser Asn Phe Pro Val Thr
1               5

<210> SEQ ID NO 130
<211> LENGTH: 13
<212> TYPE: PRT
<213> ORGANISM: Artificial Sequence
<220> FEATURE:
<223> OTHER INFORMATION: synthesized_NP21-CDR-H1

<400> SEQUENCE: 130

Ala Ala Ser Gly Phe Thr Ile Asn Gly Tyr Gly Ile His
1               5                   10

<210> SEQ ID NO 131
<211> LENGTH: 11
<212> TYPE: PRT
<213> ORGANISM: Artificial Sequence
<220> FEATURE:
<223> OTHER INFORMATION: synthesized_NP21-CDR-H2

<400> SEQUENCE: 131

Gly Ile Trp Pro Tyr Gly Gly Ser Thr Phe Tyr
1               5                   10

<210> SEQ ID NO 132
<211> LENGTH: 13
<212> TYPE: PRT
<213> ORGANISM: Artificial Sequence
<220> FEATURE:
<223> OTHER INFORMATION: synthesized_NP21-CDR-H3

<400> SEQUENCE: 132

Ala Arg Phe Tyr Asn Asn His Gly Gly Ile Met Asp Tyr
1               5                   10

<210> SEQ ID NO 133
<211> LENGTH: 11
<212> TYPE: PRT
<213> ORGANISM: Artificial Sequence
<220> FEATURE:
<223> OTHER INFORMATION: synthesized_NP22-CDR-L1

<400> SEQUENCE: 133

Arg Ala Ser Gln Asp Val Phe Ser Trp Val Ala
1               5                   10

<210> SEQ ID NO 134
<211> LENGTH: 8
<212> TYPE: PRT
<213> ORGANISM: Artificial Sequence
<220> FEATURE:
<223> OTHER INFORMATION: synthesized_NP22-CDR-L2

<400> SEQUENCE: 134

Ser Ser Ala Ser Ser Leu Tyr Ser
1 5

<210> SEQ ID NO 135
<211> LENGTH: 9
<212> TYPE: PRT
<213> ORGANISM: Artificial Sequence
<220> FEATURE:
<223> OTHER INFORMATION: synthesized_NP22-CDR-L3

<400> SEQUENCE: 135

Gln Gln Ser Trp Asp Tyr Pro Ile Thr
1 5

<210> SEQ ID NO 136
<211> LENGTH: 13
<212> TYPE: PRT
<213> ORGANISM: Artificial Sequence
<220> FEATURE:
<223> OTHER INFORMATION: synthesized_NP22-CDR-H1

<400> SEQUENCE: 136

Ala Ala Ser Gly Phe Thr Ile Ser Asp Trp Ser Ile His
1 5 10

<210> SEQ ID NO 137
<211> LENGTH: 11
<212> TYPE: PRT
<213> ORGANISM: Artificial Sequence
<220> FEATURE:
<223> OTHER INFORMATION: synthesized_NP22-CDR-H2

<400> SEQUENCE: 137

Gly Ile Trp Pro Tyr Trp Gly Ser Thr Ser Tyr
1 5 10

<210> SEQ ID NO 138
<211> LENGTH: 10
<212> TYPE: PRT
<213> ORGANISM: Artificial Sequence
<220> FEATURE:
<223> OTHER INFORMATION: synthesized_NP22-CDR-H3

<400> SEQUENCE: 138

Ala Arg Gly Phe Tyr Ser Trp Phe Asp Tyr
1 5 10

<210> SEQ ID NO 139
<211> LENGTH: 11
<212> TYPE: PRT
<213> ORGANISM: Artificial Sequence
<220> FEATURE:
<223> OTHER INFORMATION: synthesized_NP23-CDR-L1

<400> SEQUENCE: 139

Arg Ala Ser Gln Asp Val Asp Asp Gly Val Ala
1 5 10

<210> SEQ ID NO 140
<211> LENGTH: 8
<212> TYPE: PRT
<213> ORGANISM: Artificial Sequence
<220> FEATURE:
<223> OTHER INFORMATION: synthesized_NP23-CDR-L2

<400> SEQUENCE: 140

Ser Gly Ala Arg Trp Leu Tyr Ser
1 5

<210> SEQ ID NO 141
<211> LENGTH: 9
<212> TYPE: PRT
<213> ORGANISM: Artificial Sequence
<220> FEATURE:
<223> OTHER INFORMATION: synthesized_NP23-CDR-L3

<400> SEQUENCE: 141

Gln Gln Tyr Tyr Asn Phe Pro Leu Thr
1 5

<210> SEQ ID NO 142
<211> LENGTH: 13
<212> TYPE: PRT
<213> ORGANISM: Artificial Sequence
<220> FEATURE:
<223> OTHER INFORMATION: synthesized_NP23-CDR-H1

<400> SEQUENCE: 142

Ala Ala Ser Gly Phe Thr Ile Ser Asn Tyr Phe Ile His
1 5 10

<210> SEQ ID NO 143
<211> LENGTH: 11
<212> TYPE: PRT
<213> ORGANISM: Artificial Sequence
<220> FEATURE:
<223> OTHER INFORMATION: synthesized_NP23-CDR-H2

<400> SEQUENCE: 143

Ser Ile Gly Pro Phe Gly Gly Phe Thr Ser Tyr
1 5 10

<210> SEQ ID NO 144
<211> LENGTH: 7
<212> TYPE: PRT
<213> ORGANISM: Artificial Sequence
<220> FEATURE:
<223> OTHER INFORMATION: synthesized_NP23-CDR-H3

<400> SEQUENCE: 144

Ala Gly Tyr Gly Phe His Tyr
1 5

<210> SEQ ID NO 145
<211> LENGTH: 11
<212> TYPE: PRT
<213> ORGANISM: Artificial Sequence
<220> FEATURE:
<223> OTHER INFORMATION: synthesized_NP24-CDR-L1

<400> SEQUENCE: 145

Arg Ala Ser Gln Asp Val Gly Ser Ser Val Ala
1 5 10

<210> SEQ ID NO 146
<211> LENGTH: 8
<212> TYPE: PRT
<213> ORGANISM: Artificial Sequence
<220> FEATURE:
<223> OTHER INFORMATION: synthesized_NP24-CDR-L2

<400> SEQUENCE: 146

Phe Tyr Thr Ser Ser Leu Tyr Ser
1 5

<210> SEQ ID NO 147
<211> LENGTH: 9
<212> TYPE: PRT
<213> ORGANISM: Artificial Sequence
<220> FEATURE:
<223> OTHER INFORMATION: synthesized_NP24-CDR-L3

<400> SEQUENCE: 147

Gln Gln Gly Trp Asp Ser Pro Val Thr
1 5

<210> SEQ ID NO 148
<211> LENGTH: 13
<212> TYPE: PRT
<213> ORGANISM: Artificial Sequence
<220> FEATURE:
<223> OTHER INFORMATION: synthesized_NP24-CDR-H1

<400> SEQUENCE: 148

Ala Ala Ser Gly Phe Thr Ile Asp Asp Trp Tyr Ile His
1 5 10

<210> SEQ ID NO 149
<211> LENGTH: 11
<212> TYPE: PRT
<213> ORGANISM: Artificial Sequence
<220> FEATURE:
<223> OTHER INFORMATION: synthesized_NP24-CDR-H2

<400> SEQUENCE: 149

Gly Ile Gly Pro Tyr Gly Gly Phe Thr Tyr Tyr
1 5 10

<210> SEQ ID NO 150
<211> LENGTH: 10
<212> TYPE: PRT
<213> ORGANISM: Artificial Sequence
<220> FEATURE:
<223> OTHER INFORMATION: synthesized_NP24-CDR-H3

<400> SEQUENCE: 150

Ala Arg Gly Tyr Tyr Gly Ser Phe Asp Tyr
1 5 10

<210> SEQ ID NO 151
<211> LENGTH: 11
<212> TYPE: PRT
<213> ORGANISM: Artificial Sequence
<220> FEATURE:
<223> OTHER INFORMATION: synthesized_NP25-CDR-L1

<400> SEQUENCE: 151

Arg Ala Gly Gln Asp Val Ser Ser Gly Val Ala
1 5 10

<210> SEQ ID NO 152
<211> LENGTH: 8
<212> TYPE: PRT
<213> ORGANISM: Artificial Sequence
<220> FEATURE:
<223> OTHER INFORMATION: synthesized_NP25-CDR-L2

<400> SEQUENCE: 152

Ser Trp Thr Ser Phe Leu Tyr Ser
1 5

<210> SEQ ID NO 153
<211> LENGTH: 9
<212> TYPE: PRT
<213> ORGANISM: Artificial Sequence
<220> FEATURE:
<223> OTHER INFORMATION: synthesized_NP25-CDR-L3

<400> SEQUENCE: 153

Gln Gln Tyr Tyr Asp Tyr Pro Ile Thr
1 5

<210> SEQ ID NO 154
<211> LENGTH: 13
<212> TYPE: PRT
<213> ORGANISM: Artificial Sequence
<220> FEATURE:
<223> OTHER INFORMATION: synthesized_NP25-CDR-H1

<400> SEQUENCE: 154

Ala Ala Ser Gly Phe Thr Ile Gly Gly Gly Phe Ile His
1 5 10

<210> SEQ ID NO 155
<211> LENGTH: 11
<212> TYPE: PRT
<213> ORGANISM: Artificial Sequence
<220> FEATURE:
<223> OTHER INFORMATION: synthesized_NP25-CDR-H2

<400> SEQUENCE: 155

Ser Ile Trp Pro Tyr Trp Gly Phe Thr Tyr Tyr
1 5 10

<210> SEQ ID NO 156
<211> LENGTH: 10
<212> TYPE: PRT
<213> ORGANISM: Artificial Sequence
<220> FEATURE:
<223> OTHER INFORMATION: synthesized_NP25-CDR-H3

<400> SEQUENCE: 156

Ala Arg Gly Ser Tyr Gly Tyr Ser Asp Tyr
1 5 10

<210> SEQ ID NO 157
<211> LENGTH: 110
<212> TYPE: PRT
<213> ORGANISM: Artificial Sequence
<220> FEATURE:
<223> OTHER INFORMATION: synthesized_NP1-VL

<400> SEQUENCE: 157

Met Ala Asp Ile Gln Met Thr Gln Ser Pro Ser Ser Leu Ser Ala Ser
1 5 10 15

Val Gly Asp Arg Val Thr Ile Thr Cys Arg Ala Ser Gln Asp Val Asp
20 25 30

Asp Asp Val Ala Trp Tyr Gln Gln Lys Pro Gly Lys Ala Pro Lys Leu
35 40 45

Leu Ile Ser Gly Ala Thr Trp Leu Tyr Ser Gly Val Pro Ser Arg Phe
50 55 60

Ser Gly Ser Gly Ser Gly Thr Asp Phe Thr Leu Thr Ile Ser Ser Leu
65 70 75 80

```
Gln Pro Glu Asp Phe Ala Thr Tyr Tyr Cys Gln Gln Tyr Phe Ser Trp
                85                  90                  95

Pro Ile Thr Phe Gly Gln Gly Thr Lys Val Glu Ile Lys Arg
            100                 105                 110


<210> SEQ ID NO 158
<211> LENGTH: 119
<212> TYPE: PRT
<213> ORGANISM: Artificial Sequence
<220> FEATURE:
<223> OTHER INFORMATION: synthesized_NP1-VH

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Gly Gly
            20                  25                  30

Trp Ile His Trp Val Arg Gln Ala Pro Gly Lys Gly Leu Glu Trp Val
        35                  40                  45

Ala Ser Ile Trp Pro Ser Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ser Ser Asp Tyr Trp Gly Gln Gly Thr Leu Val Thr Val
            100                 105                 110

Ser Ser Ala Ser Ala Ala Ala
        115


<210> SEQ ID NO 159
<211> LENGTH: 110
<212> TYPE: PRT
<213> ORGANISM: Artificial Sequence
<220> FEATURE:
<223> OTHER INFORMATION: synthesized_NP2-VL

<400> SEQUENCE: 159

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Tyr
            20                  25                  30

Gly Tyr Val Ala Trp Tyr Gln Gln Lys Pro Gly Lys Ala Pro Lys Leu
        35                  40                  45

Leu Ile Tyr Gly Ala Ala Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Ser Asn Phe
                85                  90                  95

Pro Leu Thr Phe Gly Gln Gly Thr Lys Val Glu Ile Lys Arg
            100                 105                 110


<210> SEQ ID NO 160
<211> LENGTH: 125
<212> TYPE: PRT
<213> ORGANISM: Artificial Sequence
<220> FEATURE:
<223> OTHER INFORMATION: synthesized_NP2-VH
```

<400> SEQUENCE: 160

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Gly Gly
            20                  25                  30

Gly Ile His Trp Val Arg Gln Ala Pro Gly Lys Gly Leu Glu Trp Val
        35                  40                  45

Ala Gly Ile Trp Pro Tyr Trp Gly Tyr Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Trp His Gly Asn Leu Asp Val Met Asp Tyr Trp Gly Gln
            100                 105                 110

Gly Thr Leu Val Thr Val Ser Ser Ala Ser Ala Ala Ala
        115                 120                 125
```

<210> SEQ ID NO 161
<211> LENGTH: 110
<212> TYPE: PRT
<213> ORGANISM: Artificial Sequence
<220> FEATURE:
<223> OTHER INFORMATION: synthesized_NP3-VL

<400> SEQUENCE: 161

```
Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Trp Tyr Val Ala Trp Tyr Gln Gln Lys Pro Gly Lys Ala Pro Lys Leu
        35                  40                  45

Leu Ile Tyr Ser Thr Thr Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Tyr Asn Tyr
                85                  90                  95

Pro Ile Thr Phe Gly Gln Gly Thr Lys Val Glu Ile Lys Arg
            100                 105                 110
```

<210> SEQ ID NO 162
<211> LENGTH: 125
<212> TYPE: PRT
<213> ORGANISM: Artificial Sequence
<220> FEATURE:
<223> OTHER INFORMATION: synthesized_NP3-VH

<400> SEQUENCE: 162

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Tyr
            20                  25                  30

Gly Ile His Trp Val Arg Gln Ala Pro Gly Lys Gly Leu Glu Trp Val
        35                  40                  45

Ala Gly Ile Trp Pro Phe Gly Gly Phe Thr Ser Tyr Ala Asp Ser Val
    50                  55                  60
```

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Trp Asn Asp His Gly Tyr Met Asp Tyr Trp Gly Gln
            100                 105                 110

Gly Thr Leu Val Thr Val Ser Ser Ala Ser Ala Ala Ala
        115                 120                 125


<210> SEQ ID NO 163
<211> LENGTH: 110
<212> TYPE: PRT
<213> ORGANISM: Artificial Sequence
<220> FEATURE:
<223> OTHER INFORMATION: synthesized_NP4-VL

<400> SEQUENCE: 163

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Trp Gly Val Ala Trp Tyr Gln Gln Lys Pro Gly Lys Ala Pro Lys Leu
        35                  40                  45

Leu Ile Ser Gly Pro Ser Ser Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Phe Asn Tyr
                85                  90                  95

Pro Ile Thr Phe Gly Gln Gly Thr Lys Val Glu Ile Lys Arg
            100                 105                 110


<210> SEQ ID NO 164
<211> LENGTH: 132
<212> TYPE: PRT
<213> ORGANISM: Artificial Sequence
<220> FEATURE:
<223> OTHER INFORMATION: synthesized_NP4-VH

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Ser
            20                  25                  30

Ser Ile His Trp Val Arg Gln Ala Pro Gly Lys Gly Leu Glu Trp Val
        35                  40                  45

Ala Gly Ile Gly Pro Ser Gly Gly Tyr Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Ser His Asn Ser Tyr Tyr Ser Tyr Ser His Tyr Gly
            100                 105                 110

Tyr Met Asp Tyr Trp Gly Gln Gly Thr Leu Val Thr Val Ser Ser Ala
        115                 120                 125

Ser Ala Ala Ala
```

130

<210> SEQ ID NO 165
<211> LENGTH: 110
<212> TYPE: PRT
<213> ORGANISM: Artificial Sequence
<220> FEATURE:
<223> OTHER INFORMATION: synthesized_NP5-VL

<400> SEQUENCE: 165

Met Ala Asp Ile Gln Met Thr Gln Ser Pro Ser Ser Leu Ser Ala Ser
1 5 10 15

Val Gly Asp Arg Val Thr Ile Thr Cys Arg Ala Ser Gln Asp Val Gly
20 25 30

Trp Ser Val Ala Trp Tyr Gln Gln Lys Pro Gly Lys Ala Pro Lys Leu
35 40 45

Leu Ile Tyr Gly Ser Arg Trp Leu Tyr Ser Gly Val Pro Ser Arg Phe
50 55 60

Ser Gly Ser Gly Ser Gly Thr Asp Phe Thr Leu Thr Ile Ser Ser Leu
65 70 75 80

Gln Pro Glu Asp Phe Ala Thr Tyr Tyr Cys Gln Gln Gly Tyr Asn Gly
85 90 95

Pro Leu Thr Phe Gly Gln Gly Thr Lys Val Glu Ile Lys Arg
100 105 110

<210> SEQ ID NO 166
<211> LENGTH: 117
<212> TYPE: PRT
<213> ORGANISM: Artificial Sequence
<220> FEATURE:
<223> OTHER INFORMATION: synthesized_NP5-VH

<400> SEQUENCE: 166

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Ile Ser Asn Gly
20 25 30

Ser Ile His Trp Val Arg Gln Ala Pro Gly Lys Gly Leu Glu Trp Val
35 40 45

Ala Gly Ile Trp Pro Ser Gly Gly Ser Thr Ser Tyr Ala Asp Ser Val
50 55 60

Lys Gly Arg Phe Thr Ile Ser Ala Asp Thr Ile Asn Asn Ser Ala Tyr
65 70 75 80

Leu Gln Met Asn Ser Leu Arg Ala Glu Asp Thr Ala Val Tyr Tyr Cys
85 90 95

Ala Arg Trp Asn Tyr Trp Gly Gln Gly Thr Leu Val Thr Val Ser Ser
100 105 110

Ala Ser Ala Ala Ala
115

<210> SEQ ID NO 167
<211> LENGTH: 110
<212> TYPE: PRT
<213> ORGANISM: Artificial Sequence
<220> FEATURE:
<223> OTHER INFORMATION: synthesized_NP6-VL

<400> SEQUENCE: 167

Met Ala Asp Ile Gln Met Thr Gln Ser Pro Ser Ser Leu Ser Ala Ser
1 5 10 15

```
Val Gly Asp Arg Val Thr Ile Thr Cys Arg Ala Ser Gln Asp Val Tyr
            20                  25                  30

Phe Gly Val Ala Trp Tyr Gln Gln Lys Pro Gly Lys Ala Pro Lys Leu
        35                  40                  45

Leu Ile Tyr Gly Thr Ser Tyr Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Phe Ser Asn Trp
                85                  90                  95

Pro Ile Thr Phe Gly Gln Gly Thr Lys Val Glu Ile Lys Arg
            100                 105                 110


<210> SEQ ID NO 168
<211> LENGTH: 123
<212> TYPE: PRT
<213> ORGANISM: Artificial Sequence
<220> FEATURE:
<223> OTHER INFORMATION: synthesized_NP6-VH

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asp Gly
            20                  25                  30

Ser Ile His Trp Val Arg Gln Ala Pro Gly Lys Gly Leu Glu Trp Val
        35                  40                  45

Ala Gly Ile Gly Pro Phe Gly Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Gly Tyr Ser Gly Ser Phe Asp Tyr Trp Gly Gln Gly Thr
            100                 105                 110

Leu Val Thr Val Ser Ser Ala Ser Ala Ala Ala
        115                 120


<210> SEQ ID NO 169
<211> LENGTH: 110
<212> TYPE: PRT
<213> ORGANISM: Artificial Sequence
<220> FEATURE:
<223> OTHER INFORMATION: synthesized_NP7-VL

<400> SEQUENCE: 169

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Phe
            20                  25                  30

Gly Trp Val Ala Trp Tyr Gln Gln Lys Pro Gly Lys Ala Pro Lys Leu
        35                  40                  45

Leu Ile Ser Tyr Ser Ala Ser Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Phe Asn Tyr
```

```
                85                  90                  95

Pro Leu Thr Phe Gly Gln Gly Thr Lys Val Glu Ile Lys Arg
            100                 105                 110


<210> SEQ ID NO 170
<211> LENGTH: 128
<212> TYPE: PRT
<213> ORGANISM: Artificial Sequence
<220> FEATURE:
<223> OTHER INFORMATION: synthesized_NP7-VH

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Gly
            20                  25                  30

Gly Ile His Trp Val Arg Gln Ala Pro Gly Lys Gly Leu Glu Trp Val
        35                  40                  45

Ala Gly Ile Gly Pro Tyr Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Tyr Ser Asn Tyr Tyr Gly Tyr His Gly Val Met Asp Tyr
            100                 105                 110

Trp Gly Gln Gly Thr Leu Val Thr Val Ser Ser Ala Ser Ala Ala Ala
        115                 120                 125


<210> SEQ ID NO 171
<211> LENGTH: 110
<212> TYPE: PRT
<213> ORGANISM: Artificial Sequence
<220> FEATURE:
<223> OTHER INFORMATION: synthesized_NP8-VL

<400> SEQUENCE: 171

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asp
            20                  25                  30

Asp Ser Val Ala Trp Tyr Gln Gln Lys Pro Gly Lys Ala Pro Lys Leu
        35                  40                  45

Leu Ile Tyr Trp Thr Arg Tyr Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Gly Tyr Asn Tyr
                85                  90                  95

Pro Leu Thr Phe Gly Gln Gly Thr Lys Val Glu Ile Lys Arg
            100                 105                 110


<210> SEQ ID NO 172
<211> LENGTH: 121
<212> TYPE: PRT
<213> ORGANISM: Artificial Sequence
<220> FEATURE:
<223> OTHER INFORMATION: synthesized_NP8-VH

<400> SEQUENCE: 172
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Ser Phe
            20                  25                  30

Gly Ile His Trp Val Arg Gln Ala Pro Gly Lys Gly Leu Glu Trp Val
        35                  40                  45

Ala Gly Ile Gly Pro Phe Gly Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Tyr Trp Phe Asp Tyr Trp Gly Gln Gly Thr Leu Val
            100                 105                 110

Thr Val Ser Ser Ala Ser Ala Ala Ala
        115                 120


<210> SEQ ID NO 173
<211> LENGTH: 110
<212> TYPE: PRT
<213> ORGANISM: Artificial Sequence
<220> FEATURE:
<223> OTHER INFORMATION: synthesized_NP9-VL

<400> SEQUENCE: 173

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Trp
            20                  25                  30

Phe Ser Val Ala Trp Tyr Gln Gln Lys Pro Gly Lys Ala Pro Lys Leu
        35                  40                  45

Leu Ile Tyr Gly Thr Thr Ser Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Phe Asn Tyr
                85                  90                  95

Pro Leu Thr Phe Gly Gln Gly Thr Lys Val Glu Ile Lys Arg
            100                 105                 110


<210> SEQ ID NO 174
<211> LENGTH: 136
<212> TYPE: PRT
<213> ORGANISM: Artificial Sequence
<220> FEATURE:
<223> OTHER INFORMATION: synthesized_NP9-VH

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Gly
            20                  25                  30

Trp Ile His Trp Val Arg Gln Ala Pro Gly Lys Gly Leu Glu Trp Val
        35                  40                  45

Ala Gly Ile Gly Pro Tyr Trp Gly Phe Thr Ser Tyr Ala Asp Ser Val
    50                  55                  60

Lys Gly Arg Phe Met Ile Ser Ala Asp Thr Ser Lys Asn Thr Ala Tyr
```

```
65                  70                  75                  80

Leu Gln Met Asn Ser Leu Arg Ala Glu Asp Thr Ala Val Tyr Tyr Cys
                85                  90                  95

Ala Arg Phe Asp Ser Asp His Asp His His Tyr Ser Tyr Tyr Tyr Tyr
            100                 105                 110

Tyr Asp Asn Gly Tyr Met Asp Tyr Trp Gly Gln Gly Thr Leu Val Thr
        115                 120                 125

Val Ser Ser Ala Ser Ala Ala Ala
    130                 135


<210> SEQ ID NO 175
<211> LENGTH: 110
<212> TYPE: PRT
<213> ORGANISM: Artificial Sequence
<220> FEATURE:
<223> OTHER INFORMATION: synthesized_NP10-VL

<400> SEQUENCE: 175

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Ser
            20                  25                  30

Trp Ser Val Ala Trp Tyr Gln Gln Lys Pro Gly Lys Ala Pro Lys Leu
        35                  40                  45

Leu Ile Ser Gly Ser Thr Trp Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Ser Asn Ser
                85                  90                  95

Pro Ile Thr Phe Gly Gln Gly Thr Lys Val Glu Ile Lys Arg
            100                 105                 110


<210> SEQ ID NO 176
<211> LENGTH: 122
<212> TYPE: PRT
<213> ORGANISM: Artificial Sequence
<220> FEATURE:
<223> OTHER INFORMATION: synthesized_NP10-VH

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Gly
            20                  25                  30

Ser Ile His Trp Val Arg Gln Ala Pro Gly Lys Gly Leu Glu Trp Val
        35                  40                  45

Ala Trp Ile Trp Pro Phe Gly Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Trp Ser Ser Gly Tyr Asp Tyr Trp Gly Gln Gly Thr Leu
            100                 105                 110

Val Thr Val Ser Ser Ala Ser Ala Ala Ala
        115                 120
```

<210> SEQ ID NO 177
<211> LENGTH: 110
<212> TYPE: PRT
<213> ORGANISM: Artificial Sequence
<220> FEATURE:
<223> OTHER INFORMATION: synthesized_NP11-VL

<400> SEQUENCE: 177

```
Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Ser
            20                  25                  30

Ser Trp Val Ala Trp Tyr Gln Gln Lys Pro Gly Lys Ala Pro Lys Leu
        35                  40                  45

Leu Ile Ser Trp Ser Gly Tyr Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Gly Phe Asn Tyr
                85                  90                  95

Pro Leu Thr Phe Gly Gln Gly Thr Lys Val Glu Ile Lys Arg
            100                 105                 110
```

<210> SEQ ID NO 178
<211> LENGTH: 122
<212> TYPE: PRT
<213> ORGANISM: Artificial Sequence
<220> FEATURE:
<223> OTHER INFORMATION: synthesized_NP11-VH

<400> SEQUENCE: 178

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Ser Tyr
            20                  25                  30

Gly Ile His Trp Val Arg Gln Ala Pro Gly Lys Gly Leu Glu Trp Val
        35                  40                  45

Ala Trp Ile Gly Pro Ser Gly Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Phe Trp Phe Phe Asp Tyr Trp Gly Gln Gly Thr Leu
            100                 105                 110

Val Thr Val Ser Ser Ala Ser Ala Ala Ala
        115                 120
```

<210> SEQ ID NO 179
<211> LENGTH: 110
<212> TYPE: PRT
<213> ORGANISM: Artificial Sequence
<220> FEATURE:
<223> OTHER INFORMATION: synthesized_NP12-VL

<400> SEQUENCE: 179

```
Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
```

```
            20                  25                  30

Gly Asn Val Ala Trp Tyr Gln Gln Lys Pro Gly Lys Ala Pro Lys Leu
        35                  40                  45

Leu Ile Ser Ser Thr Ala Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Tyr Asp Phe
                85                  90                  95

Pro Leu Thr Phe Gly Gln Gly Thr Lys Val Glu Ile Lys Arg
            100                 105                 110


<210> SEQ ID NO 180
<211> LENGTH: 122
<212> TYPE: PRT
<213> ORGANISM: Artificial Sequence
<220> FEATURE:
<223> OTHER INFORMATION: synthesized_NP12-VH

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asn Gly
            20                  25                  30

Tyr Ile His Trp Val Arg Gln Ala Pro Gly Lys Gly Leu Glu Trp Val
        35                  40                  45

Ala Ser Ile Trp Pro Ser Trp Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Tyr Tyr Tyr Gly Asp Tyr Trp Gly Gln Gly Thr Leu
            100                 105                 110

Val Thr Val Ser Ser Ala Ser Ala Ala Ala
        115                 120


<210> SEQ ID NO 181
<211> LENGTH: 110
<212> TYPE: PRT
<213> ORGANISM: Artificial Sequence
<220> FEATURE:
<223> OTHER INFORMATION: synthesized_NP13-VL

<400> SEQUENCE: 181

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Tyr Trp Val Ala Trp Tyr Gln Gln Lys Pro Gly Lys Ala Pro Lys Leu
        35                  40                  45

Leu Ile Ser Ser Ala Ser Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Gly Trp Asp Trp
                85                  90                  95
```

```
Pro Ile Thr Phe Gly Gln Gly Thr Lys Val Glu Ile Lys Arg
            100                 105                 110


<210> SEQ ID NO 182
<211> LENGTH: 125
<212> TYPE: PRT
<213> ORGANISM: Artificial Sequence
<220> FEATURE:
<223> OTHER INFORMATION: synthesized_NP13-VH

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Asn Tyr
            20                  25                  30

Gly Ile His Trp Val Arg Gln Ala Pro Gly Lys Gly Leu Glu Trp Val
        35                  40                  45

Ala Ser Ile Gly Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Tyr Phe Asn Trp Leu Asp Met Asp Tyr Trp Gly Gln
            100                 105                 110

Gly Thr Leu Val Thr Val Ser Ser Ala Ser Ala Ala Ala
        115                 120                 125


<210> SEQ ID NO 183
<211> LENGTH: 110
<212> TYPE: PRT
<213> ORGANISM: Artificial Sequence
<220> FEATURE:
<223> OTHER INFORMATION: synthesized_NP14-VL

<400> SEQUENCE: 183

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asp
            20                  25                  30

Asn Asp Val Ala Trp Tyr Gln Gln Lys Pro Gly Lys Ala Pro Lys Leu
        35                  40                  45

Leu Ile Tyr Gly Pro Arg Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Ser Ser Trp
                85                  90                  95

Pro Leu Thr Phe Gly Gln Gly Thr Lys Val Glu Ile Lys Arg
            100                 105                 110


<210> SEQ ID NO 184
<211> LENGTH: 125
<212> TYPE: PRT
<213> ORGANISM: Artificial Sequence
<220> FEATURE:
<223> OTHER INFORMATION: synthesized_NP14-VH

<400> SEQUENCE: 184

Glu Val Gln Leu Val Glu Ser Gly Gly Gly Leu Val Gln Pro Gly Gly
```

```
1               5                   10                  15

Ser Leu Arg Leu Ser Cys Ala Ala Ser Gly Phe Thr Ile Asp Asn Gly
            20                  25                  30

Gly Ile His Trp Val Arg Gln Ala Pro Gly Lys Gly Leu Glu Trp Val
        35                  40                  45

Ala Ser Ile Trp Pro Ser Trp Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asn Phe Gly Val Phe Gly Val Met Asp Tyr Trp Gly Gln
            100                 105                 110

Gly Thr Leu Val Thr Val Ser Ser Ala Ser Ala Ala Ala
        115                 120                 125


<210> SEQ ID NO 185
<211> LENGTH: 110
<212> TYPE: PRT
<213> ORGANISM: Artificial Sequence
<220> FEATURE:
<223> OTHER INFORMATION: synthesized_NP15-VL

<400> SEQUENCE: 185

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asp
            20                  25                  30

Asn Asn Val Ala Trp Tyr Gln Gln Lys Pro Gly Lys Ala Pro Lys Leu
        35                  40                  45

Leu Ile Ser Tyr Ser Thr Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Trp Asn Tyr
                85                  90                  95

Pro Ile Thr Phe Gly Gln Gly Thr Lys Val Glu Ile Lys Arg
            100                 105                 110


<210> SEQ ID NO 186
<211> LENGTH: 125
<212> TYPE: PRT
<213> ORGANISM: Artificial Sequence
<220> FEATURE:
<223> OTHER INFORMATION: synthesized_NP15-VH

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Trp
            20                  25                  30

Tyr Ile His Trp Val Arg Gln Ala Pro Gly Lys Gly Leu Glu Trp Val
        35                  40                  45

Ala Gly Ile Gly Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ala Arg Phe His Trp Asp His Leu His Gly Met Asp Tyr Trp Gly Gln
            100                 105                 110

Gly Thr Leu Val Thr Val Ser Ser Ala Ser Ala Ala Ala
        115                 120                 125


<210> SEQ ID NO 187
<211> LENGTH: 110
<212> TYPE: PRT
<213> ORGANISM: Artificial Sequence
<220> FEATURE:
<223> OTHER INFORMATION: synthesized_NP16-VL

<400> SEQUENCE: 187

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Ser Tyr Val Ala Trp Tyr Gln Gln Lys Pro Gly Lys Ala Pro Lys Leu
        35                  40                  45

Leu Ile Ser Trp Thr Thr Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Phe Ser Tyr
                85                  90                  95

Pro Val Thr Phe Gly Gln Gly Thr Lys Val Glu Ile Lys Arg
            100                 105                 110


<210> SEQ ID NO 188
<211> LENGTH: 125
<212> TYPE: PRT
<213> ORGANISM: Artificial Sequence
<220> FEATURE:
<223> OTHER INFORMATION: synthesized_NP16-VH

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Asn Ser
            20                  25                  30

Gly Ile His Trp Val Arg Gln Ala Pro Gly Lys Gly Leu Glu Trp Val
        35                  40                  45

Ala Trp Ile Gly Pro Tyr Trp Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Asn His Trp His Leu Phe Met Asp Tyr Trp Gly Gln
            100                 105                 110

Gly Thr Leu Val Thr Val Ser Ser Ala Ser Ala Ala Ala
        115                 120                 125


<210> SEQ ID NO 189
<211> LENGTH: 110
<212> TYPE: PRT
<213> ORGANISM: Artificial Sequence
```

```
<220> FEATURE:
<223> OTHER INFORMATION: synthesized_NP17-VL

<400> SEQUENCE: 189

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Tyr Ser Val Ala Trp Tyr Gln Gln Lys Pro Gly Lys Ala Pro Lys Leu
        35                  40                  45

Leu Ile Ser Ser Pro Gly Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Tyr Asp Tyr
                85                  90                  95

Pro Val Thr Phe Gly Gln Gly Thr Lys Val Glu Ile Lys Arg
            100                 105                 110


<210> SEQ ID NO 190
<211> LENGTH: 125
<212> TYPE: PRT
<213> ORGANISM: Artificial Sequence
<220> FEATURE:
<223> OTHER INFORMATION: synthesized_NP17-VH

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Gly Gly
            20                  25                  30

Ser Ile His Trp Val Arg Gln Ala Pro Gly Lys Gly Leu Glu Trp Val
        35                  40                  45

Ala Ser Ile Trp Pro Phe Gly Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly His Gly His Asn Val Ile Met Asp Tyr Trp Gly Gln
            100                 105                 110

Gly Thr Leu Val Thr Val Ser Ser Ala Ser Ala Ala Ala
        115                 120                 125


<210> SEQ ID NO 191
<211> LENGTH: 110
<212> TYPE: PRT
<213> ORGANISM: Artificial Sequence
<220> FEATURE:
<223> OTHER INFORMATION: synthesized_NP18-VL

<400> SEQUENCE: 191

Met Ala Asp Ile Gln Met Thr Gln Ser Ser Ser Ser Leu Ser Ala Ser
1               5                   10                  15

Val Gly Asp Arg Val Thr Ile Thr Cys Arg Ala Ser Gln Asp Val Gly
            20                  25                  30

Tyr Tyr Val Ala Trp Tyr Gln Gln Lys Pro Gly Lys Ala Pro Lys Leu
        35                  40                  45
```

```
Leu Ile Tyr Gly Pro Arg Phe Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Ser Asn Trp
                85                  90                  95

Pro Ile Thr Phe Gly Gln Gly Thr Lys Val Glu Ile Lys Arg
            100                 105                 110


<210> SEQ ID NO 192
<211> LENGTH: 125
<212> TYPE: PRT
<213> ORGANISM: Artificial Sequence
<220> FEATURE:
<223> OTHER INFORMATION: synthesized_NP18-VH

<400> SEQUENCE: 192

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Gly Gly
            20                  25                  30

Gly Ile His Trp Val Arg Gln Ala Pro Gly Lys Gly Leu Glu Trp Val
        35                  40                  45

Ala Ser Ile Trp Pro Ser Trp Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe His Asn Gly Gly Phe Leu Val Met Asp Tyr Trp Gly Gln
            100                 105                 110

Gly Thr Leu Val Thr Val Ser Ser Ala Ser Ala Ala Ala
        115                 120                 125


<210> SEQ ID NO 193
<211> LENGTH: 110
<212> TYPE: PRT
<213> ORGANISM: Artificial Sequence
<220> FEATURE:
<223> OTHER INFORMATION: synthesized_NP19-VL

<400> SEQUENCE: 193

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Ser
            20                  25                  30

Gly Trp Val Ala Trp Tyr Gln Gln Lys Pro Gly Lys Ala Pro Lys Leu
        35                  40                  45

Leu Ile Ser Trp Ser Thr Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Phe Asn Phe
                85                  90                  95

Pro Val Thr Phe Gly Gln Gly Thr Lys Val Glu Ile Lys Arg
            100                 105                 110


<210> SEQ ID NO 194
```

```
<211> LENGTH: 125
<212> TYPE: PRT
<213> ORGANISM: Artificial Sequence
<220> FEATURE:
<223> OTHER INFORMATION: synthesized_NP19-VH

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Ser Trp
            20                  25                  30

Gly Ile His Trp Val Arg Gln Ala Pro Gly Lys Gly Leu Glu Trp Val
        35                  40                  45

Ala Gly Ile Gly Pro Phe Trp Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Gly Val Asp Asn Tyr Gly Tyr Met Asp Tyr Trp Gly Gln
            100                 105                 110

Gly Thr Leu Val Thr Val Ser Ser Ala Ser Ala Ala Ala
        115                 120                 125


<210> SEQ ID NO 195
<211> LENGTH: 110
<212> TYPE: PRT
<213> ORGANISM: Artificial Sequence
<220> FEATURE:
<223> OTHER INFORMATION: synthesized_NP20-VL

<400> SEQUENCE: 195

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Tyr Gly Val Ala Trp Tyr Gln Gln Lys Pro Gly Lys Ala Pro Lys Leu
        35                  40                  45

Leu Ile Ser Gly Ala Ser Gly Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Ser Ser Phe
                85                  90                  95

Pro Leu Thr Phe Gly Gln Gly Thr Lys Val Glu Ile Lys Arg
            100                 105                 110


<210> SEQ ID NO 196
<211> LENGTH: 119
<212> TYPE: PRT
<213> ORGANISM: Artificial Sequence
<220> FEATURE:
<223> OTHER INFORMATION: synthesized_NP20-VH

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Gly Tyr
            20                  25                  30
```

```
Ser Ile His Trp Val Arg Gln Ala Pro Gly Lys Gly Leu Glu Trp Val
        35                  40                  45

Ala Ser Ile Gly Pro Tyr Gly Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Phe Gly Phe Tyr Tyr Trp Gly Gln Gly Thr Leu Val Thr Val
            100                 105                 110

Ser Ser Ala Ser Ala Ala Ala
        115


<210> SEQ ID NO 197
<211> LENGTH: 110
<212> TYPE: PRT
<213> ORGANISM: Artificial Sequence
<220> FEATURE:
<223> OTHER INFORMATION: synthesized_NP21-VL

<400> SEQUENCE: 197

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Tyr
            20                  25                  30

Phe Tyr Val Ala Trp Tyr Gln Gln Lys Pro Gly Lys Ala Pro Lys Leu
        35                  40                  45

Leu Ile Tyr Gly Ser Arg Trp Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Ser Asn Phe
                85                  90                  95

Pro Val Thr Phe Gly Gln Gly Thr Lys Val Glu Ile Lys Arg
            100                 105                 110


<210> SEQ ID NO 198
<211> LENGTH: 125
<212> TYPE: PRT
<213> ORGANISM: Artificial Sequence
<220> FEATURE:
<223> OTHER INFORMATION: synthesized_NP21-VH

<400> SEQUENCE: 198

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asn Gly Tyr
            20                  25                  30

Gly Ile His Trp Val Arg Gln Ala Pro Gly Lys Gly Leu Glu Trp Val
        35                  40                  45

Ala Gly Ile Trp Pro Tyr Gly Gly Ser Thr Phe Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Tyr Asn Asn His Gly Gly Ile Met Asp Tyr Trp Gly Gln
            100                 105                 110
```

```
Gly Thr Leu Val Thr Val Ser Ser Ala Ser Ala Ala Ala
        115                 120                 125


<210> SEQ ID NO 199
<211> LENGTH: 110
<212> TYPE: PRT
<213> ORGANISM: Artificial Sequence
<220> FEATURE:
<223> OTHER INFORMATION: synthesized_NP22-VL

<400> SEQUENCE: 199

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Phe
            20                  25                  30

Ser Trp Val Ala Trp Tyr Gln Gln Lys Pro Gly Lys Ala Pro Lys Leu
        35                  40                  45

Leu Ile Ser Ser Ala Ser Ser Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Trp Asp Tyr
                85                  90                  95

Pro Ile Thr Phe Gly Gln Gly Thr Lys Val Glu Ile Lys Arg
            100                 105                 110


<210> SEQ ID NO 200
<211> LENGTH: 122
<212> TYPE: PRT
<213> ORGANISM: Artificial Sequence
<220> FEATURE:
<223> OTHER INFORMATION: synthesized_NP22-VH

<400> SEQUENCE: 200

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Trp
            20                  25                  30

Ser Ile His Trp Val Arg Gln Ala Pro Gly Lys Gly Leu Glu Trp Val
        35                  40                  45

Ala Gly Ile Trp Pro Tyr Trp Gly Ser Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Phe Tyr Ser Trp Phe Asp Tyr Trp Gly Gln Gly Thr Leu
            100                 105                 110

Val Thr Val Ser Ser Ala Ser Ala Ala Ala
        115                 120


<210> SEQ ID NO 201
<211> LENGTH: 110
<212> TYPE: PRT
<213> ORGANISM: Artificial Sequence
<220> FEATURE:
<223> OTHER INFORMATION: synthesized_NP23-VL

<400> SEQUENCE: 201
```

```
Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Asp
            20                  25                  30

Asp Gly Val Ala Trp Tyr Gln Gln Lys Pro Gly Lys Ala Pro Lys Leu
        35                  40                  45

Leu Ile Ser Gly Ala Arg Trp Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Tyr Asn Phe
                85                  90                  95

Pro Leu Thr Phe Gly Gln Gly Thr Lys Val Glu Ile Lys Arg
            100                 105                 110


<210> SEQ ID NO 202
<211> LENGTH: 119
<212> TYPE: PRT
<213> ORGANISM: Artificial Sequence
<220> FEATURE:
<223> OTHER INFORMATION: synthesized_NP23-VH

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asn Tyr
            20                  25                  30

Phe Ile His Trp Val Arg Gln Ala Pro Gly Lys Gly Leu Glu Trp Val
        35                  40                  45

Ala Ser Ile Gly Pro Phe Gly Gly Phe Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Gly Tyr Gly Phe His Tyr Trp Gly Gln Gly Thr Leu Val Thr Val
            100                 105                 110

Ser Ser Ala Ser Ala Ala Ala
        115


<210> SEQ ID NO 203
<211> LENGTH: 110
<212> TYPE: PRT
<213> ORGANISM: Artificial Sequence
<220> FEATURE:
<223> OTHER INFORMATION: synthesized_NP24-VL

<400> SEQUENCE: 203

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Gly
            20                  25                  30

Ser Ser Val Ala Trp Tyr Gln Gln Lys Pro Gly Lys Ala Pro Lys Leu
        35                  40                  45

Leu Ile Phe Tyr Thr Ser Ser Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80
```

```
Gln Pro Glu Asp Phe Ala Thr Tyr Tyr Cys Gln Gln Gly Trp Asp Ser
                85                  90                  95

Pro Val Thr Phe Gly Gln Gly Thr Lys Val Glu Ile Lys Arg
            100                 105                 110


<210> SEQ ID NO 204
<211> LENGTH: 122
<212> TYPE: PRT
<213> ORGANISM: Artificial Sequence
<220> FEATURE:
<223> OTHER INFORMATION: synthesized_NP24-VH

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Asp Asp Trp
            20                  25                  30

Tyr Ile His Trp Val Arg Gln Ala Pro Gly Lys Gly Leu Glu Trp Val
        35                  40                  45

Ala Gly Ile Gly Pro Tyr Gly Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Gly Ser Phe Asp Tyr Trp Gly Gln Gly Thr Leu
            100                 105                 110

Val Thr Val Ser Ser Ala Ser Ala Ala Ala
        115                 120


<210> SEQ ID NO 205
<211> LENGTH: 110
<212> TYPE: PRT
<213> ORGANISM: Artificial Sequence
<220> FEATURE:
<223> OTHER INFORMATION: synthesized_NP25-VL

<400> SEQUENCE: 205

Met Ala Asp Ile Gln Met Thr Gln Ser Pro Ser Ser Leu Ser Ala Ser
1               5                   10                  15

Val Gly Asp Arg Val Thr Ile Thr Cys Arg Ala Gly Gln Asp Val Ser
            20                  25                  30

Ser Gly Val Ala Trp Tyr Gln Gln Lys Pro Gly Lys Ala Pro Lys Leu
        35                  40                  45

Leu Ile Ser Trp Thr Ser Phe Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Tyr Asp Tyr
                85                  90                  95

Pro Ile Thr Phe Gly Gln Gly Thr Lys Val Glu Ile Lys Arg
            100                 105                 110


<210> SEQ ID NO 206
<211> LENGTH: 122
<212> TYPE: PRT
<213> ORGANISM: Artificial Sequence
<220> FEATURE:
<223> OTHER INFORMATION: synthesized_NP25-VH
```

-continued

```
<400> SEQUENCE: 206

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Gly Gly Gly
            20                  25                  30

Phe Ile His Trp Val Arg Gln Ala Pro Gly Lys Gly Leu Glu Trp Val
        35                  40                  45

Ala Ser Ile Trp Pro Tyr Trp Gly Phe Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Tyr Gly Tyr Ser Asp Tyr Trp Gly Gln Gly Thr Leu
            100                 105                 110

Val Thr Val Ser Ser Ala Ser Ala Ala Ala
        115                 120
```

METHOD FOR SELECTING ANTIBODY FRAGMENTS, RECOMBINANT ANTIBODIES PRODUCED THEREFROM, AND USES THEREOF

This application is a U.S. National Stage Filing under 35 U.S.C. 371 from International Patent Application Serial No. PCT/US21/36274, filed Jun. 7, 2021, and published on Dec. 16, 2021, which claims the priority of U.S. Ser. No. 63/036,143, filed Jun. 8, 2020, the disclosure of which are incorporated by reference herein in their entireties.

BACKGROUND OF THE INVENTION

1. FIELD OF THE INVENTION

The present disclosure in general relates to a method of selecting antibody fragments specific to influenza virus, and uses of the selected antibody fragments in diagnosing influenza virus infection.

2. DESCRIPTION OF RELAYED ART

Enzyme-linked immunosorbent assay (ELISA) and lateral flow immunoassay (LFIA) are powerful technologies for rapid and quantitative/semi-quantitative molecular detections. Applications of these immunoassay platforms bring about tools in disease preventions/treatments, food safety assurances, immunogen detections and environmental contamination controls. In particular, LFIAs are compatible with the World Health Organization (WHO) ASSURED (affordable, sensitive, specific, user-friendly, rapid and robust, equipment free and deliverable) guidelines for indispensable diagnostics to be used by untrained personnel in resource-poor situations for urgent needs in health care and infectious disease control.

There are unmet technical needs in overcoming the challenges frequently encountered in developing ELISA and LFIA applications. The key components underlying these two immunoassay platforms are antibody-based affinity reagents, most of which are mono- or poly-clonal antibodies from immunized animals. The downsides of animal-based antibodies as affinity reagents are threefold: Firstly, the discovery and development timespan for animal antibodies requires up to 16-24 months, which is frequently much longer than the period critical in preventing the exacerbation of a major disaster, such as pandemic infectious disease outbreaks in humans. Secondly, animal B cell responses to an antigen are frequently focused on only a few immunodominant B cell epitopes of the antigen, leading to limited choices of the animal antibodies as affinity reagents. Thirdly, even when animal antibodies become available as affinity antigens, the capability of these antibodies in distinguishing highly similar antigens is not guaranteed, and frequently, the end products have had the difficulty to distinguish virulent pathogen strains from their related but non-virulent ones.

Influenza viruses can cross species barriers to infect diverse hosts due to rapid mutation, genetic drift and genome reassortment, resulting in the emergence of novel influenza strains, such as H5N1 (Hong Kong) in 1997, H7N9 (China), H10N8 (China) and H6N1 (Taiwan) in 2013 and H5N6 (Hong Kong) in 2014. Rapid detection of these emerging influenza virus strains is a critical measure responding to the threats imposed by the influenza pandemic outbreaks and seasonal influenza epidemics on human society and economy. Rapid influenza diagnostic tests (RIDTs) for influenza virus nucleoprotein (NP) are frequently used to enable healthcare professionals to make immediate and effective treatment decisions and prevent unnecessary prescriptions of antibiotics and antiviral medications. LFIA-based tests for influenza virus type A (IAV) and B (IBV) have been widely available as RIDTs, but the sensitive of these tests are nevertheless in the range of 40% to 70%, partly due to the difficulty to cover increasingly diverse influenza strains.

In view of the foregoing, there exists in the related art a need for a method of efficiently producing an antibody with sufficient specificity and affinity to distinguish influenza virus subtypes so as to establish a diagnostic platform for infection prevention and/or treatment purposes.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method for selecting an antibody fragment specific to an influenza virus. According to embodiments of the present disclosure, the method comprises the steps of, (a) providing a phage-displayed single-chain variable fragment (scFv) library that comprises a plurality of phage-displayed scFvs, wherein the heavy chain variable (VH) domain of each phage-displayed scFvs has a binding affinity to protein A, and the light chain variable (VL) domain of each phage-displayed scFvs has a binding affinity to protein L;

(b) exposing the phage-displayed scFv library of the step (a) to a target nucleoprotein comprising an amino acid sequence selected from the group consisting of SEQ ID NOs: 1-6;

(c) selecting, from the phage-displayed scFv library of the step (b), a first plurality of phages that respectively express scFvs exhibiting binding affinity to the target nucleoprotein;

(d) exposing the first plurality of phages selected in the step (c) to the target nucleoprotein in the presence of at least one scrambled nucleoprotein, wherein the scrambled nucleoprotein comprises an amino acid sequence selected from the group consisting of SEQ ID NOs: 1-6, and the amino acid sequence of the scrambled nucleoprotein is different from the amino acid sequence of the target nucleoprotein;

(e) selecting, from the first plurality of phages of the step (d), a second plurality of phages that respectively express scFvs exhibiting binding affinity to the target nucleoprotein in the presence of the scrambled nucleoprotein;

(f) respectively enabling the second plurality of phages selected in the step (e) to express a plurality of soluble scFvs;

(g) exposing the plurality of soluble scFvs of the step (f) to the target nucleoprotein;

(h) determining the respective binding affinity of the plurality of soluble scFvs in the step (g); and (i) based on the results determined in the step (h), selecting one soluble scFv that exhibits superior affinity over the other soluble scFvs of the plurality of soluble scFvs as the antibody fragment.

According to some embodiments of the present disclosure, the influenza virus is influenza virus type A (also known as "influenza A virus", IAV). According to some embodiments, the influenza virus is influenza virus type B (also known as "influenza B virus", IBV). In certain exemplary embodiments, the influenza virus is AV subtype H1N1, H3N2, or H5N1.

The thus-selected antibody fragment is useful in preparing a recombinant antibody for detecting influenza virus infection, e.g., IAV infection or IBV infection. According to certain embodiments of the present disclosure, 25 antibody fragments respectively designated as "NP1" to "NP25" are selected from the phage-displayed scFv library, and accordingly, 25 recombinant antibodies are prepared therefrom. The second aspect of the present disclosure thus pertains to a recombinant antibody or a fragment thereof (e.g., scFv), which, in structure, comprises a VL domain and a VH domain, wherein the VL domain comprises a first light chain complementarity determining region (CDR-L1), a second light chain CDR (CDR-L2) and a third light chain CDR (CDR-L3), and the VH domain comprises a first heavy chain CDR (CDR-H1), a second heavy chain CDR (CDR-H2) and a third heavy chain CDR (CDR-H3).

According to some embodiment, the CDR-L1, CDR-L2, CDR-L3, CDR-H1, CDR-H2 and CDR-H3 of the antibody fragment NP1 respectively comprise the amino acid sequences of SEQ ID NOs: 7-12; the CDR-L1, CDR-L2, CDR-L3, CDR-H1, CDR-H2 and CDR-H3 of the antibody fragment NP2 respectively comprise the amino acid sequences of SEQ ID NOs: 13-18; the CDR-L1, CDR-L2, CDR-L3, CDR-H1, CDR-H2 and CDR-H3 of the antibody fragment NP3 respectively comprise the amino acid sequences of SEQ ID NOs: 19-24; the CDR-L1, CDR-L2, CDR-L3, CDR-H1, CDR-H2 and CDR-H3 of the antibody fragment NP4 respectively comprise the amino acid sequences of SEQ ID NOs: 25-30; the CDR-L1, CDR-L2, CDR-L3, CDR-H1, CDR-H2 and CDR-H3 of the antibody fragment NP5 respectively comprise the amino acid sequences of SEQ ID NOs: 31-36; the CDR-L1, CDR-L2, CDR-L3, CDR-H1, CDR-H2 and CDR-H3 of the antibody fragment NP6 respectively comprise the amino acid sequences of SEQ ID NOs: 37-42; the CDR-L1, CDR-L2, CDR-L3, CDR-H1, CDR-H2 and CDR-H3 of the antibody fragment NP7 respectively comprise the amino acid sequences of SEQ ID NOs: 43-48; the CDR-L1, CDR-L2, CDR-L3, CDR-H1, CDR-H2 and CDR-H3 of the antibody fragment NP8 respectively comprise the amino acid sequences of SEQ ID NOs: 49-54; the CDR-L1, CDR-L2, CDR-L3, CDR-H1, CDR-H2 and CDR-H3 of the antibody fragment NP9 respectively comprise the amino acid sequences of SEQ ID NOs: 55-60; the CDR-L1, CDR-L2, CDR-L3, CDR-H1, CDR-H2 and CDR-H3 of the antibody fragment NP10 respectively comprise the amino acid sequences of SEQ ID NOs: 61-66; the CDR-L1, CDR-L2, CDR-L3, CDR-H1, CDR-H2 and CDR-H3 of the antibody fragment NP11 respectively comprise the amino acid sequences of SEQ ID NOs: 67-72; the CDR-L1, CDR-L2, CDR-L3, CDR-H1, CDR-H2 and CDR-H3 of the antibody fragment NP11 respectively comprise the amino acid sequences of SEQ ID NOs: 73-78; the CDR-L1, CDR-L2, CDR-L3, CDR-H1, CDR-H2 and CDR-H3 of the antibody fragment NP13 respectively comprise the amino acid sequences of SEQ ID NOs: 79-84; the CDR-L1, CDR-L2, CDR-L3, CDR-H1, CDR-H2 and CDR-H3 of the antibody fragment NP14 respectively comprise the amino acid sequences of SEQ ID NOs: 85-90; the CDR-L1, CDR-L2, CDR-L3, CDR-H1, CDR-H2 and CDR-H3 of the antibody fragment NP15 respectively comprise the amino acid sequences of SEQ ID NOs: 91-96; the CDR-L1, CDR-L2, CDR-L3, CDR-H1, CDR-H2 and CDR-H3 of the antibody fragment NP16 respectively comprise the amino acid sequences of SEQ ID NOs: 97-102; the CDR-L1, CDR-L2, CDR-L3, CDR-H1, CDR-H2 and CDR-H3 of the antibody fragment NP17 respectively comprise the amino acid sequences of SEQ ID NOs: 103-108; the CDR-L1, CDR-L2, CDR-L3, CDR-H1, CDR-H2 and CDR-H3 of the antibody fragment NP18 respectively comprise the amino acid sequences of SEQ ID NOs: 109-114; the CDR-L1, CDR-L2, CDR-L3, CDR-H1, CDR-H2 and CDR-H3 of the antibody fragment NP19 respectively comprise the amino acid sequences of SEQ ID NOs: 115-120; the CDR-L1, CDR-L2, CDR-L3, CDR-H1, CDR-H2 and CDR-H3 of the antibody fragment NP20 respectively comprise the amino acid sequences of SEQ ID NOs: 121-126; the CDR-L1, CDR-L2, CDR-L3. CDR-H1, CDR-H2 and CDR-H3 of the antibody fragment NP21 respectively comprise the amino acid sequences of SEQ ID NOs: 127-132; the CDR-L1, CDR-L2, CDR-L3, CDR-H1, CDR-H2 and CDR-H3 of the antibody fragment NP22 respectively comprise the amino acid sequences of SEQ ID NOs: 133-138; the CDR-L1, CDR-L2, CDR-L3, CDR-H1, CDR-H2 and CDR-H3 of the antibody fragment NP23 respectively comprise the amino acid sequences of SEQ LD NOs: 139-144; the CDR-L1, CDR-L2, CDR-L3, CDR-H1, CDR-H2 and CDR-H3 of the antibody fragment NP24 respectively comprise the amino acid sequences of SEQ ID NOs: 145-150; and the CDR-L1, CDR-L2, CDR-L3, CDR-H1, CDR-H2 and CDR-H3 of the antibody fragment NP25 respectively comprise the amino acid sequences of SEQ ID NOs: 151-156.

According to certain embodiments, the VL domain and the VH domain of the antibody fragment NP1 respectively comprise amino acid sequences at least 85% identical to SEQ ID NOs: 157 and 158; the VL domain and the VH domain of the antibody fragment NP2 respectively comprise amino acid sequences at least 85% identical to SEQ ID NOs: 159 and 160; the VL domain and the VH domain of the antibody fragment NP3 respectively comprise amino acid sequences at least 85% identical to SEQ ID NOs: 161 and 162; the VL domain and the VH domain of the antibody fragment NP4 respectively comprise amino acid sequences at least 85% identical to SEQ ID NOs: 163 and 164; the VL domain and the VH domain of the antibody fragment NP5 respectively comprise amino acid sequences at least 85% identical to SEQ ID NOs: 165 and 166; the VL domain and the VH domain of the antibody fragment NP6 respectively comprise amino acid sequences at least 85% identical to SEQ ID NOs: 167 and 168; the VL domain and the VH domain of the antibody fragment NP7 respectively comprise amino acid sequences at least 85% identical to SEQ ID NOs: 169 and 170; the VL domain and the VH domain of the antibody fragment NP8 respectively comprise amino acid sequences at least 85% identical to SEQ ID NOs: 171 and 172; the VL domain and the VH domain of the antibody fragment NP9 respectively comprise amino acid sequences at least 85% identical to SEQ ID NOs: 173 and 174; the VL domain and the VH domain of the antibody fragment NP10 respectively comprise amino acid sequences at least 85% identical to SEQ ID NOs: 175 and 176; the VL domain and the VH domain of the antibody fragment NP11 respectively comprise amino acid sequences at least 85% identical to SEQ ID NOs: 177 and 178; the VL domain and the VH domain of the antibody fragment NP12 respectively comprise amino acid sequences at least 85% identical to SEQ ID NOs: 179 and 180; the VL domain and the VH domain of the antibody fragment NP13 respectively comprise amino acid sequences at least 85% identical to SEQ ID NOs: 181 and 182; the VL domain and the VH domain of the antibody fragment NP14 respectively comprise amino acid sequences at least 85% identical to SEQ ID NOs: 183 and 184; the VL domain and the VH domain of the antibody fragment NP15 respectively comprise amino acid sequences at least 85% identical to SEQ ID NOs: 185 and 186; the VL domain and the VH domain of the antibody fragment NP16 respectively comprise amino acid sequences at least 85% identical to SEQ ID NOs: 187 and 188; the VL domain and the VH domain of the antibody fragment NP17 respectively comprise amino acid sequences at least 85% identical to SEQ ID NOs: 189 and 190; the VL domain and the VH domain of the antibody fragment NP18 respectively comprise amino acid sequences at least 85% identical to SEQ ID NOs: 191 and 192; the VL domain and the VH domain of the antibody fragment NP19 respectively comprise amino acid sequences at least 85% identical to SEQ ID NOs: 193 and 194; the VL domain and the VH domain of the antibody fragment NP20 respectively comprise amino acid sequences at least 85% identical to SEQ ID NOs: 195 and 196; the VL domain and the VH domain of the antibody fragment NP21 respectively comprise amino acid sequences at least 85% identical to SEQ ID NOs: 197 and 198; the VL domain and the VH domain of the antibody fragment NP22 respectively comprise amino acid sequences at least 85% identical to SEQ ID NOs: 199 and 200; the VL domain and the VH domain of the antibody fragment NP23 respectively comprise amino acid sequences at least 85% identical to SEQ ID NOs: 201 and 202; the VL domain and the VH domain of the antibody fragment NP24 respectively comprise amino acid sequences at least 85% identical to SEQ ID NOs: 203 and 204; and the VL domain and the VH domain of the antibody fragment NP25 respectively comprise amino acid sequences at least 85% identical to SEQ ID NOs: 205 and 206.

Another aspect of the present disclosure is directed to a method of determining whether a subject is infected by an influenza virus via a biological sample isolated from the subject. The method comprises the steps of, detecting the presence or absence of a nucleoprotein of the influenza virus in the biological sample by use of the antibody fragment or the recombinant antibody of the present disclosure, wherein the presence of the nucleoprotein indicates that the subject is infected by the influenza virus. According to some embodiments, the influenza virus is IAV or IBV. In some specific examples, the influenza virus is H1N1, H3N2 or H5N1.

Based on the result, a skilled artisan or a clinical practitioner may administer to a subject in need thereof an appropriate treatment in time. Specifically, in the case when the nucleoprotein is present in the biological sample of a subject, then an effective amount of an anti-viral treatment (e.g., oseltamivir, zanamivir, peramivir, baloxavir marboxil, amantadine, rimantadine, or a combination thereof) is administered to the subject so as to alleviate and/or ameliorate the symptoms associated with the influenza virus infection.

The subject is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where:

FIG. 1A: The recognitions of the 25 anti-NP IgG1s and the positive control antibodies (x-axis) to AL2C (positive control), NPB1, NPA1, and NPA2 immobilized on the NC membrane (y-axis). For each of the LFIAs, 1 μg/100 μL of the corresponding IgG was applied to the sample pad. FIG. 1B: Results of the sandwich LFIAs with immobilized AL2C (positive control), NP17, NP1, and NP16 on the NC membrane (y-axis) as capture reagents and colloidal gold-labelled NP17 as detection reagent incorporated in the conjugate pad fir the detection of respective NP applied to the sample pad (100 μL of $10^{-7}$ M NP) (x-axis). FIG. 1C: The detection limit of NPA1, which was elucidated by applying 10-fold serial diluted NPA1 solutions (x-axis) to the same sandwich LFIA strip as depicted in FIG. 1B.

DETAILED DESCRIPTION OF THE INVENTION

Figure 1A:
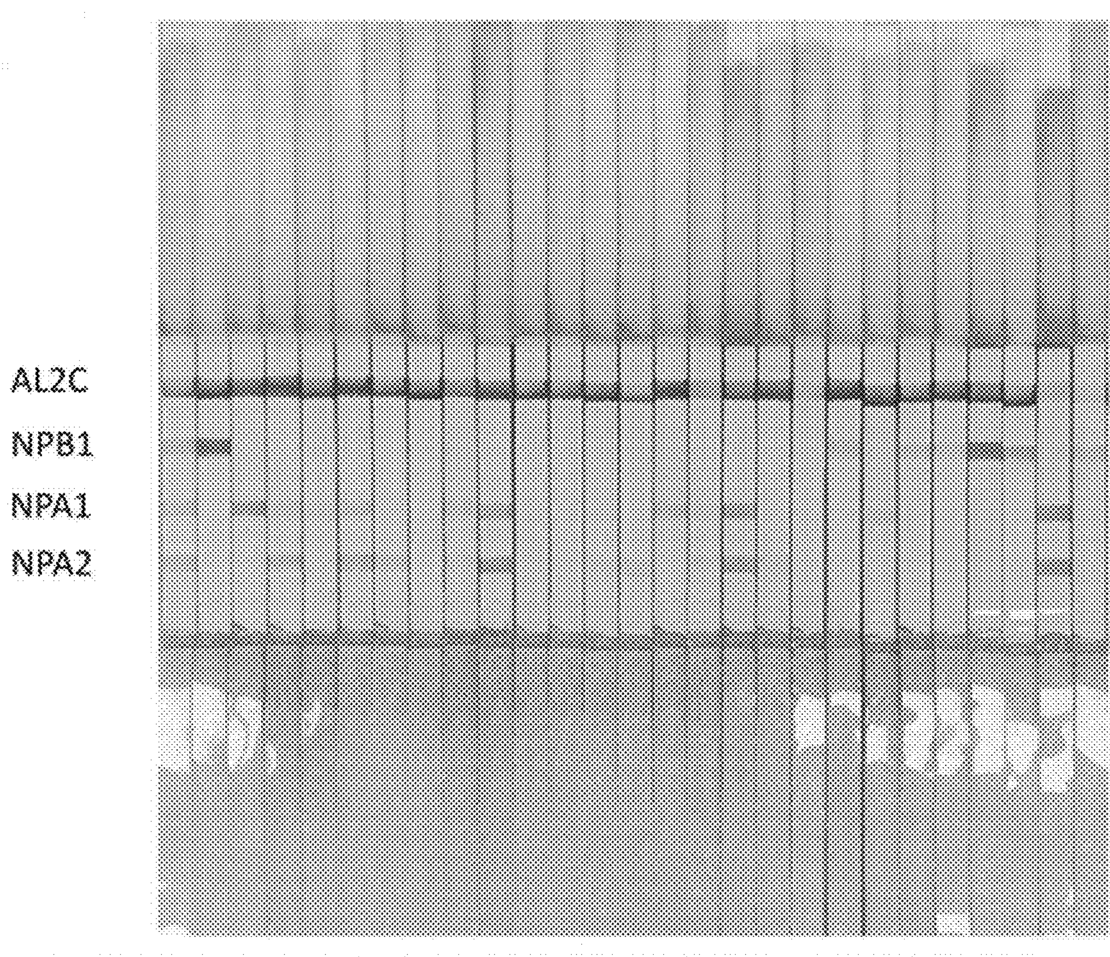
FIGS. 1A to 1C are photographs of LFIA that depicts the detection limits of anti-NP IgG1s to specified NPs.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antibody" is used in the broadest sense and specifically covers monoclonal antibodies (including full length monoclonal antibodies), polyclonal antibodies, multispecific or multivalent antibodies (e.g., bi-specific antibodies), and antibody fragments so long as they exhibit the desired biological activity. "Antibody fragments" comprise a portion of a full-length antibody, generally the antigen binding or variable region thereof, Examples of antibody fragments include fragment antigen-binding (Fab), Fab', F(ab')2, single-chain variable fragment (scFv), diabodies, linear antibodies, single-chain antibody molecules, and multi-specific antibodies formed from antibody fragments.

The term "antibody library" refers to a collection of antibodies and/or antibody fragments displayed for screening and/or combination into full antibodies. The antibodies and/or antibody fragments may be displayed on a ribosome; on a phage; or on a cell surface, in particular a yeast cell surface.

As used herein, the term "single-chain variable fragment" or "scFv" is a fusion protein comprising the variable regions of the heavy (VH) and light chains (VL) of an immunoglobulin, in which the VH and VL are covalently linked to form a VH:VL heterodimer. The VH and VL are either joined directly or joined by a peptide-encoding linker, which connects the N-terminus of the VH with the C-terminus of the VL, or the C-terminus of the VH with the N-terminus of the VL. The linker is usually rich in glycine for flexibility, as well as serine or threonine for solubility. Despite removal of the constant regions and the introduction of a linker, scFv proteins retain the specificity of the original immunoglobulin. scFvs can be expressed from a nucleic acid including VH- and VL-encoding sequences.

The term "$EC_{50}$," as used herein, refers to the concentration of an antibody or an antigen-binding portion thereof, which induces a response, either in an in vitro or an in vivo assay, which is 50% of the maximal response, i.e., halfway between the maximal response and the baseline.

The term "complementarity determining region" or "CDR" used herein refers to the hypervariable region of an antibody molecule that forms a surface complementary to the 3-dimensional surface of a bound antigen. Proceeding from N-terminus to C-terminus, each of the antibody heavy and light chains comprises three CDRs (CDR-1, CDR-2, and CDR-3). An HLA-DR antigen-binding site, therefore, includes a total of six CDRs that comprise three CDRs from the variable region of a heavy chain (i.e., CDR-H1, CDR-H2 and CDR-H3) and three CDRs from the variable region of a light chain (i.e., CDR-L1, CDR-L2 and CDR-L3). The amino acid residues of CDRs are in close contact with bound antigen, wherein the closest antigen contact is usually associated with the heavy chain CDR3.

The term "phagemid" refers to a vector, which combines attributes of a bacteriophage and a plasmid. A bacteriophage is defined as any one of a number of viruses that infect bacteria.

"Percentage (%) sequence identity" with respect to any amino acid sequence identified herein is defined as the percentage of amino acid residues in a candidate sequence that are identical with the amino acid residues in the specific reference sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage sequence identity of a given sequence A to a subject sequence B (which can alternatively be phrased as a given sequence A that has a certain % sequence identity to a given sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in the subject sequence B.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity, Antibodies of the present disclosure may be modified specifically to alter a feature of the peptide unrelated to its physiological activity. For example, certain amino acids can be changed and/or deleted without affecting the physiological activity of the antibody in this study (i.e., the ability of binding to influenza virus). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative.

Fragments or analogs of antibodies can be readily prepared by those of ordinary skill in the art. Preferred amino- and carboxy-termini of fragments or analogs occur near boundaries of functional domains.

The term "subject" refers to a mammal including the human species that can be subjected to the diagnosis and/or treatment methods of the present invention. The term "subject" is intended to refer to both the male and female gender unless one gender is specifically indicated.

II. Description of the Invention

The first aspect of the present disclosure is directed to a method for selecting an antibody fragment specific to an influenza virus. According to embodiments of the present disclosure, the method comprises the steps of, (a) providing a phage-displayed scFv library that comprises a plurality of phage-displayed scFvs, wherein the VH domain of each phage-displayed scFvs has a binding affinity to protein A, and the VL domain of each phage-displayed scFvs has a binding affinity to protein L;

(b) exposing the phage-displayed scFv library of the step (a) to a target nucleoprotein comprising an amino acid sequence selected from the group consisting of SEQ ID NOs: 1-6;

(c) selecting, from the phage-displayed scFv library of the step (b), a first plurality of phages that respectively express scFvs exhibiting binding affinity to the target nucleoprotein;

(d) exposing the first plurality of phages selected in the step (c) to the target nucleoprotein in the presence of at least one scrambled nucleoprotein, wherein the scrambled nucleoprotein comprises an amino acid sequence selected from the group consisting of SEQ ID NOs: 1-6, and the amino acid sequence of the scrambled nucleoprotein is different from the amino acid sequence of the target nucleoprotein;

(e) selecting, from the first plurality of phages of the step (d), a second plurality of phages that respectively express scFvs exhibiting binding affinity to the target nucleoprotein in the presence of the scrambled nucleoprotein;

(f) respectively enabling the second plurality of phages selected in the step (e) to express a plurality of soluble scFvs;

(g) exposing the plurality of soluble scFvs of the step (f) to the target nucleoprotein;

(h) determining the respective binding affinity of the plurality of soluble scFvs in the step (g); and (i) based on the results determined in the step (h), selecting one soluble scFv that exhibits superior affinity over the other soluble scFvs of the plurality of soluble scFvs as the antibody fragment.

The present method is useful in selecting an antibody fragment exhibiting a binding affinity and/or specificity to an influenza virus, and accordingly, providing a potential means to detect various subtypes of influenza virus with diverse but highly similar antigens. According to certain embodiments of the present disclosure, the influenza virus detectable by the selected antibody fragment may be influenza virus type A (i.e., IAV) or influenza virus type B (i.e., IBV). Non-limiting examples of IAV include, H1N1, H1N2, H2N2, H3N2, H5N1, H5N2, H7N2, H7N3, H7N7, H7N9, H9N2, or H10N7. In one working example, the influenza virus is H1N1, H3N2, or H5N1

In the step (a), a phage-displayed scFv library is provided. According to some embodiments of the present disclosure, the framework of the phage-displayed scFv library is based on the human IGKV1-NL1*01/IGHV3-23*04 germline sequence, and the CDR sequences including CDR-L1, CDR-L2, CDR-L3, CDR-H1, CDR-H2 and CDR-H3 sequences thereof are diversified by PCR reaction using desired primers. After the selection of protein A and protein L, the phage-displayed scFv library (hereinafter as "GH2 library," including GH2-5, GH2-6, GH2-7, GH2-8, GH2-9, GH2-10, GH2-11, GH2-12, GH2-13, GH2-14, GH2-16, GH2-18, GH2-20, GH2-22, and GH2-24 libraries in the present study) is produced, in which each of the plurality of phage-displayed scFvs has a VI-1 domain capable of binding to protein A, and a VL domain capable of binding to protein L. This phage-displayed scFv library can be constructed using the method described in the U.S. Pat. No. 10,336,815 B2 or U.S. Pat. No. 10,336,816 B2 and the publication of Ing-Chien Chen et al. (High throughput discovery of influenza virus neutralizing antibodies from phage-displayed synthetic antibody libraries, Scientific Reports 7, Article number: 14455 (2017)). The entirety of the application and publication are incorporated herein by reference.

In the step (b), the GH2 library is exposed to a target nucleoprotein selected from the group consisting of, (1) a recombinant nucleoprotein designated as "NPA1" that is derived from H3N2 and comprises an amino acid sequence of SEQ ID NO: 1; (2) a recombinant nucleoprotein designated as "NPA2" that is derived from H1N1 and comprises an amino acid sequence of SEQ ID NO: 2; (3) a recombinant nucleoprotein designated as "NPA3" that is derived from H1N1 and comprises an amino acid sequence of SEQ ID NO: 3; (4) a recombinant nucleoprotein designated as "NPA4" that is derived from H1N1 and comprises an amino acid sequence of SEQ ID NO: 4; (5) a recombinant nucleoprotein designated as "NPA5" that is derived from H15N1 and comprises an amino acid sequence of SEQ ID NO: 5; and (6) a recombinant nucleoprotein designated as "NPB1" that is derived from IBV and comprises an amino acid sequence of SEQ ID NO: 6. According to some embodiments, the target nucleoprotein is immobilized on a matrix (such as an agarose resin or polyacrylamide) and then mixed with the present GH2 library.

In the step (c), a plurality of phages (i.e., a first plurality of phages) respectively expressing scFvs that exhibit binding affinity to the target nucleoprotein are selected from the GH2 library. Specifically, the product of the step (b) is subjected to an elution buffer, which generally is an acidic solution (such as glycine solution, pH 2.2), so as to disrupt the binding between the target nucleoprotein and phage-display scFv. By this way, the first plurality of phages that respectively express scFvs exhibiting binding affinity to the target nucleoprotein are collected.

In the step (d), for the purpose of enriching the population of scFvs with binding specificity to the target nucleoprotein, the plurality of phages (i.e., the first plurality of phages) selected in the step (c) is subjected to the target nucleoprotein in the presence of one or more scrambled nucleoproteins, each of which comprises an amino acid sequence different from the amino acid sequence of the target nucleoprotein. According to some embodiments, the target nucleoprotein is the NPA1 protein, which is immobilized on a matrix (such as an agarose resin or polyacrylamide), and then mixed with the present GH2 library in the presence of one or more scrambled nucleoproteins independently selected from the group consisting of NPA2-NPA5 and NPB1 proteins. In one exemplary embodiment, the target nucleoprotein NPA1 is mixed with the present GH2 library in the presence of five scrambled nucleoproteins, including NPA2-NPA5 and NPB1 proteins. According to some embodiments, the target nucleoprotein is the NPA2 protein, which is immobilized on a matrix, and then mixed with the present GH2 library in the presence of one or more scrambled nucleoproteins independently selected from the group consisting of NPA1, NPA3-NPA5 and NPB1 proteins. In one exemplary embodiment, the target nucleoprotein NPA2 is mixed with the present GH2 library in the presence of five scrambled nucleoproteins, including NPA1, NPA3-NPA5 and NPB1 proteins. According to certain embodiments, the NPA3 protein serves as the target nucleoprotein, which is mixed with the present GH2 library in the presence of one or more scrambled nucleoproteins independently selected from the group consisting of NPA1, NPA2, NPA4, NPA5 and NPB1 proteins. In one exemplary embodiment, the target nucleoprotein NPA3 is mixed with the present GH2 library in the presence of five scrambled nucleoproteins, including NPA1, NPA2, NPA4, NPA5 and NPB1 proteins. According to certain embodiments, the NPA4 protein is employed as the target nucleoprotein, which is mixed with the present GH2 library in the presence of one or more scrambled nucleoproteins independently selected from the group consisting of NPA1-NPA3, NPA5 and NPB1 proteins. In one exemplary embodiment, the target nucleoprotein NPA4 is mixed with the present GH2 library in the presence of five scrambled nucleoproteins, including NPA1-NPA3, NPA5 and NPB1 proteins. According to some alternative embodiments, the NPA5 protein is used as the target nucleoprotein, which is mixed with the present G-H2 library in the presence of one or more scrambled nucleoproteins independently selected from the group consisting of NPA1-NPA4 and NPB1 proteins. In one exemplary embodiment, the target nucleoprotein NPA5 is mixed with the present GH2 library in the presence of five scrambled nucleoproteins, including NPA1-NPA4 and NPB1 proteins. According to certain alternative embodiments, the target nucleoprotein NPB1 is mixed with the present GH2 library in the presence of one or more scrambled nucleoproteins independently selected from the group consisting of NPA1-NPA5 proteins. In one exemplary embodiment, the target nucleoprotein NPB1 is mixed with the present GH2 library in the presence of five scrambled nucleoproteins, including NPA1-NPA5 proteins.

Then, in the step (e), a plurality of phages (i.e., a second plurality of phages) respectively expressing scFvs that exhibit binding specificity to the target nucleoprotein in the presence of scrambled nucleoprotein(s) are selected from the first plurality of phages. In a manner similar to the step (c), the product of the step (d) is subjected to an elution buffer, for example, an acidic solution (e.g., glycine solution, pH 2.2), so as to disrupt the binding between the target nucleoprotein and phage-display scFv. By this way, the second plurality of phages that respectively express scFvs exhibiting binding specificity to the target nucleoprotein are collected.

Next, in the step (f), the second plurality of phages selected in the step (e) are subjected to conditions that enable them to produce a plurality of soluble scFvs. This step can be carried out by using methods known to any person having ordinary skill in the art. According to certain embodiments of the present disclosure, the expression of VH and VL domains may be driven by a lactose operon (lac operon); as known by one skilled artisan, the lac operon would be induced by isopropyl-thio-β-D-galactoside (IPTG), which then drives the expression of the down-stream genes (i.e., genes encoding the VH and VL domains). The produced scFv are then secreted into the supernatant of culture medium and could be collected therefrom.

In the step (g), the soluble scFvs produced in the step (f) are respectively mixed with the target nucleoprotein so as to form the protein-scFv complexes.

Then, in the step (h), the level of the protein-scFv complexes formed in the step (g) is determined by a method known to a person having ordinary skill in the art for analyzing the binding affinity of two molecules (e.g., the binding affinity of an antibody to an antigen); for example, enzyme-linked immunosorbent assay (ELISA), western blotting (WB) assay, flow cytometry, or lateral flow immunoassay (LFIA). In general, the level of the protein-scFv complexes is proportional to the binding affinity of the scFv to the target nucleoprotein. According to one working example, the level of the protein-scFv complex (i.e., the binding affinity of the soluble scFv to the target nucleoprotein) is determined by ELISA Finally, in the step (i), the antibody fragment is selected based on the binding affinity determined in the step (h). More specifically, the soluble scFv that exhibits superior affinity to the target nucleoprotein over the other soluble scFvs of the plurality of soluble scFvs is selected as the antibody fragment.

The antibody fragment selected from the present scFv library is useful in preparing a recombinant antibody (e.g., an recombinant IgG antibody). The method of preparing a recombinant antibody from an scFv is known by a person having ordinary in the art, for example, the method described in U.S. Pat. No. 10,336,815 B2 or U.S. Pat. No. 10,336,816 B2.

According to certain embodiments of the present disclosure. 25 antibody fragments are selected from the present selecting method, and accordingly, 25 recombinant antibodies are produced therefrom. The sequence identifiers corresponding to the CDR sequences (including CDR-L1, CDR-L2, CDR-L3, CDR-H1, CDR-H2 and CDR-H3) of these antibody fragments/recombinant antibodies are respectively summarized in Table 1.

TABLE 1

Sequence identifiers (SEQ ID NOs) corresponding to the CDR sequences of specified antibodies

| | Sequence Identifier (SEQ ID NO) | | | | | |
|---|---|---|---|---|---|---|
| Antibody | CDR-L1 | CDR-L2 | CDR-L3 | CDR-H1 | CDR-H2 | CDR-H3 |
| NP1 | 7 | 8 | 9 | 10 | 11 | 12 |
| NP2 | 13 | 14 | 15 | 16 | 17 | 18 |
| NP3 | 19 | 20 | 21 | 22 | 23 | 4 |
| NP4 | 25 | 26 | 27 | 28 | 29 | 30 |
| NP5 | 31 | 32 | 33 | 34 | 35 | 36 |
| NP6 | 37 | 38 | 39 | 40 | 41 | 42 |
| NP7 | 43 | 44 | 45 | 46 | 47 | 48 |
| NP8 | 49 | 50 | 51 | 52 | 53 | 54 |
| NP9 | 55 | 56 | 57 | 58 | 59 | 60 |
| NP10 | 61 | 62 | 63 | 64 | 65 | 66 |
| NP11 | 67 | 68 | 69 | 70 | 71 | 72 |
| NP12 | 73 | 74 | 75 | 76 | 77 | 78 |
| NP13 | 79 | 80 | 81 | 82 | 83 | 84 |
| NP14 | 85 | 86 | 87 | 88 | 89 | 90 |
| NP15 | 91 | 92 | 93 | 94 | 95 | 96 |
| NP16 | 97 | 98 | 99 | 100 | 101 | 102 |
| NP17 | 103 | 104 | 105 | 106 | 107 | 108 |
| NP18 | 109 | 110 | 111 | 112 | 113 | 114 |
| NP19 | 115 | 116 | 117 | 118 | 119 | 120 |
| NP20 | 121 | 122 | 123 | 124 | 125 | 126 |
| NP21 | 127 | 128 | 129 | 130 | 131 | 132 |
| NP22 | 133 | 134 | 135 | 136 | 137 | 138 |

TABLE 1-continued

Sequence identifiers (SEQ ID NOs) corresponding to the CDR sequences of specified antibodies

| | Sequence Identifier (SEQ ID NO) | | | | | |
|---|---|---|---|---|---|---|
| Antibody | CDR-L1 | CDR-L2 | CDR-L3 | CDR-H1 | CDR-H2 | CDR-H3 |
| NP23 | 139 | 140 | 141 | 142 | 143 | 144 |
| NP24 | 145 | 146 | 147 | 148 | 149 | 150 |
| NP25 | 151 | 152 | 153 | 154 | 155 | 156 |

According to some exemplary embodiments of the present disclosure, the VL domain and VH domain of NP1 to NP25 antibodies respectively comprises the amino acid sequences as summarized in Table 2.

TABLE 2

Sequence identifiers corresponding to the VL and VH sequences of specified antibodies

| Name | Domain | SEQ ID NO |
|---|---|---|
| NP1 | VL | 157 |
| | VH | 158 |
| NP2 | VL | 159 |
| | VH | 160 |
| NP3 | VL | 161 |
| | VH | 162 |
| NP4 | VL | 163 |
| | VH | 164 |
| NP5 | VL | 165 |
| | VH | 166 |
| NP6 | VL | 167 |
| | VH | 168 |
| NP7 | VL | 169 |
| | VH | 170 |
| NP8 | VL | 171 |
| | VH | 172 |
| NP9 | VL | 173 |
| | VH | 174 |
| NP10 | VL | 175 |
| | VH | 176 |
| NP11 | VL | 177 |
| | VH | 178 |
| NP12 | VL | 179 |
| | VH | 180 |
| NP13 | VL | 181 |
| | VH | 182 |
| NP14 | VL | 183 |
| | VH | 184 |
| NP15 | VL | 185 |
| | VH | 186 |
| NP16 | VL | 187 |
| | VH | 188 |
| NP17 | VL | 189 |
| | VH | 190 |
| NP18 | VL | 191 |
| | VH | 192 |
| NP19 | VL | 193 |
| | VH | 194 |
| NP20 | VL | 195 |
| | VH | 196 |
| NP21 | VL | 197 |
| | VH | 198 |
| NP22 | VL | 199 |
| | VH | 200 |
| NP23 | VL | 201 |
| | VH | 202 |
| NP24 | VL | 203 |
| | VH | 204 |
| NP25 | VL | 205 |
| | VH | 206 |

As would be appreciated, the sequence (e.g., the framework sequence) of the VL and VH domains may vary (e.g., being substituted by conserved or non-conserved amino acid residues) without affecting the binding affinity and/or specificity of the present antibody. Preferably, the sequence(s) of the VL and VH domains is/are conservatively substituted by one or more suitable conservative amino acid residue(s) with similar properties; for example, the substitution of leucine (an nonpolar amino acid residue) by isoleucine, alanine, valine, proline, phenylalanine, or tryptophan (another nonpolar amino acid residue); the substitution of aspartate (an acidic amino acid residue) by glutamate (another acidic amino acid residue); or the substitution of lysine (an basic amino acid residue) by arginine or histidine (another basic amino acid residue). Accordingly, the present antibodies (i.e., NP1 to NP25 antibodies) containing minor variations in the VL and VH sequences are also within the present disclosure.

According to some embodiments, the amino acid residues in the VL and/or VH framework of antibody NP1 is substituted by some conservative amino acid residues (i.e., conservative replacement or conservative substitution). The conservative replacement is known in the art, and a skilled artisan may choose suitable amino acid residues to replace the VL and/or VH frameworks of antibody NP1 without affect its activity. In these embodiments, the VL domain of antibody NP1 may comprise an amino acid sequence at least 85% (e.g. 85%, 86%, 87%, 88%, 89%, 90%, 91%, 92%, 93%, 94%, 95%, 96%, 97%, 98%, 99% or 100%) identical to SEQ ID NO: 157, and/or the VL domain of antibody NP1 may comprise an amino acid sequence at least 85% identical to SEQ ID NO: 158. Preferably, the VL domain of antibody NP1 comprises an amino acid sequence at least 90% identical to SEQ ID NO: 157, and/or the VL domain of antibody NP1 comprises an amino acid sequence at least 90% identical to SEQ ID NO: 158. More preferably, the VL domain of antibody NP1 comprises an amino acid sequence at least 95% identical to SEQ ID NO: 157, and/or the VL domain of antibody NP1 comprises an amino acid sequence at least 95% identical to SEQ ID NO: 158.

As would be appreciated, the conservative replacement may alternatively be conducted in the VL and/or VH frameworks of antibody NP2, NP3, NP4, NP5, NP6, NP7, NP8, NP9, NP10, NP11, NP12, NP13, NP14, NP15, NP16, NP17, NP18, NP19, NP20, NP21, NP22, NP23, NP24 or NP25 with the proviso that such the conservative replacement would not affecting the activity (e.g., the binding affinity and/or specificity to antigen) of the antibody. According to some exemplary embodiments, the VL domains of antibodies NP2, NP3, NP4, NP5, NP6, NP7, NP8, NP9, NP10, NP11, NP12, NP13, NP14, NP15, NP16, NP17, NP18, NP19, NP20, NP21, NP22, NP23, NP24 and NP25 respectively comprise amino acid sequences at least 85% identical to SEQ ID NOs: 159, 161, 163, 165, 167, 169, 171, 173, 175, 177, 179, 181, 183, 185, 187, 189, 191, 193, 195, 197, 199, 201, 203 and 205, and/or the VL domains of antibodies NP2, NP3, NP4, NP5, NP6, NP7, NP8, NP9, NP10, NP11, NP12, NP13, NP14, NP15, NP16, NP17, NP18, NP19, NP20, NP21, NP22, NP23, NP24 and NP25 respectively comprise amino acid sequences at least 85% identical to SEQ ID NOs: 160, 162, 164, 166, 168, 170, 172, 174, 176, 178, 180, 182, 184, 186, 188, 190, 192, 194, 196, 198, 200, 202, 204 and 206. Preferably, the VL domains of antibodies NP2, NP3, NP4. NP5, NP6, NP7, NP8, NP9, NP10, NP11, NP12, NP13, NP14, NP15, NP16, NP17, NP18, NP19, NP20, NP21, NP22, NP23, NP24 and NP25 respectively comprise amino acid sequences at least 90% identical to SEQ ID NOs: 159, 161, 163, 165, 167, 169, 171, 173, 175, 177, 179, 181, 183, 185, 187, 189, 191, 193, 195, 197, 199, 201, 203 and 205, and/or the VL domains of antibodies NP2, NP3, NP4, NP5, NP6, NP7, NP8, NP9, NP10, NP11, NP12, NP13, NP14, NP15, NP16, NP17, NP18, NP19, NP20, NP21, NP22, NP23, NP24 and NP25 respectively comprise amino acid sequences at least 90% identical to SEQ TD NOs: 160, 162, 164, 166, 168, 170, 172, 174, 176, 178, 180, 182, 184, 186, 188, 190, 192, 194, 196, 198, 200, 202, 204 and 206. More preferably, the VL domains of antibodies NP2, NP3, NP4, NP5, NP6, NP7, NP8, NP9, NP10, NP11, NP12, NP13, NP14, NP15, NP16, NP17, NP18, NP19, NP20, NP21, NP22, NP23, NP24 and NP25 respectively comprise amino acid sequences at least 95% identical to SEQ ID NOs: 159, 161, 163, 165, 167, 169, 171, 173, 175, 177, 179, 181, 183, 185, 187, 189, 191, 193, 195, 197, 199, 201, 203 and 205, and/or the VL domains of antibodies NP2, NP3, NP4, NP5, NP6, NP7, NP8, NP9, NP10, NP11, NP12, NP13, NP14, NP15, NP16, NP17, NP18, NP19, NP20, NP21, NP22, NP23, NP24 and NP25 respectively comprise amino acid sequences at least 95% identical to SEQ ID NOs: 160, 162, 164, 166, 168, 170, 172, 174, 176, 178, 180, 182, 184, 186, 188, 190, 192, 194, 196, 198, 200, 202, 204 and 206.

According to some examples of the present disclosure, each of the NP1 to NP25 antibodies is useful in detecting the influenza virus, and accordingly, may serve as a detecting agent for diagnosing influenza virus infection.

It is therefore another aspect of the present disclosure to provide a kit for the detection of influenza virus infection in a subject. The kit includes, at least, a container, and an antibody (i.e., a first antibody) in accordance with any aspect or embodiment of the present disclosure. Optionally, the kit may further comprise a legend indicating how to use the antibody for detecting influenza virus infection.

According to certain embodiments of the present disclosure, the antibody is NP16 antibody, which is employed as a capture agent for capturing a NPA (the nucleoprotein derived from IAV), and as a detection agent for detecting the NPA in a detection assay, such as ELISA, WB assay, flow cytometry or LFIA. According to some embodiments of the present disclosure, the antibody is NP17, which serves as a capture agent and a detection agent for detecting IAV infection.

Optionally, the kit may further comprise a second antibody, in which one of the first and second antibodies serves as a capture agent, and the other of the first and second antibodies serves as a detection agent in a detection assay. According to some embodiments, the kit comprises NP16 antibody as the detection agent, and one of the NP1, NP2, NP3, NP4, NP5, NP6 NP7, NP8, NP9, NP10, NP11, NP12, NP13, NP14, NP15, NP17, NP18, NP19, NP20, NP21, NP22, NP23, NP24 and NP15 as the capture agent, According to alternative embodiments, the kit comprises NP17 antibody as the detection agent, and one of the NP1, NP2, NP3, NP4, NP5, NP6, NP7, NP8, NP9, NP10, NP11, NP12, NP13, NP14, NP15, NP16, NP18, NP19, NP20, NP21, NP22, NP23, NP24 and NP15 as the capture agent.

Also included herein is a method of determining whether a subject is infected by an influenza virus via a biological sample isolated from the subject. The method comprises detecting the presence or absence of a nucleoprotein of the influenza virus in the biological sample by use of the antibody fragment, recombinant antibody or kit of the present disclosure, wherein the presence of the nucleoprotein indicates that the subject is infected by the influenza virus.

Basically, the biological sample is a sample obtained from the respiratory tract of the subject; preferably, the upper respiratory tract of the subject. Non-limiting examples of the biological sample suitable to be used in the present method include, a mucosa tissue, a fluid, or a secretion (e.g., sputum) isolated from the oral cavity, nasal cavity, trachea, bronchus, or lung of the subject.

Based on the diagnostic result, a skilled artisan or a clinical practitioner may administer to a subject in need thereof (e.g., a subject suffering from influenza virus infection) a suitable treatment (such as, an anti-viral treatment) thereby ameliorating and/or alleviating the symptom(s) associated with the influenza virus infection. Examples of the anti-viral treatment suitable to be used in the present method include, but are not limited to, oseltamivir, zanamivir, peramivir, baloxavir marboxil, amantadine, rimantadine, and a combination thereof.

The subject that can be subjected to the diagnosis and/or treatment methods of the present invention is a mammal, such as a human, a mouse, a rat, a monkey, a sheep, a goat, a cat, a dog, a horse, or a chimpanzee. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

Example

Materials and Methods

Preparation of Recombinant Nucleoproteins (NPs)

Five representative NPs of influenza A virus and 1 representative NP of influenza B virus were prepared in this study, including NPA1 (Accession number: AY210236; a NP derived from IAV strain A/Taiwan/1/72 (H3N2)), NPA2 (Accession number: AF306656; a NP derived from IAV strain A/WSN/1933(H1N1)), NPA3 (Accession number: CY083913; a NP derived from IAV strain A/Aalborg/INS132/2009 (H1N1)), NPA4 (Accession number: CY025384; a NP derived from IAV strain A/Alabama/UR06-0455/2007 (H1N1). NPA5 (Accession number: CY098574; a NP derived from IAV strain A/Anhui/1/2005 (1-5N)), and NPB1 (Accession number: CY018304; a NP derived from IBV strain B/Houston/B720/2004). Specifically, the coding region of NP genes were optimized for E coil expression and cloned into expression vector pET15b linearized with Nde I and Xho I restriction enzymes; the recombinant NP protein contained a $His_6$-tag and a thrombin cleavage sequence upstream to the NP sequence. These NP constructs were overexpressed in BL21 (DE3) cell with 0.5 mM isopropyl β-D-1-thiogalactopyranoside (IPTG) induction at 16° C. The NP recombinant protein expressed in *E. coli* was purified using $Ni^{2+}$ charged chelating sepharose column (for $His_6$-tag binding), heparin column (for RNA-free NP binding), and size exclusive separation with buffer containing 40 mM Tris, pH 7.5, 600 mM NaCl. To obtain the NP protein free of RNA, RNaseA (20 μg/ml) was applied to cell lysis of *E. coli*, followed by the purification procedures. Purified NP proteins were confirmed by sodium dodecyl sulfate polyacrylamide gel electrophoresis (SDS-PAGE). The thus-obtained NP proteins respective comprised amino acid sequences of SEQ ID NO: 1 (NPA1), SEQ ID NO: 2 (NPA2), SEQ ID NO: 3 (NPA3), SEQ ID NO: 4 (NPA4), SEQ ID NO: 5 (NPA5) and SEQ ID NO: 6 (NPB1).

Cell Lines

MDCK (Madin-Darby canine kidney, ATCC CCL-34) epithelial cells were cultured in MEM medium supplemented with NEAA (non-essential amino acids), 2 mM L-glutamine, and 10% fetal bovine serum (FBS) at 37° C. in a 5% ($CO_2$ humidified atmosphere incubator. 293-T cells (ATCC CRL-3216) were cultured in DMEM medium supplemented with 10% FBS, penicillin-streptomycin (100×). Suspension 293-F cells were cultured in serum free 293 expression medium at 37° C. with shaking 110 rpm in 8% $CO_2$ incubator.

Viruses

Six influenza A viruses were used in this study, including, (1) H1N1 Brisbane (A/Brisbane/59/2007 (H1N1/H1B)); (2) H1N1 Swine (a recombinant virus NYMC X-181 derived from A/California/07/2009(H1N1/H1S)); (3) H3N2 Brisbane (A/Brisbane/10/2007(H3N2/H3B) (4) H3N2 Wisconsin (A/Wisconsin/67/2005(H3N2/H3W)); (5) H5N1 Vietnam (a recombinant virus NIBRG-14 derived from A/VietNam/1194/2004(H5N1/H5V)); and (6) Flu B (B/Brisbane/60/2008(fluB)). Viruses' stocks were propagated in 10-day-old embryonic eggs' allantoic cavities for 60 hours and then harvested, concentrated by ultracentrifugation (25,000×g for 2 hours) and resuspended in phosphate-buffered saline (PBS). The virus titers and TCID50 (50% tissue culture infectious dose) were determined with cultured MDCK cells. In brief, the virus stocks were 10-fold diluted by MEM-NEAA medium supplied with TPCK-treated trypsin (1 g/ml) and 0.3% bovine serum albumin (BSA, infection buffer). Diluted virus samples were incubated with PBS-washed MDCK cells ($1\times10^4$ cells per well in a 96-well plate) for 1 hour. After absorption, the virus suspensions were removed, and MDCK cells were washed by PBS twice. Infected MDCK cells were cultured in fresh infection buffer for either 3 days (H1N1 Swine, H3N2 Brisbane and H3N2 Wisconsin) or 5 days (H1N1 Brisbane, H5N1 Vietnam and Flu B). Survival MDCK cells were fixed with ice-cold methanol-acetone (1:1 (v/v)) and stained with 0.5% crystal violet, and the TCID50 were calculated.

Characterization of the IgG1s Derived from the Selection and Screening Procedure with Phage-Displayed Synthetic scFv Libraries The construction and characterization of the phage-displayed synthetic scFv libraries followed the same procedure, without modification, as described in the U.S. Pat. No. 10,336,815 B2 or U.S. Pat. No. 10,336,816 B2 and the publication of Ing-Chien Chen et al. (High throughput discovery of influenza virus neutralizing antibodies from phage-displayed synthetic antibody libraries, Scientific Reports 7, Article number: 14455 (2017)). The experimental procedures for panning the phage display libraries, selecting and screening of phage-displayed scFv binders, characterizing the scFvs binding to the cognate antigens and protein A/L with ELISA, reformatting scFvs into IgG1s, expressing and purifying IgG1s, and determining $EC_{50}$ for the antibody-antigen interaction with ELISA have been described in the U.S. Pat. Nos. 10,336,815 B2 or 10,336,816 B2.

IgG Binding to NP/from Virus Infected MDCK Cells

MDCK cells ($3\times10^4$ cells/well) were seeded in 96-well plates for 16 hours and washed twice with PBS prior to be infected by 100×TCID50 viral solution. Infected MDCK cells were cultured for 24 hours and then fixed with methanol-acetone (1:1 (v/v)). A serial 2-fold diluted anti-influenza viral nucleoprotein IgG antibodies were used to detect viral nucleoprotein production with goat anti-human IgG-Fc antibody conjugated with horseradish peroxidase (HRP; 1:5000 dilution) or goat anti-mouse antibody conjugated with HRP (1:1000 dilution). Colorimetric measurements were carried out after the color development by adding 3,3'5,5'-tetramethylbenzidine (TMB) substrate (100 μL per well) to each well for 5 minutes before adding 1 N HCl (100 μL per well) to stop the chromogenic reaction. The absorbance at 450 nm was measured after each concentration of diluted IgG was assayed with triplicate. $EC_{50}$ was calculated.

Detection of NPs from Lysed Influenza Virus with Sandwich ELISA

HRP was conjugated to detection antibody with HRP conjugation kit. 200 μg of purified IgG was added to HRP mix with molar ratio of IgG:HRP=1:2, and the conjugation reaction was quenched according to manufacturer's instruction. Sandwich ELISAs were carried out with 96-well plate, which was coated with purified capture IgG (1 μg per well) at 4° C. overnight. NP from influenza virus was accessible in solution by lysing the virus with lysis buffer (PBS+0.1% Tween-20+0.1% N-Lauroylsarcosine) for 1 hour. The NPs from lysed viruses were quantified by running the query NPs through 12% NuPAGE Bis-Tris gels at 120 V for 3 hours. The gels were stained with coomassie brilliant blue. The query NPs were quantified with software, and the correlation of the coomassie brilliant blue intensity versus the concentrations of the purified recombinant NPs. The quantified NPs from lysed influenza viruses were added to each well coated with capture antibody for one hour. After washing, 0.1 μg/ml HRP conjugated detection IgG (100 μL per well) was added to each well. The color was developed by adding TMB (100 μL per well) to each well for 5 minutes before adding 1 N HCl (100 μL, per well) to stop the chromogenic reaction before the absorbance at 450 nm was measured. $EC_{50}$ was calculated.

Preparation of Colloidal Gold Conjugated AL2C and IgGs

100 μl of 0.2 M $K_2CO_3$ (pH 11.5) was mixed with 10 ml colloidal gold solution (pH5-6) to adjust pH (final pH 9), and then add 500 μl of IgG (1 mg/ml) or 50 μl of AL2C (3.35 mg/ml) to the colloidal gold solution for 40 minutes at room temperature. Add 1 ml of blocking buffer (10% BSA in 20 mM sodium borate, pH9.3) for 15 minutes at room temperature, followed by centrifugation (15,000 g, 30 minutes, 4° C.). The supernatant was discarded, and the pellet was completely resuspended in 10 ml wash buffer (1% BSA in 20 mM sodium borate, pH9.3), followed by centrifugation (15,000 g, 30 minutes, 4° C.). The washing procedure was repeated two times, and the pellet was resuspended in 1 ml 1% BSA in 20 mM sodium borate (pH9.3) for the procedure preparing the conjugate pad.

Assembly of the LFIA Strips

One μg of the capture antibody, antigen or AL2C in PBS buffer were stripped on NP membrane per cm with lateral flow dispenser driven by syringe infusion pump. All other procedures for the preparation of the NC membrane with immobilized antigen or capture antibody, the preparation of the conjugate pad and the sample pad, and the preparation of the LFIA strip assembly were followed the protocol previously reported.

Example 1 Representative Influenza NPs Derived from Phylogenetic Analysis of NP Sequences in Database were Used as Target Antigens for Anti-NP Antibody Discoveries In order to develop antibodies as affinity reagents capable of characterizing the majority of NPs from diverse strains of IAV and IBV, a panel of NPs was established to represent, as broadly as possible, the NPs in nature as target antigens. 26,207 influenza virus NP sequences were clustered from the Influenza Research Database by software, and the sequence identity threshold was 95% (data not shown). Out of the total of 48 clusters resulting from the clustering algorithm, the top 5 NPA (influenza A virus NP) clusters encompassed 91% of the total NPA sequences and one NPB (influenza B virus NP) cluster for all NPB sequences from the database (data not shown). This result is in agreement with the previously published phylogenetic analysis indicating that the NPA sequences can be phylogenetically grouped into only a few major clusters. The consensus sequences of the top NPA and NPB clusters were used to search in the NCBI protein sequence database for representative NP sequences. Six representative NPs (including NPA1 to NPA5 and NPB1) were selected and expressed as recombinant proteins respectively in *E. coli* harboring the chemically synthesized corresponding gene, and then purified to more than 95% purity for the following phage display antibody discovery procedure. The pairwise sequence identity between the six NPs was summarized in Table 3.

TABLE 3

The pairwise sequence identities of the NP sequences of specified proteins or viruses

| NP antigen | NPA1 | NPA2 | NPA3 | NPA4 | NPA5 | A/ Brisbane/ 59/2007 (H1N1/ H1B) | A/ Brisbane/ 10/2007 (H3N2/ H3B) | A/ Wisconsin/ 67/2005 (H3H2/ H3W) | A/ California/ 07/2009 (H1N1/ H1S) | A/ Vietnam 1194/ 2004 (H5N1/ H5V) | NPB1 | B/ Brisbane/ 60/2008 (fluB) |
|---|---|---|---|---|---|---|---|---|---|---|---|---|
| NPA1 | — | 93.5% | 89.7% | 92.5% | 90.5% | 92.3% | 92.3% | 91.5% | 91.3% | 91.9% | 34.2% | 34.4% |
| NPA2 | 93.5% | — | 92.7% | 94.3% | 94.1% | 94.1% | 94.1% | 97.1% | 96.9% | 97.1% | 34.8% | 34.9% |
| NPA3 | 89.7% | 92.7% | — | 89.9% | 94.3% | 90.1% | 90.1% | 91.5% | 91.3% | 91.7% | 34.6% | 34.8% |
| NPA4 | 92.5% | 94.3% | 89.9% | — | 92.1% | 99.7% | 99.7% | 93.3% | 93.1% | 93.1% | 35.1% | 35.3% |
| NPA5 | 90.5% | 94.1% | 94.3% | 92.1% | — | 91.9% | 91.9% | 92.9% | 92.7% | 93.1% | 34.4% | 34.6% |
| A/Brisbane/ 59/2007 (H1N1/H1B) | 92.3% | 94.1% | 90.1% | 99.7% | 91.9% | — | 100% | 93.3% | 93.1% | 92.9% | 35.3% | 35.5% |
| A/Brisbane/ 10/2007 (H3N2/H3B) | 92.3% | 94.1% | 90.1% | 99.7% | 91.9% | 100% | — | 93.3% | 93.1% | 92.9% | 35.3% | 35.5% |
| A/Wisconsin/ 67/2005 (H3N2/H3W) | 91.5% | 97.1% | 91.5% | 93.3% | 92.9% | 93.3% | 93.3% | — | 99.7% | 99.3% | 34.0% | 34.2% |
| A/California/ 07/2009\ (H1N1/H1S) | 91.3% | 96.9% | 91.3% | 93.1% | 92.7% | 93.1% | 93.1% | 99.7% | — | 99.1% | 34.0% | 34.2% |
| A/Vietnam/ 1194/2004 (H5N1/HSV) | 91.9% | 97.1% | 91.7% | 93.1% | 93.1% | 92.9% | 92.9% | 99.3% | 99.1% | — | 34.2% | 34.4% |
| NPB1 | 34.2% | 34.8% | 34.6% | 35.1% | 34.4% | 35.3% | 35.3% | 34.0% | 34.0% | 34.2% | — | 99.6% |
| B/Brisbane/ 60/2008 (fluB) | 34.4% | 34.9% | 34.8% | 35.3% | 34.6% | 35.5% | 35.5% | 34.2% | 34.2% | 34.4% | 99.6% | — |

selection and screening against the recombinant antigens have been documented previously, e.g., seeing the procedure described in U.S. Pat. No. 10,336,815 B2 or U.S. Pat. No. 10,336,816 B2. The selected phage-displayed libraries after 2 or 3 rounds of selection cycle with polyclonal scFv secretions in the culture media showing positive responses to the corresponding antigen with ELISA were expected to contain enriched candidate scFv populations binding to the corresponding antigen. These phage-displayed scFv libraries were mixed as input for another 2 rounds of phage display selection cycle, where the recombinant NPs other than the target NP immobilized on the solid surface were added in excess amount to the solution phase during the phage particle binding to the immobilized target NP. The purpose of these two additional selection rounds was to enrich the population of scFvs binding only to the target NP but not to the other NPs in the solution phase. Soluble monoclonal scFvs randomly selected from the output libraries of these two selection cycles were screened for binding to protein A

Example 2 an Antibody Discovery Procedure was Designed to Develop a Panel of Anti-NP IgGs with Diverse Specificities to the Representative NPs To differentiate the subtype of the influenza viruses, a panel of antibodies with distinct binding patterns to the respective NP of the representative influenza viruses was established. A novel procedure was used in the present study for discovering antibodies for sandwich ELISA and LFIA capable of detecting and distinguishing NPs from diverse strains of IAV. Specifically, for each of the target NPs (i.e., NPA1, NPA2, NPA3, NPA4, NPA5 or NPB1), the antibody discovery procedure started by 3 rounds of standard phage display selection, using 16 GH synthetic antibody libraries respectively. The technical details of the construction of the GH phage-displayed synthetic antibody libraries and the standard procedure for phage-displayed antibody library and protein L, and to the respective NP with ELISA; scFvs with positive binding signals to protein A, protein L and cognate NP were reformatted into IgGs with the human IgG1 framework. These IgG1s were expressed with mammalian expression system and purified with protein A column, and then tested for antigen binding specificity and affinity with ELISA and LFIA.

Example 3 a Panel of Antibody-Based Affinity Reagents with Diverse Specificities to the Representative NPs were Selected and Screened from the Phage-Displayed Synthetic Antibody Libraries A total of 753 positive monoclonal anti-NP scFvs (ELISA $OD_{450\ nm}$>0.5 binding to protein A, protein L and corresponding target NP) were attained from the step of the screening procedure. Each of these 753 monoclonal scFvs was tested for cross-binding to all the 6 NPs; the data of heat map indicated the ELISA $OD_{450\ nm}$ results for each of the 753 scFvs binding to the 6 NPs (data not shown). The heat map was organized according to the grouping of the cross-binding pattern of the scFvs (y-axis of the heat map) to the 6 NPs (x-axis of the heat map). Based on the grouping of the scFv-NP binding pattern, 25 scFvs were selected to represent the major groups of the scFvs. The CDR sequences and the VL and VH sequences of these 25 scFvs were respectively summarized in Tables 1 and 2. The 25 scFvs were reformatted into human IgG1s via being expressed with the 293-F expression system and purified with protein A column followed by SDS-PAGE analysis.

Example 4 the Anti-NP IgG1s Bound to the Recombinant NPs with Diverse Specificity and High Affinity The binding specificity and affinity of the 25 anti-NP IgG1s against the 6 NPs were measured quantitatively in terms of half maximal effective concentration $EC_{50}$, and were compared with those of the commercially available mouse monoclonal anti-NP antibodies as positive controls. As the data summarized in Table 4, the antibodies with the highest affinity binding to the corresponding recombinant NP with sub-nanomolar $EC_{50}$'s were derived from the phage-displayed GH synthetic antibody libraries with the procedure described above without further affinity refinement. In comparison with the control positive antibody (MAB8251) with broad specificity to NPAs, NP16 and NP17 exhibited broad specificity as the control positive antibody with comparable affinity (Table 4). More importantly, the GH IgG1s with specific affinity to individual NPA1-NPA5 and NPB1, such as NP24-NPB1, NP3-NPA1, NP18-NPA2, NP15-NPA2, NPA4, NP8-NPA3/NPA2 and NP13-NPA4/NPA5 (Table 4), enabled affinity reagent-based profiling of NPs from unknown strains of IAV/IBV.

TABLE 4

The $EC_{50}$'s (nM) derived from the sigmoidal binding curves of the 25 ant-NP IgG1s binding to specified recombinant NPs

| | NPA1 | NPA2 | NPA3 | NPA4 | NPA5 | NPB1 |
|---|---|---|---|---|---|---|
| NP1 | NC | | | | | |
| NP2 | | | | | | 1.37 |
| NP3 | 0.09 | | | | | |
| NP4 | 0.19 | | 10.11 | | 0.37 | |
| NP5 | 1.69 | 0.13 | | | | |
| NP6 | | | | | | |
| NP7 | | 0.79 | | | | |
| NP8 | | 2.14 | 0.07 | | | |
| NP9 | | | 4.38 | | 1.12 | |
| NP10 | 0.36 | | NC | NC | 0.28 | |
| NP11 | | 0.27 | | | 0.06 | |
| NP12 | | | | | 9.07 | |
| NP13 | | | 9.36 | 0.07 | 0.09 | |
| NP14 | 0.19 | 0.08 | 19.71 | | 1.70 | |
| NP15 | NC | 0.45 | | 0.35 | | |
| NP16 | 0.09 | | 0.96 | 0.18 | 0.09 | |
| NP17 | 0.08 | 0.06 | | 0.03 | 0.17 | |
| NP18 | | 0.20 | | | | |
| NP19 | 0.11 | NC | | | | |
| NP20 | | | | | | 0.04 |
| NP21 | 0.12 | 28.63 | | | | |
| NP22 | | | | | | 0.27 |
| NP23 | | | | | | 0.06 |
| NP24 | | | | | | 0.05 |
| NP25 | | | | | | 0.10 |
| MAB8251 | 0.12 | 0.13 | 0.13 | 3.68 | 0.16 | NC |

TABLE 4-continued

The $EC_{50}$'s (nM) derived from the sigmoidal binding curves of the 25 ant-NP IgG1s binding to specified recombinant NPs

| | NPA1 | NPA2 | NPA3 | NPA4 | NPA5 | NPB1 |
|---|---|---|---|---|---|---|
| ab47876 | | | | | | 0.13 |
| NBP2-23514 | | | | | | 0.11 |
| MAB8259 | | | | | | 0.27 |

Blank: No ELISA signals with 10 μg/ml IgG.
NC: curve fitting failed (Not converged, interrupted)

Example 5 IAV Subtype NPs in Virus-Infected MDCK Cells were Differentiated with the Panel of Anti-NP IgG1s To test the capability of the panel of 25 anti-NP IgG1s in differentiating NPs from IAV and IBV, ELISA measurements were carried out to detect and differentiate the closely related NPs expressed in MDCK cells infected by 5 vaccine strain IAVs and 1 vaccine strain IBV. Two groups of NPs were found in the 5 vaccine strain IAVs: the first group contained the NPs of A/Brisbane/59/2007(H1N1/H1B) and A/Brisbane/10/2007(H3N2/H3B), which were identical in amino acid sequence and different from NPA4 by one residue (99.7% sequence identity; Table 3); the second group contained the NPs of A/Wisconsin/67/2005(H3N2/H3W), A/California/07/2009(H1N1/H1S) and A/VietNam/1194/2004(H5N1/H5V), which were different in amino acid sequence identity by at most 4 residues. The second group of NPs were similar to NPA2 with about 97% sequence identity (Table 3). The NP of the vaccine strain IBV (B/Brisbane/60/2008(fluB)) was different from NPB1 by one amino acid residue (99.7% sequence identity; Table 3).

The binding of each of the 25 anti-NP IgG1s to the NPs was examined in immobilized MDCK cells pre-infected respectively with the 5 IAV and 1 IBV vaccine strains, and the results were summarized in Table 5. Although the NPs expressed in virus-infected MDCK cells were not expected to completely resemble to the purified recombinant NPs in terms of NP-RNA complex and homo-polymer formation, still the data of Table 5 was compared to that of Table 4. The $EC_{50}$'s of the anti-NP IgG1s with the highest affinity binding to the corresponding NP in the virus-infected MDCK cells were comparable to those of the control positive antibodies, indicating that at least a subset of the 25 anti-NP IgG1s were able to bind to the NPs in the influenza virus-infected MDCK cells as effectively as the control positive antibodies (Table 5). However, the specificities of the 25 anti-NP IgG1s against the NPs in MDCK cells infected by H1B and H3B were not exactly comparable with those against recombinant NPA4 (Table 5), the sequence of which was different from the NPs of HIB and H3B only by one amino acid residue (sequence identity 99.7%). Specifically, NP15 and NP16 consistently recognized recombinant NPA4 and the NPs in MDCK cell infected by HIB and H3B with high affinity, but similar consistency did not occur for NP13 and NP17, which recognized recombinant NPA4 with high affinity but failed to bind to the NPs in MDCK cell infected by HIB and H3B with observable affinity Table 5. In addition, NP3, NP9, NP12, NP14 and NP19, which did not have observable affinity to NPA4 (Table 4), recognized the NPs in MDCK cell infected by H1B and H3B with observable affinity (Table 5).

TABLE 5

The $EC_{50}$'s (nM) derived from the sigmoidal binding curves of the 25 ant-NP IgG1s binding to specified NPs in the influenza virus-infected MDCK cells

| | A/California/ 07/2009 (H1N1/H1S) | A/Brisbane/ 59/2007 (H1N1/H1B) | A/Brisbane/ 10/2007 (H3N2/H3B) | A/Wisconsin/ 67/2005 (H3H2/H3W) | A/Vietnam 1194/2004 (H5N1/H5V) | B/Brisbane/ 60/2008 (fluB) |
|---|---|---|---|---|---|---|
| NP1 | NC | NC | NC | NC | 5.89 | NC |
| NP2 | | | | NC | NC | 4.89 |
| NP3 | 0.55 | 0.521 | 0.301 | 0.25 | 0.393 | NC |
| NP4 | 4.02 | 14.1 | 63.1 | 4.82 | NC | NC |
| NP5 | NC | NC | NC | NC | NC | NC |
| NP6 | 6.46 | NC | NC | NC | NC | NC |
| NP7 | NC | NC | NC | | NC | NC |
| NP8 | | | NC | NC | NC | |
| NP9 | 2.14 | 2.95 | 0.891 | 2.35 | 2.14 | NC |
| NP10 | NC | NC | NC | | 1 | 14.5 |
| NP11 | NC | NC | | | NC | |
| NP12 | 6.09 | 5.09 | 0.399 | 0.333 | 0.189 | NC |
| NP13 | 1.677 | NC | NC | 5.633 | 7.17 | NC |
| NP14 | 3.43 | 0.228 | 0.246 | NC | | NC |
| NP15 | 0.249 | 0.668 | 0.563 | 0.449 | 0.525 | NC |
| NP16 | 0.239 | 0.21 | 0.21 | 0.248 | 0.501 | NC |
| NP17 | 28.7 | NC | NC | | NC | NC |
| NP18 | 0.168 | 7 | 6.82 | 0.192 | 0.292 | |
| NP19 | 0.304 | 0.295 | 0.39 | 0.215 | 0.386 | NC |
| NP20 | NC | NC | NC | | NC | 4.88 |
| NP21 | 0.73 | 4.6 | 74.1 | NC | 13.7 | NC |
| NP22 | | 7.11 | NC | | NC | 3.92 |
| NP23 | NC | NC | NC | NC | NC | |
| NP24 | | | | NC | NC | 3.17 |
| NP25 | NC | 4.83 | NC | NC | NC | 2.17 |
| MAB8251 | 0.0813 | 0.08 | 0.131 | 0.085 | 0.316 | NC |
| ab47876 | NC | | NC | NC | NC | 2.06 |
| NBP2-23514 | | NC | NC | NC | | 3.7 |
| MAB8259 | NC | NC | | | NC | 9.09 |

Blank: No ELISA signals with 10 μg/ml IgG.
NC: curve fitting failed (Not converged, interrupted)

The anti-NP IgG1-NP binding patterns were able to differentiate closely related NPs expressed in MDCK cells (Table 5). Not only the binding patterns of these anti-NP IgG1s to the NPs distinguished the NP of IBV from those of IAVs, the NPs from the subtypes of the IAVs were differentiable on the basis of the IgG1-NP binding patterns (Table 5), which led to correct grouping of the NPs of A/Brisbane/59/2007(H1N1/H1B) and A/Brisbane/10/2007(H3N2/H3B) with sequence identity of 100% and the NPs of A/Wisconsin/67/2005(H3N2/H3W) and A/Viet Nam/1194/2004 (H5N1/H5V) with sequence identity of 99.3% (Table 3). These two groups of NPs were different in sequence identity by about 93%, which was correctly reflected in the grouping of the NPs based on the binding patterns of the anti-NIP IgG1s to the NPs (Data not shown). Still, the discrepancy between the grouping for A/California/07/2009(H1N1/H1S) based on the antibody binding patterns and the grouping based on the sequence identities indicated the limitation in attempting to distinguish closely related NPs (about 93% in sequence identity) with the antibody-NP binding patterns.

Example 6 Sandwich ELISA Based on the Panel of Anti-NP IgG1s were Capable of Detecting and Differentiating Subtype NPs from Lysed IAVs with Detection Limit of about 1 nM To further investigate the anti-NP IgG1s' specificities and affinities to the NPs in lysed IAVs, the $EC_{50}$'s of virus NPs was measured using the sandwich ELISA with the capture and detection antibodies from the panel of 25 anti-NP IgG1s. Again, the NPs from the lysed IAVs were not expected to completely resemble to the purified recombinant NPs and the NPs in the IAV-infected MSCD cells in terms of NP-RNA complex and homo-polymer formation, hence the capture-detection pairs of antibodies used in the sandwich ELISA for quantitative detection of the NPs from the lysed IAVs had to be determined empirically. Each of the 25 anti-NP IgG1s was used as capture antibodies, and the NPs from the lysed IAVs were detected using the HRP-conjugated NP16 or NP17 as detection antibody in the sandwich ELISA. The analytic results were respectively summarized in Table 6 (using NP16 as the detection antibody) and Table 7 (using NP17 as the detection antibody). The data of Tables 6 and 7 were highly similar, confirming that both NP16 and NP17 were competent as detection antibodies in recognizing the virus NPs from the lysed IAVs. NP17 and NP16 as both the capture and detection antibody can detect NPAs because of the formation of homo-polymer of the NPs. The detection limit of the NPs from lysed influenza virus with the sandwich ELISA was on the order of 1 nM of virus NP. Moreover, the differentiation of the NPs from the subtypes of the IAVs based on the sandwich ELISA binding patterns was largely in agreement with the phylogenetic analysis of these vaccine strain NPs (data not shown). These results established the usefulness of the sandwich ELISA with the panel of antibody-based affinity reagents as capture/detection antibodies in determining the quantity and subtype of NP from lysed influenza virus.

TABLE 6

The $EC_{50}$'s (nM) of the viral NPs derived from the sigmoidal binding curves of the sandwich ELISAs with HRP-conjugate d NP16 as detection antibody and the 25 anti-NP IgGs as capture antibodies

| | A/California/ 07/2009 (H1N1/H1S) | A/Brisbane/ 59/2007 (H1N1/H1B) | A/Brisbane/ 10/2007 (H3N2/H3B) | A/Wisconsin/ 67/2005 (H3H2/H3W) | A/Vietnam 1194/2004 (H5N1/H5V) | B/Brisbane/ 60/2008 (fluB) |
|---|---|---|---|---|---|---|
| NP1 | NC | NC | NC | NC | NC | NC |
| NP2 | NC | NC | NC | NC | NC | NC |
| NP3 | 1.955 | 2.36 | 3.433 | 1.812 | 2.015 | NC |
| NP4 | 2.11 | 2.337 | 3.398 | 2.263 | 2.31 | |
| NP5 | 3.321 | 4.02 | 5.496 | 3.128 | 3.498 | NC |
| NP6 | 3.119 | 78.31 | NC | 2.696 | 3.037 | |
| NP7 | 2.358 | 4.133 | 8.086 | 2.26 | 2.247 | NC |
| NP8 | 2.328 | NC | NC | 2.602 | 2.636 | |
| NP9 | 53.94 | NC | NC | NC | NC | NC |
| NP10 | 3.297 | 3.967 | 4.592 | 3.202 | 3.376 | |
| NP11 | NC | NC | NC | | NC | NC |
| NP12 | NC | NC | NC | NC | NC | NC |
| NP13 | 168 | 135 | 59.29 | | 54.1 | |
| NP14 | NC | | NC | NC | NC | NC |
| NP15 | 2.789 | 4.608 | 6.221 | 2.525 | 2.815 | |
| NP16 | 4.408 | 4.739 | 6.247 | 4.096 | 4.333 | NC |
| NP17 | 3.277 | 4.083 | 4.406 | 3.087 | 3.251 | |
| NP18 | NC | NC | NC | NC | NC | NC |
| NP19 | 5.373 | 3.368 | 4.017 | 3.876 | 3.967 | NC |
| NP20 | NC | NC | NC | NC | NC | NC |
| NP21 | 2.671 | 2.71 | 3.535 | 2.882 | 2.791 | |
| NP22 | NC | 59.44 | NC | 91.4 | NC | NC |
| NP23 | | NC | NC | NC | NC | NC |
| NP24 | | NC | NC | NC | NC | |
| NP25 | NC | NC | NC | NC | NC | |

Blank: No ELISA signals with 10 μg/ml IgG.
NC: curve fitting failed (Not converged, interrupted)

TABLE 7

The $EC_{50}$'s (nM) of the viral NPs derived from the sigmoidal binding curves of the sandwich ELISAs with HRP-conjugate d NP17 as detection antibody and the 25 anti-NP IgGs as capture antibodies

| | A/California/ 07/2009 (H1N1/H1S) | A/Brisbane/ 59/2007 (H1N1/H1B) | A/Brisbane/ 10/2007 (H3N2/H3B) | A/Wisconsin/ 67/2005 (H3H2/H3W) | A/Vietnam 1194/2004 (H5N1/H5V) | B/Brisbane/ 60/2008 (fluB) |
|---|---|---|---|---|---|---|
| NP1 | NC | NC | NC | NC | NC | NC |
| NP2 | NC | NC | NC | NC | NC | NC |
| NP3 | 0.834 | 1.037 | 1.603 | 0.8276 | 0.8614 | NC |
| NP4 | 0.8618 | 0.9107 | 1.288 | 0.867 | 0.8747 | |
| NP5 | 0.9178 | 1.825 | 3.167 | 0.8789 | 0.909 | |
| NP6 | 3.07 | NC | NC | 1.983 | 2.719 | NC |
| NP7 | 0.8998 | 4.152 | 5.861 | 0.8206 | 0.8792 | |
| NP8 | 0.7521 | NC | NC | 0.8545 | 0.9226 | NC |
| NP9 | NC | NC | NC | 106.3 | NC | NC |
| NP10 | 0.7976 | 0.8732 | 1.058 | 0.8422 | 0.8602 | NC |
| NP11 | NC | NC | NC | NC | NC | NC |
| NP12 | NC | NC | NC | NC | NC | NC |
| NP13 | 47.88 | 27.87 | 11.03 | 35.78 | 28.95 | NC |
| NP14 | NC | NC | NC | NC | NC | |
| NP15 | 0.8056 | 0.926 | 1.133 | 0.7792 | 0.7976 | NC |
| NP16 | 0.9193 | 0.89 | 0.9594 | 0.891 | 0.8361 | NC |
| NP17 | 1.024 | 2.218 | 3.333 | 1.072 | 1.195 | |
| NP18 | NC | 66.44 | 1000 | 1000 | 1000 | NC |
| NP19 | 0.8634 | 0.8117 | 0.9426 | 0.7655 | 0.8141 | NC |
| NP20 | NC | NC | NC | NC | NC | NC |
| NP21 | 0.815 | 0.81 | 1.062 | 0.8475 | 0.8791 | NC |
| NP22 | NC | 102.4 | 98.22 | 82.84 | NC | NC |
| NP23 | NC | NC | NC | NC | NC | NC |
| NP24 | NC | NC | NC | NC | NC | NC |
| NP25 | NC | NC | NC | NC | NC | NC |

Blank: No ELISA signals with 10 μg/ml IgG.
NC: curve fitting failed (Not converged, interrupted)

The NP from the lysed IAV resembled only to an extent to the corresponding NP expressed in virus-infected MDCK cells or *E. coli*. Comparing the results in Tables 4, 6 and 7, it is found that NP13, NP15, NP16 and NP17 consistently recognized recombinant NPA4 and the virus NPs from HIB and H3B with high affinity. However, NP3, NP4, NP5, NP7, NP10, NP19 and NP21, which did not have observable affinity to NPA4 (Table 4), recognized virus NPs from H1B and H3B with high affinity measured with the sandwich ELISA (Tables 6 and 7). On the other hand, NP3, NP15, NP16 and NP19 recognized NPs from lysed virus and from virus-infected MDCK cells, but nevertheless, NP9, NP12 and NP14, which recognized NPs in H1B- and H3B-infected MDCK cells, did not have observable affinity to the corresponding NPs in the lysed IAVs (Table 4), recognized virus NPs from HIB and H3B with high affinity measured with the sandwich ELISA (Tables 6 and 7). Although the NPs from the three preparations share common epitopes in the light that NP15 and NP16 recognized the corresponding NPs from the three different preparations, the recognition discrepancies described above also highlight the differences of the antigens due to the expression hosts.

Example 7 Antibodies Derived from the GH Synthetic Antibody Libraries are Applicable to Develop LFIA Devices To test the LFIA applicability of the anti-NP IgG1s derived from the GH phage-displayed synthetic antibody libraries, the IgG1-NP binding was detected by LFIA. Each of the LFIAs shown in FIG. 1A was stripped with positive control (AL2C; a fusion protein of protein A and protein L known to bind to human IgG1 encoding the gene of the human variable domain IGHV3 and IGKV1) and NPs: NPB1 NPA1 and NPA2. The conjugate pad was incorporated with colloidal gold-labelled AL2C, and the solutions of the NP1-25 IgG1s and the positive control IgGs were applied respectively to the sample pad. The strength of the signature signals at each test lines indicated the preference of the corresponding antibody-antigen interaction, which was in qualitative agreement with the specificities of the anti-NP IgG1s and the control IgGs (data not shown).

Figure 1B:
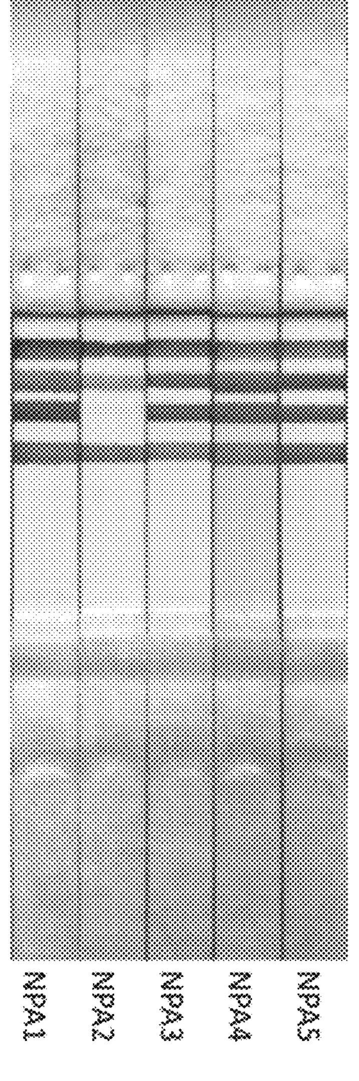

To elucidate the detection limit and specificity of the sandwich LFIAs in detecting NPs, four lines on the nitrocellulose membrane were stripped for the sandwich LFIA construct: positive control (AL2C) for IgG1 binding, NP17, NP1 and NP16 as capture antibodies (FIGS. 1B and 1C) and colloidal gold-conjugated NP17 was applied as detection antibody to the conjugate pad. Based on the results of FIG. 1A, the IgG1s were selected because of their specificity and affinity to NPA1-5. Solutions of NPA1 to NPA5 were applied respectively to the sample pad. The antigen combining the gold-labelled detection antibodies in the conjugate pad moved on to the test lines, forming sandwich immune-complex with the corresponding capture antibodies to generate the purple colorimetric signals in the test lines. As expected, the NP17 and NP16 had broad specificity against all the NPA1 to NPA5 tested (FIG. 1B) with strong affinity, as indicated in the results in Tables 6 and 7. Similar to the results in sandwich ELISA (Table 7), NP17 as both the capture and detection antibody can detect NPAs because of the formation of homo-polymer of the NPs. Unexpectedly, while NP1 was expected to have barely measurable affinity only to NPA1 based on the ELISA measurements (Table 4) and to have low affinity to both NPA1 and NPA2 based on the LFIA measurements (FIG. 1A), NP1 bound to all NPAs, except NPA2, as strongly as the other two IgG1s tested (FIG. 1B).

Figure 1C:
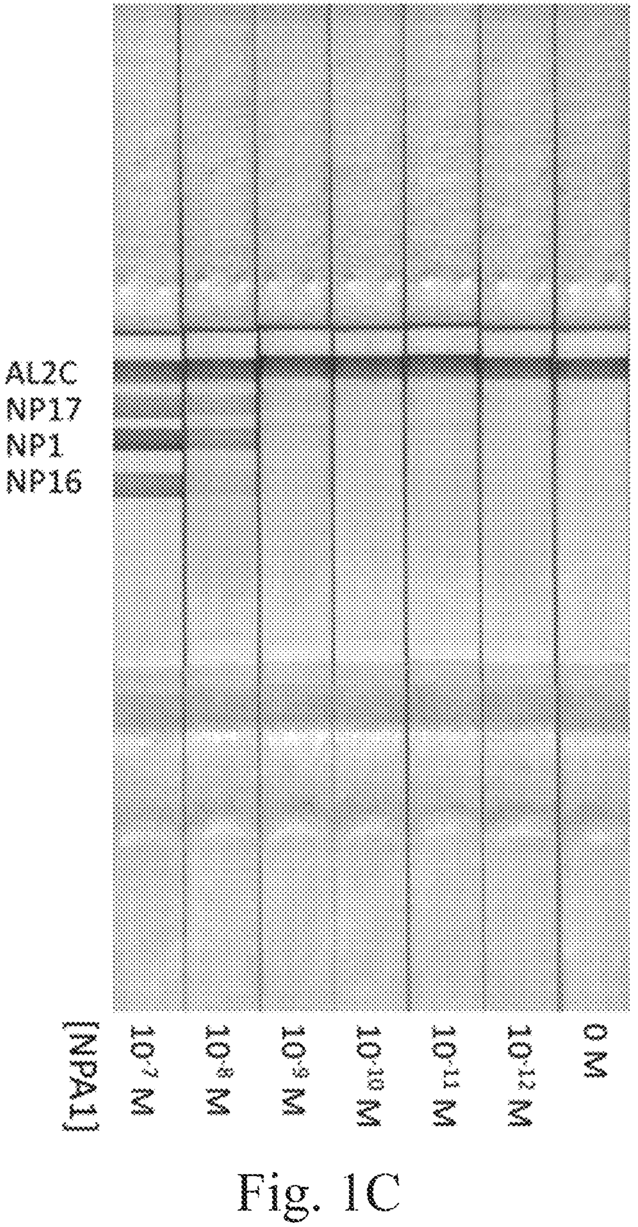

The data of FIG. 1C indicated the detection limit of the sandwich LFIA with 10-fold serial dilutions of NPA1. The LFIA detection limits for NPA1 with NP16 and NP17 was on the order of 1 nM, which was comparable to the detection limits of the IgG1s to the closely related NPAs with sandwich ELISA summarized in Tables 6 and 7. NP1 bound to NPA1 as strongly as the other two IgG1s tested (FIG. 1B), although the ELISA-based $EC_{50}$ of NP1-NPA1 interaction was at least 4 orders of magnitude inferior to those of NP16-NPA1 and NP17-NPA1 interactions, Together, the results indicate that while antibody-antigen interactions could be quantitatively accessed with ELISA and LFIA, the applicability of the antibodies in ELISA and LFIA was not necessarily correlated; hence antibodies for optimal LFIA applications should be empirically selected on the basis of the specific needs of the LFIA applications rather than just based on the characterizations with ELISA.

In summary, the present study demonstrated that a large number of antibodies (e.g., the 25 anti-NP antibodies) selected from the GH synthetic antibody libraries bound to 6 representative influenza NPs (including 5 NPs from IAV strains and 1 NP from IBV strain) with corresponding affinities and specificities. Many of the optimal affinities of the selected antibodies for their corresponding NPs were below 1 nM in $EC_{50}$ without the need for affinity maturation. The affinity level was comparable to that of the positive control mouse antibody derived from murine immune system. The selected panel of antibodies together were diverse in specificities, capable of distinguishing NPs with sequence identities up to more than 90%, The GH antibodies derived from the GH antibody libraries without further affinity maturation were used in sandwich ELISA and LFIA to detect the corresponding NPs from lysed influenza viruses with detection limit of 1 nM of NP in specimen. The detection limit was close to the general acceptable detection limit for influenza virus detection with RIDTs. This work demonstrated the feasibility of a general procedure in developing diagnostic antibodies that would be unavailable from animal-based antibody technologies.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for selecting an antibody fragment specific to an influenza virus, comprising, (a) providing a phage-displayed single-chain variable fragment (scFv) library that comprises a plurality of phage-displayed scFvs, wherein the heavy chain variable (VH) domain of each phage-displayed scFvs has a binding affinity to protein A, and the light chain variable (VL) domain of each phage-displayed scFvs has a binding affinity to protein L;

(b) exposing the phage-displayed scFv library of the step (a) to a target nucleoprotein comprising an amino acid sequence selected from the group consisting of SEQ ID NOs: 1-6;

(c) selecting, from the phage-displayed scFv library of the step (b), a first plurality of phages that respectively express scFvs exhibiting binding affinity to the target nucleoprotein;

(d) exposing the first plurality of phages selected in the step (c) to the target nucleoprotein in the presence of at least one scrambled nucleoprotein, wherein the scrambled nucleoprotein comprises an amino acid sequence selected from the group consisting of SEQ ID NOs: 1-6, and the amino acid sequence of the scrambled nucleoprotein is different from the amino acid sequence of the target nucleoprotein;

(e) selecting, from the first plurality of phages of the step (d), a second plurality of phages that respectively express scFvs exhibiting binding affinity to the target nucleoprotein in the presence of the scrambled nucleoprotein;

(f) respectively enabling the second plurality of phages selected in the step (e) to express a plurality of soluble scFvs;

(g) exposing the plurality of soluble scFvs of the step (f) to the target nucleoprotein;

(h) determining the respective binding affinity of the plurality of soluble scFvs in the step (g); and (i) based on the results determined in the step (h), selecting one soluble scFv that exhibits superior affinity over the other soluble scFvs of the plurality of soluble scFvs as the antibody fragment.

2. The method of claim 1, wherein the influenza virus is influenza virus type A or type B.

3. The method of claim 2, wherein the influenza virus type A is H1N1, H3N2, or H5N1.

4. A recombinant antibody or an antigen binding fragment thereof, comprising a VL domain and a VH domain, wherein the VL domain comprises a first light chain complementarity determining region (CDR-L1), a second light chain CDR (CDR-L2) and a third light chain CDR (CDR-L3), and the VH domain comprises a first heavy chain CDR (CDR-H1), a second heavy chain CDR (CDR-H2) and a third heavy chain CDR (CDR-H3), wherein the CDR-L1, the CDR-L2, the CDR-L3, the CDR-H1, the CDR-H2 and the CDR-H3 respectively comprise the amino acid sequences of SEQ ID NOs: 7-12;

the CDR-L1, the CDR-L2, the CDR-L3, the CDR-H1, the CDR-H2 and the CDR-H3 respectively comprise the amino acid sequences of SEQ ID NOs: 13-18;

the CDR-L1, the CDR-L2, the CDR-L3, the CDR-H1, the CDR-H2 and the CDR-H3 respectively comprise the amino acid sequences of SEQ ID NOs: 19-24;

the CDR-L1, the CDR-L2, the CDR-L3, the CDR-H1, the CDR-H2 and the CDR-H3 respectively comprise the amino acid sequences of SEQ ID NOs: 25-30;

the CDR-L1, the CDR-L2, the CDR-L3, the CDR-H1, the CDR-H2 and the CDR-H3 respectively comprise the amino acid sequences of SEQ ID NOs: 31-36;

the CDR-L1, the CDR-L2, the CDR-L3, the CDR-H1, the CDR-H2 and the CDR-H3 respectively comprise the amino acid sequences of SEQ ID NOs: 37-42;

the CDR-L1, the CDR-L2, the CDR-L3, the CDR-H1, the CDR-H2 and the CDR-H3 respectively comprise the amino acid sequences of SEQ ID NOs: 43-48;

the CDR-L1, the CDR-L2, the CDR-L3, the CDR-H1, the CDR-H2 and the CDR-H3 respectively comprise the amino acid sequences of SEQ ID NOs: 49-54;

the CDR-L1, the CDR-L2, the CDR-L3, the CDR-H1, the CDR-H2 and the CDR-H3 respectively comprise the amino acid sequences of SEQ ID NOs: 55-60;

the CDR-L1, the CDR-L2, the CDR-L3, the CDR-H1, the CDR-H2 and the CDR-H3 respectively comprise the amino acid sequences of SEQ ID NOs: 61-66;

the CDR-L1, the CDR-L2, the CDR-L3, the CDR-H1, the CDR-H2 and the CDR-H3 respectively comprise the amino acid sequences of SEQ ID NOs: 67-72;

the CDR-L1, the CDR-L2, the CDR-L3, the CDR-H1, the CDR-H2 and the CDR-H3 respectively comprise the amino acid sequences of SEQ ID NOs: 73-78;

the CDR-L1, the CDR-L2, the CDR-L3, the CDR-H1, the CDR-H2 and the CDR-H3 respectively comprise the amino acid sequences of SEQ ID NOs: 79-84;

the CDR-L1, the CDR-L2, the CDR-L3, the CDR-H1, the CDR-H2 and the CDR-H3 respectively comprise the amino acid sequences of SEQ ID NOs: 85-90;

the CDR-L1, the CDR-L2, the CDR-L3, the CDR-H1, the CDR-H2 and the CDR-H3 respectively comprise the amino acid sequences of SEQ ID NOs: 91-96;

the CDR-L1, the CDR-L2, the CDR-L3, the CDR-H1, the CDR-H2 and the CDR-H3 respectively comprise the amino acid sequences of SEQ ID NOs: 97-102;

the CDR-L1, the CDR-L2, the CDR-L3, the CDR-H1, the CDR-H2 and the CDR-H3 respectively comprise the amino acid sequences of SEQ ID NOs: 103-108;

the CDR-L1, the CDR-L2, the CDR-L3, the CDR-H1, the CDR-H2 and the CDR-H3 respectively comprise the amino acid sequences of SEQ ID NOs: 109-114;

the CDR-L1, the CDR-L2, the CDR-L3, the CDR-H1, the CDR-H2 and the CDR-H3 respectively comprise the amino acid sequences of SEQ ID NOs: 115-120;

the CDR-L1, the CDR-L2, the CDR-L3, the CDR-H-1, the CDR-H2 and the CDR-H3 respectively comprise the amino acid sequences of SEQ ID NOs: 121-126;

the CDR-L1, the CDR-L2, the CDR-L3, the CDR-H1, the CDR-H2 and the CDR-H3 respectively comprise the amino acid sequences of SEQ ID NOs: 127-132;

the CDR-L1, the CDR-L2, the CDR-L3, the CDR-H1, the CDR-H2 and the CDR-H3 respectively comprise the amino acid sequences of SEQ ID NOs: 133-138;

the CDR-L1, the CDR-L2, the CDR-L3, the CDR-H1, the CDR-H2 and the CDR-H3 respectively comprise the amino acid sequences of SEQ ID NOs: 139-144;

the CDR-L1, the CDR-L2, the CDR-L3, the CDR-H1, the CDR-H2 and the CDR-H3 respectively comprise the amino acid sequences of SEQ ID NOs: 145-150; or the CDR-L1, the CDR-L2, the CDR-L3, the CDR-H1, the CDR-H2 and the CDR-H3 respectively comprise the amino acid sequences of SEQ ID NOs: 151-156.

5. The recombinant antibody or the antigen binding fragment thereof of claim 4, wherein the VL domain and the VH domain respectively comprise amino acid sequences at least 85% identical to SEQ ID NOs: 157 and 158;

the VL domain and the VH domain respectively comprise amino acid sequences at least 85% identical to SEQ ID NOs: 159 and 160;

the VL domain and the VH domain respectively comprise amino acid sequences at least 85% identical to SEQ ID NOs: 161 and 162;

the VL domain and the VH domain respectively comprise amino acid sequences at least 85% identical to SEQ ID NOs: 163 and 164;

the VL domain and the VH domain respectively comprise amino acid sequences at least 85% identical to SEQ ID NOs: 165 and 166;

the VL domain and the VH domain respectively comprise amino acid sequences at least 85% identical to SEQ ID NOs: 167 and 168;

the VL domain and the VH domain respectively comprise amino acid sequences at least 85% identical to SEQ ID NOs: 169 and 170;

the VL domain and the VH domain respectively comprise amino acid sequences at least 85% identical to SEQ ID NOs: 171 and 172;

the VL domain and the VH domain respectively comprise amino acid sequences at least 85% identical to SEQ ID NOs: 173 and 174;

the VL domain and the VH domain respectively comprise amino acid sequences at least 85% identical to SEQ ID NOs: 175 and 176;

the VL domain and the VH domain respectively comprise amino acid sequences at least 85% identical to SEQ ID NOs: 177 and 178;

the VL domain and the VH domain respectively comprise amino acid sequences at least 85% identical to SEQ ID NOs: 179 and 180;

the VL domain and the VH domain respectively comprise amino acid sequences at least 85% identical to SEQ ID NOs: 181 and 182;

the VL domain and the VH domain respectively comprise amino acid sequences at least 85% identical to SEQ ID NOs: 183 and 184;

the VL domain and the VH domain respectively comprise amino acid sequences at least 85% identical to SEQ ID NOs: 185 and 186;

the VL domain and the VH domain respectively comprise amino acid sequences at least 85% identical to SEQ ID NOs: 187 and 188;

the VL domain and the VH domain respectively comprise amino acid sequences at least 85% identical to SEQ ID NOs: 189 and 190;

the VL domain and the VH domain respectively comprise amino acid sequences at least 85% identical to SEQ ID NOs: 191 and 192;

the VL domain and the VH domain respectively comprise amino acid sequences at least 85% identical to SEQ ID NOs: 193 and 194;

the VL domain and the VH domain respectively comprise amino acid sequences at least 85% identical to SEQ ID NOs: 195 and 196;

the VL domain and the VH domain respectively comprise amino acid sequences at least 85% identical to SEQ ID NOs: 197 and 198;

the VL domain and the VH domain respectively comprise amino acid sequences at least 85% identical to SEQ ID NOs: 199 and 200;

the VL domain and the VH domain respectively comprise amino acid sequences at least 85% identical to SEQ ID NOs: 201 and 202;

the VL domain and the VH domain respectively comprise amino acid sequences at least 85% identical to SEQ ID NOs: 203 and 204; or the VL domain and the VH domain respectively comprise amino acid sequences at least 85% identical to SEQ ID NOs: 205 and 206.

6. The recombinant antibody fragment or the antigen binding fragment thereof of claim 5, wherein the VL domain and the VH domain respectively comprise amino acid sequences 100% identical to SEQ ID NOs: 157 and 158;

the VL domain and the VH domain respectively comprise amino acid sequences 100% identical to SEQ ID NOs: 159 and 160;

the VL domain and the VH domain respectively comprise amino acid sequences 100% identical to SEQ ID NOs: 161 and 162;

the VL domain and the VH domain respectively comprise amino acid sequences 100% identical to SEQ ID NOs: 163 and 164;

the VL domain and the VH domain respectively comprise amino acid sequences 100% identical to SEQ ID NOs: 165 and 166;

the VL domain and the VH domain respectively comprise amino acid sequences 100% identical to SEQ ID NOs: 167 and 168;

the VL domain and the VH domain respectively comprise amino acid sequences 100% identical to SEQ ID NOs: 169 and 170;

the VL domain and the VH domain respectively comprise amino acid sequences 100% identical to SEQ ID NOs: 171 and 172;

the VL domain and the VH domain respectively comprise amino acid sequences 100% identical to SEQ ID NOs: 173 and 174;

the VL domain and the VH domain respectively comprise amino acid sequences 100% identical to SEQ ID NOs: 175 and 176;

the VL domain and the VH domain respectively comprise amino acid sequences 100% identical to SEQ ID NOs: 177 and 178;

the VL domain and the VH domain respectively comprise amino acid sequences 100% identical to SEQ ID NOs: 179 and 180;

the VL domain and the VH domain respectively comprise amino acid sequences 100% identical to SEQ ID NOs: 181 and 182;

the VL domain and the VH domain respectively comprise amino acid sequences 100% identical to SEQ ID NOs: 183 and 184;

the VL domain and the VH domain respectively comprise amino acid sequences 100% identical to SEQ ID NOs: 185 and 186;

the VL domain and the VH domain respectively comprise amino acid sequences 100% identical to SEQ ID NOs: 187 and 188;

the VL domain and the VH domain respectively comprise amino acid sequences 100% identical to SEQ ID NOs: 189 and 190;

the VL domain and the VH domain respectively comprise amino acid sequences 100% identical to SEQ ID NOs: 191 and 192;

the VL domain and the VH domain respectively comprise amino acid sequences 100% identical to SEQ ID NOs: 193 and 194;

the VL domain and the VH domain respectively comprise amino acid sequences 100% identical to SEQ ID NOs: 195 and 196;

the VL domain and the VH domain respectively comprise amino acid sequences 100% identical to SEQ ID NOs: 197 and 198;

the VL domain and the VH domain respectively comprise amino acid sequences 100% identical to SEQ ID NOs: 199 and 200;

the VL domain and the VH domain respectively comprise amino acid sequences 100% identical to SEQ ID NOs: 201 and 202;

the VL domain and the VH domain respectively comprise amino acid sequences 100% identical to SEQ ID NOs: 203 and 204; or the VL domain and the VH domain respectively comprise amino acid sequences 100% identical to SEQ ID NOs: 205 and 206.

7. A method of diagnosing whether a subject is infected by an influenza virus via a biological sample isolated from the subject, comprising detecting the presence or absence of a nucleoprotein of the influenza virus in the biological sample by use of the recombinant antibody or the antigen binding fragment thereof of claim 4, wherein the presence of the nucleoprotein indicates that the subject is infected by the influenza virus.

8. The method of claim 7, wherein the influenza virus is influenza virus type A or type B.

9. The method of claim 8, wherein the influenza virus type A is H1N1, H3N2, or H5N1.

10. The method of claim 7, wherein the subject is a human.

* * * * *